US008640710B2

(12) United States Patent
Matthews

(10) Patent No.: US 8,640,710 B2
(45) Date of Patent: Feb. 4, 2014

(54) ORTHODONTIC PROTRACTION HEADGEAR APPLIANCE PROTECTIVE COVER ASSEMBLY

(76) Inventor: Sara Matthews, Milton, WA (US)

( * ) Notice: Subject to any disclaimer, the term of this patent is extended or adjusted under 35 U.S.C. 154(b) by 289 days.

(21) Appl. No.: 13/074,404

(22) Filed: Mar. 29, 2011

(65) Prior Publication Data

US 2012/0247490 A1    Oct. 4, 2012

(51) Int. Cl.
*A61F 13/00* (2006.01)
*A62B 18/08* (2006.01)
*A61C 3/00* (2006.01)

(52) U.S. Cl.
USPC ............. 128/889; 128/206.24; 128/207.11; 433/5

(58) Field of Classification Search
USPC ............ 128/889, 857–858, 846–847, 207.11, 128/206.21; 2/410, 424, 209.13, 209.12; 112/441, 408, 437; 433/5, 7, 18, 24
See application file for complete search history.

(56) References Cited

U.S. PATENT DOCUMENTS

| 8,235,045 | B2 * | 8/2012 | Moore | ................. 128/206.24 |
| 2009/0107507 | A1 | 4/2009 | Moore | |
| 2010/0258132 | A1 | 10/2010 | Moore | |

OTHER PUBLICATIONS

Martin Epstein, DDS; Joshua Epstein, DMD; Garri Tsibel,DDS, "Management of the Developing Class III Malocclusion With Face Mask Therapy and Palatal Expansion" found at: http://www.scribd.com/doc/13496463/.
Silopad Gel Liners for Adaptable Class III Mask—Great Lakes Orthodontics, found at www.greatlakesortho.com.

* cited by examiner

*Primary Examiner* — Patricia Bianco
*Assistant Examiner* — Ophelia A Hawthorne
(74) *Attorney, Agent, or Firm* — Patentrending, PLLC; Elizabeth Reilly

(57) ABSTRACT

The present invention is a protective cover assembly, pattern, and method for use for installation upon an external orthodontic headgear protraction appliance having a chin cup interface and a forehead pad interface. The present invention includes two aspects of a protective cover assembly, a protective chin cup cover assembly and a protective forehead pad cover assembly. Each protective cover assembly provides an absorbing soft cushioning fleece membrane between the facial skin of an orthodontic patient wearer and the hard surfaces of the orthodontic protraction headgear interfaces to prevent against a plurality of discomforts which result from wearing the orthodontic protraction headgear appliance during treatment of Class III Malocclusion; and configured to improve compliancy of use of the orthodontic protraction appliance in the orthodontic population, especially among growing children and adolescents.

13 Claims, 37 Drawing Sheets

FIG. 20
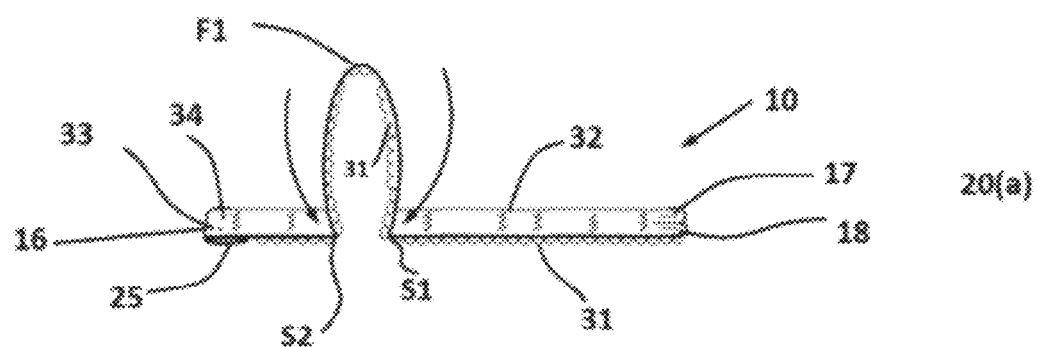
20(a)
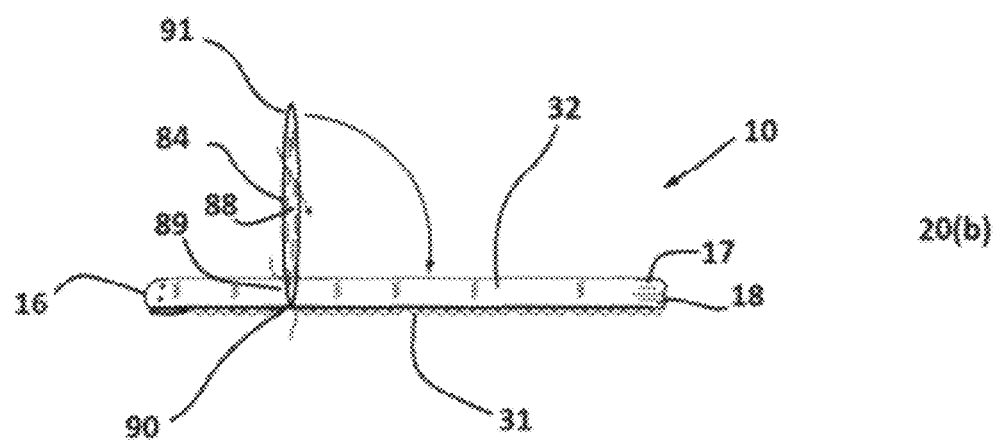
20(b)
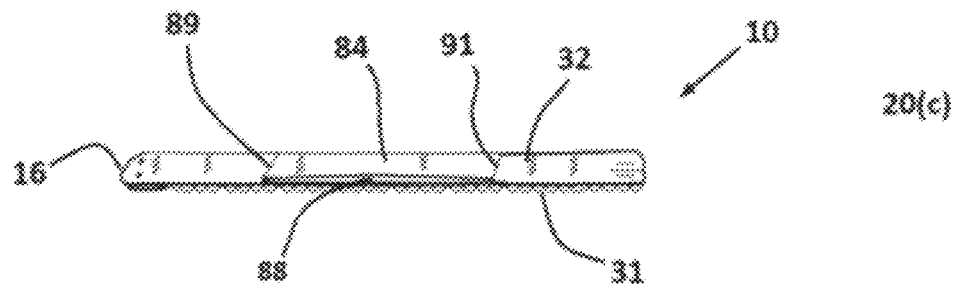
20(c)

FIG. 26
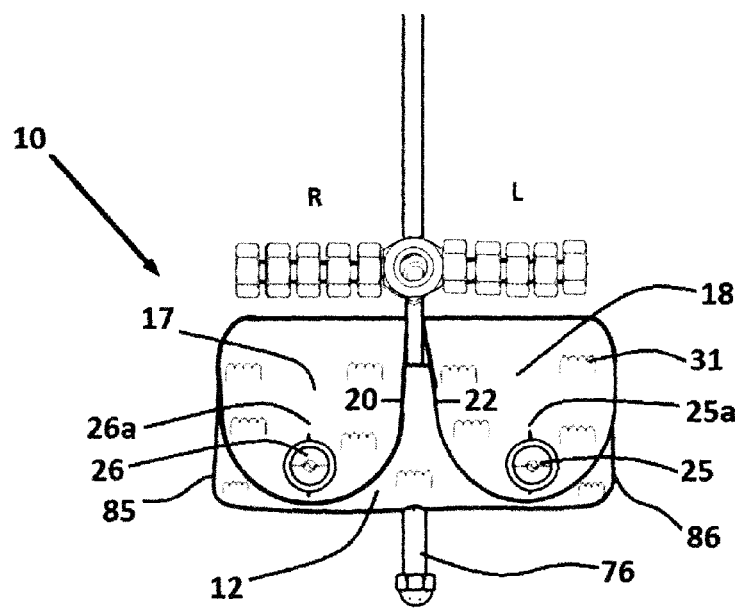
26(a)
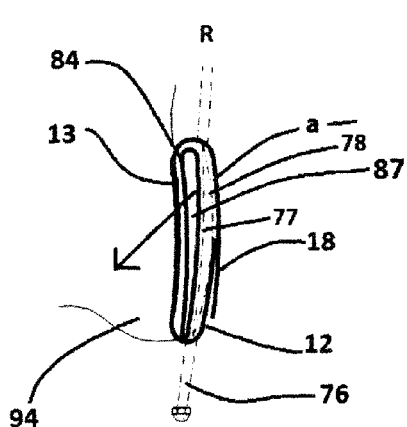
26(b)
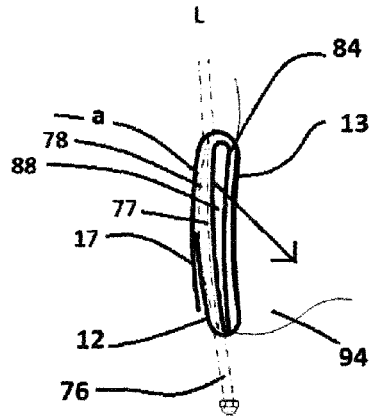
26(c)

FIG. 31
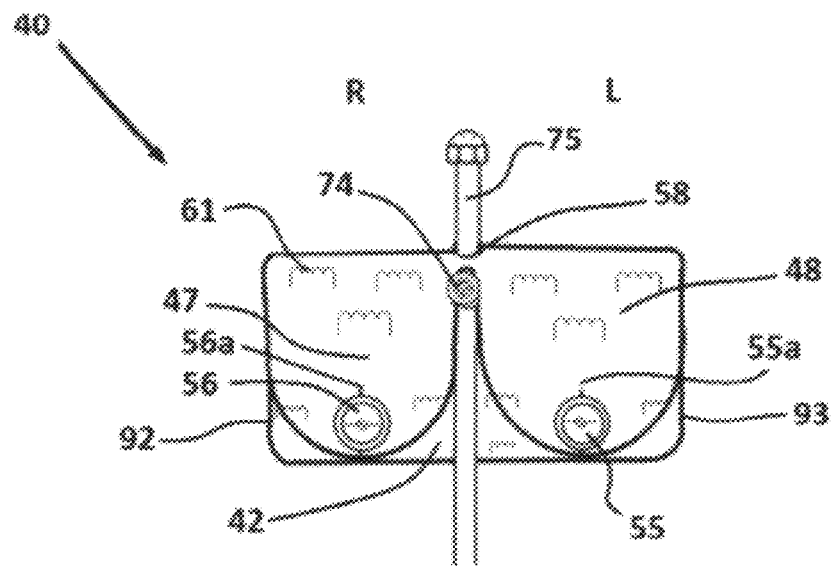
31(a)
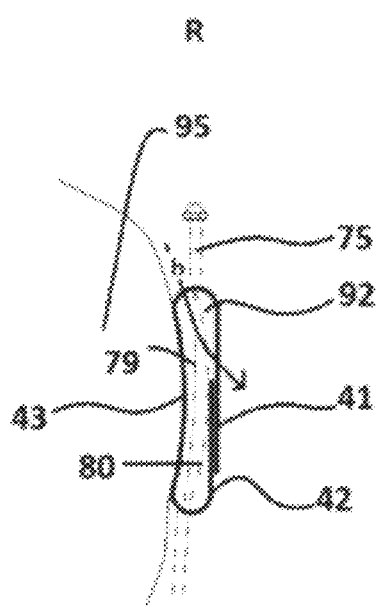 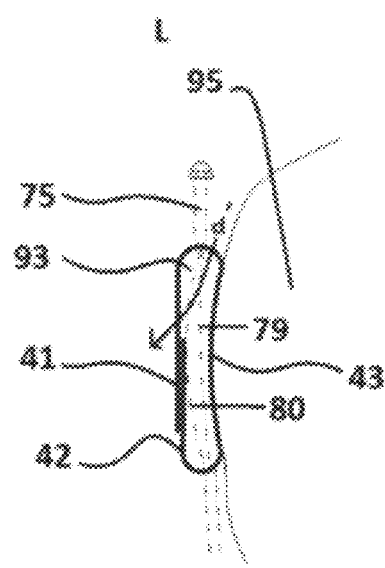
31(b) 31(c)

ORTHODONTIC PROTRACTION HEADGEAR APPLIANCE PROTECTIVE COVER ASSEMBLY

FIELD OF THE INVENTION

This invention relates generally to the art of a protective cove-r assembly for the chin cup and forehead pad interfaces of an orthodontic protraction headgear appliance which is worn by an orthodontic patient for the treatment of Class III Malocclusion disorder (underbite). In particular, the invention relates to cover assemblies for the orthodontic protraction headgear appliance chin cup interface and a cover for the forehead pad interface to protect the wearer's facial skin on the chin and wearer's facial skin on the forehead and underlying tissues thereof; and to protect against typical discomforts inherent in wearing the orthodontic appliance, such as cracked skin, redness, pressure sores, decubitus sores, allergic reactions, breakouts, lingering skin indentations, and suction marks. In addition, the present invention relates to a cover assembly and material for said cover, to provide alleviation from pressure imposed by the chin cup and the forehead pad of the orthodontic protraction headgear appliance and thereby reduce the occurrence of lingering facial indentations, suction marks, pressure sores, decubitus sores, cracked skin, and consequentially reduce the occurrence of infection.

This invention as noted, relates to formation of pressure sores, decubitus sores, irritation, redness, cracking of skin, microbial infection, discomfort, facial indentations, allergic reactions, and other skin disorders at the site of the chin and forehead due to the combination of moisture, perspiration, saliva and pressure imposed on the wearer of the orthodontic protraction headgear appliance used in the treatment of Class III Malocclusion.

This invention also relates to a decorative cover assembly for use to cover the orthodontic protraction headgear appliance interfaces used in the treatment of Class III Malocclusions.

This invention also relates to a soft comfortable cover assembly which is easy to install and remove for washing providing a hygienic protective covers for the chin cup interface and the forehead pad interface of an orthodontic protraction headgear appliance and thereby to improve compliance with wearing the orthodontic protraction headgear appliance among orthodontic patients, particularly growing children and adolescents.

BACKGROUND OF THE INVENTION

Orthodontic treatment goals are to provide patients with properly aligned teeth, a functional occlusion, and optimal facial and jaw aesthetics and focuses on diagnosis, therapy, and treatment of dentoalveolar and skeletal malocclusions, or generally straightening and positioning teeth for the health, comfort, safety and aesthetics of the patient. Orthodontic treatment frequently relies on the use of removable orthodontic protraction headgear appliances to provide forces to teeth and facial bones in order to correct spatial malrelations between the teeth and/or jawbones. The removable nature of these appliances requires the orthodontic patients, typically growing children and adolescents comply with the orthodontist's treatment to wear the orthodontic protraction appliance. Unfortunately, because of the discomforts associated with orthodontic appliances, poor compliance is the rule rather than the exception with wearing removable orthodontic appliances. Orthodontic protraction headgear appliances have been used since the nineteenth century and discomforts associated with their use have been a faithful cohort. They are a removable type of orthodontic appliance that patients are typically advised to wear 8-12 hours and typically while sleeping.

More particularly, an orthodontic protraction headgear appliance is used in treatment for Class III Malocclusion (underbite) characterized by the lower teeth positioned anterior to or in front of the upper teeth when in centric occlusion. Class III Malocclusion is seen in growing children and adolescents. The etiology involved in Class III Malocclusions can range from a dental condition to a more severe skeletal malrelationship. In Class III Dental Malocclusion, teeth are tipped towards the underbite position with normal maxillary and mandibular relationships. In skeletal malocclusion, the size or relative position of the maxilla and mandible varies. For example, the maxilla can be positioned posterior to an ideally positioned mandible. In another case, the mandible is positioned anterior to an ideally positioned maxilla. Class III Malocclusions may be due to maxillary deficiency and/or normal or slightly prognathic mandible or, at one time, thought of as excessive mandibular growth. Therefore, considerable attention has been given to early treatment using maxillary protraction therapy.

Treatment of Class III Malocclusion, characterized by open bite pattern, is difficult since such malocclusions result from many etiological factors. Skeletal open bite cases are usually associated with an increase in the vertical growth of the maxillary posterior dentoalveolar segments and much of therapy focuses on maxillary protraction with use of reversae pull headgear appliances. The application of conventional reverse headgear, with the associated application of mesially directed force (below the center of resistance of maxillary dentition) tends to increase the anterior open bite. The intrusion of posterior teeth becomes more difficult with age, as mechanical treatment options are limited in adult patients. Orthognathic surgery may be indicated in adult patients with severe open bite and Class III skeletal patterns with retrognathic maxilla. Therefore, compliance to wearing the orthodontic headgear is imperative when the patient is young.

Orthodontic protraction headgear appliances have been used since the 1960's and commercially available reverse pull headgear designs typically have a metal or acrylic intra-oral portion attached to the teeth, and an extra-oral portion or chin cup interface member that presses against the chin of the patient and a forehead pad interface that presses against the forehead of the patient. The protraction headgear appliance also includes a vertical main frame metal bar, metal screws, end caps, and horizontal cross bar which is used with elastic bands. The metal or acrylic intra-oral portion, or horizontal crossbar, is attached to the patient's teeth with elastic bands that exert from 300-800 grams on the right and left sides and also exerts pressure against the patient's chin. The direction of elastic traction is downward and forward at the level of the lips and not parallel to the Frankfurt horizontal plane. This produces a counter clockwise or upward and forward rotation of the maxilla while protracting and backward and downward rotation of the mandible and proclination of the maxillary incisors. This method for treating a Class III malocclusion involving a retracted maxilla is to exert a generally mesially directed force on the boney structures of the lower face by engaging the upper arch of the orthodontic patient. These types of force stimulate bone growth to advance the maxilla mesially and/or orthodontically advance the patient's detention. Pressure is also applied to the wearer's facial skin at the chin by the point of force of the headgear chin cup. Pressure is also applied against the wearer's facial skin at forehead by the point of force of the headgear forehead pad. Undesirable side effects are associated with the device that contribute to discomfort to the patient and non-adherence to the treatment. Therefore, a soft absorbent cushiony cover for the orthodontic protraction headgear chin cup interface and the headgear forehead pad interface is needed to assuage the discomforts of the appliance and increase compliance.

The present invention is a protective cover assembly, method for use, and pattern for forming said protective cover assembly, for a chin cup interface and forehead pad interface of an orthodontic protraction headgear appliance to provide an absorbing means, cushioning means, and buffering means, to enable protection against deposits of saliva and perspiration, formation of cracked skin, breakouts, redness, lingering facial indentations, suction marks, irritation, discomfort, pressure sores, decubitus sores, microbial infection, allergic reactions, and other skin disorders, and to consequentially improve comfort while an orthodontic patient is wearing the orthodontic protraction headgear appliance and thereby improve compliance among patients during treatment of Class III Malocclusion disorder. It is an important to note that the protective cover assemblies, according to the preferred embodiment of the present invention do not interfere with the two important issues of orthodontic protraction treatment, i.e., friction and management of forces on the teeth.

This present invention is directed toward assuaging discomforts associated with use of the orthodontic protraction headgear appliance by providing comfort with an absorbing, cushioning, buffering membrane which is positioned between the patient's chin and the hard surface of a chin cup interface; and by providing an absorbing, cushioning, buffering, membrane which is positioned between the patient's forehead and the hard surface of the forehead pad interface to absorb, cushion, and buffer against the impact of the forces of the interfaces. One of the paramount objectives of the protective cover assemblies of the present invention is to increase comfort to the orthodontic patient and thereby decrease nonadherance to the treatment of Class III Malocclusion due to discomforts associated with the use of the orthodontic protraction headgear appliance.

The orthodontic protraction headgear appliance includes a chin cup interface and a forehead cup interface which forces varying pressure against the wearers chin and forehead to assist in the therapy for Class III Malocclusion disorder. The chin cup interface and forehead pad interface includes a hard surface, typically plastic, or other material, which when in use leans closely and tightly against the wearer's chin and forehead and as a result, when using the orthodontic protraction headgear appliance properly, the wearer can incur skin irritation, pressure sores, decubitus sores, redness, irritation, cracked skin, skin allergies, lingering facial indentations, breakouts, or other skin disorders, at the site of the chin and the forehead. More particularly, when the patient is using the orthodontic protraction headgear at night while sleeping, the patient is attached to the appliance at the horizontal cross bar by rubber bands stretching through his/her mouth and hooking to hardware surrounding his/her teeth. This situation fosters drool, saliva, mouth leaks, oral flora, to leak down the wearer's mouth and into the area between the wearer's chin and the orthodontic protraction headgear chin cup interface which consequentially supports an ideal environment for the growth of pathogenic microorganisms or the growth of opportunistic microorganisms. Together with the pressure of the chin cup interface which causes skin irritation, cracked skin, pressure sores, decubitus sores, and the like, an environment is created which provides a medium for cultivation which may support the growth of cultures of known skin pathogens, the likes of Methicillin Resistant *Staphylococcus aureus* (MRSA), *Streptococcus pyogenes* (impetigo), *Tinea* (ring worm), *Herpes species* virus.

In general, pressure sores, and decubitus sores may form on parts or portions of a patient's skin and body when in contact for a prolonged period of time with an object, such as for example, in this instant case, an orthodontic protraction headgear interface that exerts a pressure against the human facial skin. These sores can be seen in patients who are wearing the orthodontic protraction headgear appliance during treatment of Class III Malocclusion, where the pressure sores develop within soft tissue of the chin and the forehead that is compressed between the hard surface of the orthodontic protraction headgear interfaces a patient's weight-bearing bony prominences. In addition, pressure sores develop depending on the external environmental factors including the firmness and friction of the supporting surface against the patient's skin, the patient/ambient temperature, the amount of moisture in contact with the skin, and the health and susceptibility of the skin due to age or illness or pre-existing skin irritation, and hygiene.

Here, particularly, the pressure exerted on the skin covering or surrounding the chin boney prominences and the forehead boney prominences on the portions of the patient's body that are in contact with the hard surfaces of the orthodontic protraction headgear chin cup interface and the headgear forehead pad interface can result in the patient's facial skin and/or underlying tissue associated with the chin and forehead becoming inflamed, cracked, open, and may obstruct or restrict the blood flow to the skin and/or the underlying tissue, causing the skin and underlying tissue to become ischemic, eventually resulting in the development of pressure sores, or decubitus sores. Decubitus sores can form in any area of tissue covering a bony prominence that is in contact with the hard plastic surface of the orthodontic protraction headgear interfaces upon which the patient's face and skin is congruently pressing therewith.

Moreover the orthodontic protraction headgear chin cup interface and forehead pad interface may apply sufficient pressure to the wearer's chin and forehead resulting in discomfort and skin irritation, red marks, lingering linear indentations on their faces, and suction marks, after only several hours of use of the orthodontic protraction headgear appliance. In addition, the chin area and the forehead portion is distorted beyond its normal range of elasticity to conform to certain facial contours dictated by the headgear interfaces, thus requiring the application of excessive forces to create a seal between the wearer's chin and the chin cup interface and to create a seal between the wearer's forehead and the forehead pad interface. In most cases, these excessive forces may cause the wearer's chin and forehead to distort to conform to the chin cup interface and the forehead interface which increases wearer discomfort, facial soreness, cracked skin, and ulceration.

Initially, pressure on the chin skin and the forehead skin and underlying tissues may lead to pink coloration and/or mild inflammation, which may linger for a few hours of relieving pressure on the chin or the forehead when removing the orthodontic protraction headgear appliance. If pressure is not relieved for a long time, such as when the patient is sleeping while wearing the orthodontic protraction headgear appliance, superficial lesions can form on the chin facial skin, and the forehead facial skin, then developing into sores which continue growing deeper until extending toward the bones and to the blood system and can become infected and manifest as impetigo, MRSA, or hand—to mouth—to eye pink eye infections, to name a few. Commonly known pathogens isolated from pressure sores and decubitus sores are MRSA, *Streptococcus pyogenes, Candida albicans*. Other skin infections which can arise may be caused by *Tinea* forming ring worm. Hand—to mouth—to eye infections which may incur can be caused by infectious organisms *Streptococcus pneumonia* and *Haemophilus influenza*.

A conventional means for preventing the development of pressure sores and decubitus sores is to reduce the amount of time a specific body part is subjected to straining pressure; using specialized materials designed to lessen the weight-pressure that is brought to bear on the patient's bony prominences; and medicinal treatments and methods of treating the sore after it occurs. Here, in this case, it is to the detriment and against the teaching of successful treatment of Class III Malocclusion disorder to reduce the amount of time the patient must wear the orthodontic protraction headgear appliance. Reducing time the patient wears the headgear eventually extends the life of the treatment which is disadvantageous because as time progresses the patient grows older and the orthodontic disorder is harder to correct. It is a detriment to wait until the cracked skin and sores appear because orthodontic treatment would also have to be paused and the treatment of antibiotics on pressure sores can induce development of resistant bacteria, for example, MRSA and Vancomycin Resistant *Enterococcus* (VRE). Therefore, a means for mechanically alleviating the amount of straining pressures imposed on the chin and forehead is critically needed. There is no orthodontic protraction headgear appliance that soothes the amount of pressure imposed by the chin and forehead interfaces against the wearer's chin and forehead, and underlying tissues.

As mentioned, the orthodontic patient who must wear the orthodontic protraction headgear appliance during treatment for Class III Malocclusion disorder is vulnerable to cultivation by pathogenic microorganisms or opportunistic microorganisms at the site of the chin and forehead compressed under contact with the chin cup interface and forehead pad interface. As a result the wearer of the orthodontic headgear appliance is susceptible to eye infections when perspiration and moisture formed between the skin of the wearer's forehead and the headgear's forehead cup becomes infected and contaminated with microorganisms. Even more so, when a patient applies the rubber bands to his mouth and attaches them to the headgear, the patient may contaminate his hands with oral bacterial flora. It is known that some people in the community are carriers of *Streptococcus pyogenes* along with the normal bacterial flora of their throats. In addition, *Haemophilus* influenza can be a cause of epiglottis infections. Both *S. pyogenes* and *H. influenza* therefore, can be transferred by hand—to mouth—to the patient's eyes causing pink eye, or other eye infections. In addition, *S. pyogenes* can cause impetigo around the nose and mouth. In addition, the wearer may be touching the headgear forehead chin and chin cup with his hands while adjusting it to relieve discomfort. Contamination to the forehead area and the chin area from unwashed hands is likely to occur.

A patient wearing the orthodontic protraction headgear appliance and subject to at least 12 hours of wear and pressure upon the bony areas of the chin and forehead can promote the infestation and cultivation of fungal infections. Fungi cause a wide variety of diseases in humans. Some fungi cause infections to the outermost layers of the skin (superficial mycoses), other fungi cause cutaneous mycoses by penetrating to the keratinized layers of the skin, triggering pathologic changes in the patient. *Derinatophytes*, including *Trichophyton rubrum* and *Trichophyton mentagrophytes* are fungal infections of the skin or Dermatophytoses. Of particular interest, here, is *Tinea barbae* or *Tinea faciale*, which causes erythema, scaling, and pustules in the chin, beard and neck area, or round, bald, scaly patches in the scalp. Secondary bacterial infections may develop from the fungal infection.

For the reason that orthodontic patients are typically growing children or adolescents and who are commonly participants in contact sports, *Tinea*, or commonly referred to as "ringworm", is very common concern, especially among children and adolescents, and may be spread by skin-to-skin contact, as well as via contact with contaminated items. Ringworm spreads readily, as those infected are contagious even before they show symptoms of the disease. Participants in contact sports such as wrestling, which is increasingly popular among children and adolescents, have a risk of contracting the fungal infection through skin-to-skin contact. Similarly, MRSA infections have been known reported among participants of wrestling teams. Ringworm is mildly contagious and can be caught from other humans, both by direct contract and by prolonged contact with flakes of shed skin, from sharing clothes, towels, etc. The best known sign of *Tinea* in people is the appearance of one or more red raised itchy patches with defined annular edges. These patches are often lighter in the center, taking on the appearance of a ring with hyperpigmentation around the circumference caused by an increase in melanin. The affected area may become itchy for periods of time.

Fungal infections have significant effects on a patient's social, occupational, school attendance, and emotional functioning. Feeling of embarrassment may preclude patients from interacting in a social, school, sport, or working environment where they are unwilling to show their face. Moreover, orthodontic patients affected by fungal infections are especially at risk of developing secondary bacterial infections. Medically, fungal infections are very difficult to treat and take a very long time to eradicate symptoms.

Therefore, there is a significant need for the instant invention, as a protective mechanical barrier and membrane for the patient's skin at the site of the chin and forehead against invasive bacteria, fungi, viruses; and to provide protection against the hard surface of the orthodontic protraction headgear interfaces; and prevent the development of pressure sores which may harbor and cultivate microbial contaminants. The present invention satisfies these needs.

When the orthodontic protraction headgear appliance is used by the wearer, holding it in place over the chin or the forehead as the wearer carries on daily routines, or while the wearer is sleeping, can be difficult and uncomfortable due to the pressure applied on the chin and forehead and buildup of perspiration, saliva, and mouth leaks, which causes the orthodontic protraction headgear appliance to slide. In addition, as the wearer naturally moves in his/her sleep the device is likely to shift. More particularly, if the headgear becomes uncomfortable due to irritation of the skin, breakouts, or presence of pressure sores at the site of contact of the chin cup and the forehead cup on the wearer's chin or forehead, the wearer is more than likely to move the headgear by his/her own hand. In addition, the headgear pivotally positioned sufficiently against the wearer's chin and forehead can cause indentations on the wearer's face that can linger for hours after removal of the orthodontic protraction headgear appliance.

The unique advantages of using synthetic fleece material for the construction and manufacture of the present invention's protective chin cup cover assembly and protective forehead pad cover assembly is well apparent as evidenced by its inherent softness, suppleness, lightweight, breathability, cushioning, and quick absorbing and quick drying characteristics that is well suited for imparting comfort and absorbency to the wearer of the orthodontic protraction headgear appliance. Synthetic fleece material is available as polyester fleece and can be readily purchased in neighborhood fabric stores.

Another problem that daunts the orthodontic patient from wearing the orthodontic protraction headgear appliance is the overall unforgiving aesthetic design of the orthodontic headgear appliance. The headgear appliance must be worn and used any time during the day or while the wearer is asleep, including nap time, for the duration of the term of the disorder in order to be effective and successful against the orthodontic challenges presented to a patient with Class III Malocclusion. The headgear appliance is unnatural, cumbersome, medicinal, nuisance, distraction, and unattractive on the face of the wearer.

As a result of the varied discomforts, the wearer is likely to discontinue use of the orthodontic appliance before its effectiveness is apparent. Some orthodontic patients remove their orthodontic headgear at night, at times, not realizing he/she has done so. Some patients choose to discontinue treatment for Class III Malocclusion disorder because of the many difficulties and discomforts associated with adjusting to the orthodontic protraction headgear and nightly treatment. Conventional wisdom among many patients, parents, and orthodontists would agree patient non-adherence is a challenging problem. In addition, to its economic cost, non-adherence can result in protracted treatment and failure to achieve successful orthodontic correction in a timely fashion.

The chin cup interface member and the forehead pad interface membrane of the orthodontic protraction headgear appliance is usually manufactured with hard surfaces, typically plastic, which stains easily from normal use and therefore requires regular cleaning of skin perspiration and skin bacterial flora which intrudes on the surface of the chin cup and the forehead cup. Some orthodontists offer an adhesive synthetic plastic foam pad to peel and stick on to the dorsal side of the headgear interfaces. These adhesive headgear chin cups and forehead cups wear out from repeated daily and nightly use and usually need to be replaced. The orthodontic protraction headgear appliance is costly in itself, therefore incurring additional costs, by repeatedly purchasing disposable accessories, should be prevented.

Orthodontic protraction headgear appliances have similar specifications and use thereof, including a chin cup interface and a forehead pad interface. These structures vary in size of chin cup and forehead cup and dimensions of the appliance varied by the head size of the user. Having little esthetic choices of orthodontic protraction headgear appliance can negatively affect the dedication the patient has toward the therapy and treatment, especially considering the patients' age, the discomfort it presents, and the time needed to successfully correct Class III Malocclusion disorder.

The two aspects of the present invention, a protective chin cup cover assembly and a protective forehead pad cover assembly, which are also of decorative design, provides an improvement to the orthodontic protraction headgear chin pad interface and forehead pad interface, and while enabling the assuagement of the varied problems related with wearing the headgear, and therefore enables patients to remain compliant with treatment of Class III Malocclusion which consequentially promotes successful treatment and correction of the orthodontic disorder. Without treatment compliance, orthodontic disorders are not corrected and may become more pronounced and difficult to correct as the patient ages as their bones grow and teeth change.

A reliable soft, absorbent, cushiony, breathable membranous removable protective cover assembly for an orthodontic protraction headgear chin cup interface and forehead pad interface would be an invaluable improvement to the orthodontic protraction headgear appliance and provide comfort to the patient, and provide for decrease in the occurrence of: cracked skin, redness, breakouts, allergic reactions, pressure sores, decubitus sores, lingering facial indentations, suction marks, and overall discomfort, and provide for increased compliance by orthodontic patients wearing the orthodontic protraction headgear appliance which consequentially would improve the outcome of successful treatment of Class III Malocclusion patients, particularly growing children and adolescents.

PRIOR ART

In the related art, patents have been issued for orthodontic protraction headgear appliances. These patents have included orthodontic headgear appliances for treatment of orthodontic disorders including Class III and Class II Malocclusion. A search of the prior art did not disclose any soft fleece cover for the orthodontic protraction headgear appliance for the chin cup interface or forehead pad interface that read directly on the claims of the instant invention. However, the following patents, and products were considered related.

Patent No. 2010/0258132

Patent No. 2010/0258132 is unlike the present invention because Patent No. 2010/0258132 provides a headgear pad for Continuous Positive Airway Pressure (CPAP) machine for Obstructive Sleep Apnea. (OSA) to secure around the strap and the present invention is a cover and method for the orthodontic protraction headgear appliance chin cup interface and forehead pad interface. In addition, patent 2010/0258132 requires the interface of the headgear pad to be removed to enable installation of the headgear pad and requires the assistance of an installation tool to enable installation of the headgear pad. The patent was granted for an invention headgear pad for CPAP interface comprising a resilient, sufficiently bulky fabric tube formed in a fashion to provide a secure padding for the headgear straps against the face of a sleep apnea patient. The material is fastened into a hollow tube for surrounding headgear straps. The flexible material incorporates an outer layer of micro fleece or similar material whereby protecting the skin, the softness mentally calms against the face when falling to sleep. This invention increases compliance of therapy by making the treatment more comfortable, more attractive, as well as more private. In addition, the invention enables comfort without lasting impressions on the wearer's skin and to prevent skin irritation, discomfort, indentations, and allergies.

Patent No. 2009/0107507

Patent No. 2009/0107507 is unlike the present invention because Patent No. US 2009/0107507 is a method for padding CPAP face and full face masks forehead and nose bridge area to prevent skin irritation, discomfort, indentions, allergies and ulcers. The pad is attached to the forehead part of the CPAP face mask by way of pockets sewn into the body of the pad. The pad protects the forehead area of the wearer as well as the nose bridge by way of a flap of material that fits between the seal of the mask and the wearer's nose bridge area distributing the pressure from the mask seal. The invention is designed to be colorful, soft and comforting to help people with sleep apnea continue to get the necessary therapy.

Product

Silopad® Gel Liners for Adaptable Class III Mask—Great Lakes Orthodontics www.greatlakesortho.com SILOPAD® Gel Liners for Adaptable Class III Mask—Great Lakes Orthodontics provides a SILOPAD® for chin cup and forehead pad but wear must be discontinued if the patient develops a pink rash or other skin disorders. The closeness to the skin may promote closer contact to the skin attenuating the risk to skin disorders and even the colonization of bacteria requiring small amounts of oxygen.

References

Author: Martin Epstein, DDS; Joshua Epstein, DMD; Garri Tsibel, DDS http://www.scribd.com/doc/134964631Management of the Developing Class III Malocclusion with Face Mask Therapy and Palatal Expansion (pgs.—14-19)

SUMMARY OF THE INVENTION

The present invention is a protective cover assembly having two aspects: a chin cup cover assembly and a protective forehead pad cover assembly, for use with an external orthodontic protraction headgear appliance having a chin cup interface and a forehead pad interface; and said cover assembly providing advantages in the fond of a soft flexible absorbent cover assembly to provide a membrane for protecting the facial skin and underlying tissues of the chin and forehead of an orthodontic patient against the hard synthetic surfaces of a chin cup interface and a forehead pad interface while the orthodontic protraction headgear appliance is worn by a growing child or adolescent orthodontic patient. The protective cover assembly is particularly described and claimed to prevent the wearer from abandoning use of the orthodontic protraction headgear appliance during treatment of Class III Malocclusion because of discomfort, cracked skin, breakouts, skin abrasions, allergic reactions, lingering facial indentations, suction marks, development of pressure sores, or decubitus sores, on the chin or forehead, by providing a soft absorbing cushioning means to mitigate the abrasive environment created between the hard surface of the interfaces and the wearer's facial skin; and to provide an absorbing means to enable the capture of the wearer's moisture, drool, mouth leaks, perspiration, facial skin flora, to prevent against pressure sores, decubitus sores, and primary infection to the wearer's chin and forehead, and secondary infection to the wearer's eyes; and to provide an absorbing means to enable the absorption or dissipation of applied force and pressure from the chin cup interface and the forehead pad interface against the wearer's facial skin and underlying tissues immediate to and surrounding the chin and forehead portions of the face congruent with the chin cup interface and forehead pad interface of the orthodontic protraction headgear appliance while the wearer is using the appliance.

The protective cover assembly, of the present invention, is configured with two aspects: a protective cover assembly for use with a chin cup interface; and a protective forehead pad cover assembly for use with a forehead pad interface, of an orthodontic protraction headgear appliance. The protective cover assembly is configured to provide overall comfort to the wearer or orthodontic patient while using the external orthodontic protraction headgear appliance during treatment of Class III Malocclusion disorder. The orthodontic protraction headgear appliance creates discomfort to the chin and forehead of the wearer, and fosters other facial health issues during treatment of Class III Malocclusions. Commonly, there is head pain, jaw pain, teeth pain, cracked skin, redness, breakouts, lingering facial demarcations, suction marks, allergic reactions, pressure sores, decubitus sores, and other skin irritations, associated with wearing the orthodontic protraction headgear appliance during treatment, therefore the assuagement of discomfort to the chin, and to the forehead, and inhibition of the development of the aforementioned symptoms is imperative to the wearer. In addition, the orthodontic protraction headgear cover assembly, disclosed, described, and claimed, in the present invention, provides a portable, lightweight, flexible, soft cushiony, reusable, durable, resilient, machine washable, hygienic cover assembly which provides a soft cushiony absorbent membrane between the hard surface of the chin cup interface and the hard surface of the forehead pad interface and the orthodontic patient's chin and forehead, respectively, that provides pressure relief from the headgear interfaces upon the chin and the forehead; and provides an aerated cover which provides an air chamber which allows air to circulate throughin the space between the wearer's chin and chin cup interface; and which allows air to circulate throughin the wearer's forehead and the headgear forehead pad interface; and thereby provides a healthy hygienic environment that is beneficial to the wearer, such that microbial growth at the site of the wearer's chin and forehead is reduced or, otherwise, inhibited. Perspiration, mouth leaks, skin flora, skin oils, and other fluids may accumulate between the interface and the patient's skin while wearing the orthodontic headgear. The protective cover assembly is easily installed and removed, and which is machine washable, and thereby the patient can maintain good hygiene and a healthy environment around the patient's chin and forehead. In addition, the protective cover assembly is easily manufactured and inexpensive, and is removably, and therefore, when needed or desired, the protective cover assembly can be conveniently replaced without much expense to the wearer. While there are orthodontic protraction head gear appliances that provide treatment options for Class III Malocclusion, those appliances do not disclose a successful comfortable, machine washable, reusable, hygienic, decorative, cover solution for the chin cup interface and forehead interfaces of the headgear appliance. By providing a washable protective cover assembly, the patient is able to maintain a sanitary environment around the skin and forehead of the wearer while using the orthodontic protraction headgear appliance. In this respect, the orthodontic protraction headgear cover described herein departs from any present configuration in providing absorbency, cushioning, and comfort, both physically and perceptually, hygienically, decoratively, and inexpensively, and thereby abandonment of use of the orthodontic protraction headgear appliance is avoided, and compliance is improved dramatically.

A primary object of the present invention is to provide a protective cover assembly for an orthodontic protraction headgear chin cup interface, and a forehead pad interface of an orthodontic protraction headgear appliance, directed to a cover providing a membrane that provides more comfort to the patient wearing an orthodontic protraction headgear appliance; to provide a soft cushioning surface upon which the wearer's skin comes in contact with to assuage the discomfort experienced while wearing the orthodontic protraction headgear appliance; and a cover which prevents formation of cracked skin, redness, breakouts, lingering facial indentations, suction marks, pressure sores, decubitus sores, irritation, microbial infection, discomfort, allergic reactions, and other skin disorders, that arise as a result of a chin cup interface and forehead pad interface pressed against the wearer's chin and forehead, while wearing an orthodontic protraction headgear appliance during treatment of Class III Malocclusions disorder.

It is another object of the present invention to provide an absorbent protective cover assembly for a chin cup interface and a forehead pad interface of orthodontic protraction headgear appliance to provide an absorbing means to enable protection against deposits of saliva, mouth leaks, perspiration, mucous, and skin bacterial flora, within the space between the wearer's facial skin on the chin and the headgear chin cup interface and within the space between the wearer's facial skin on the forehead and the headgear forehead pad interface, without leaving indentations or marks on the wearer's chin or forehead.

It is another object of the present invention to provide a protective cover assembly with sufficient cushion that controllably distributes chin contact forces between the headgear chin cup interface and the wearer's chin; and similarly, it is an object of the present invention to provide a cover with sufficient cushion that controllably distributes forehead contact forces between the forehead pad interface and the wearer's forehead.

It is another object of the present invention to provide a protective cover assembly with sufficient flexibility and stretch capable of folding around the contours of the headgear chin cup interface of an orthodontic headgear appliance; and it is an object of the present invention to provide a cover with sufficient flexibility and stretch capable of folding around the contours of the headgear forehead pad interface of an orthodontic protraction headgear appliance.

It is another object of the present invention to provide a protective cover assembly that is installed around the a chin cup interface of an orthodontic protraction headgear appliance and is secured by means of fastening means, preferably buttons; and it is an object of the present invention to provide a protective forehead pad cover that is installed around a forehead pad interface of an orthodontic protraction headgear appliance and is secured by means of fastening means, preferably buttons.

It is another object of the present invention to provide a protective cover assembly that is installed around a chin cup interface of an orthodontic protraction headgear appliance and is secured by means of fastening means, buttons, or hook and loop fasteners, hook and eyes, snaps, or VELCRO®; and it is another object of the present invention to provide a protective cover assembly that is installed around a forehead pad interface of an orthodontic protraction headgear appliance and is secured by means of fastening means, buttons, or hook and loop fasteners, hook and eyes, snaps, or VELCRO®.

It is another object of the present invention to provide a protective cover assembly that conforms to the contour of a chin cup interface; and a protective cover assembly that conforms to a forehead pad interface of an orthodontic protraction headgear appliance so as not to compromise the forces imputed through a orthodontic protraction headgear appliance and the stabilizing capabilities of the chin cup interface and the forehead pad interface.

It is another object of the present invention to provide a protective cover assembly which provides additional layered padding providing enhanced comfort and creating a membrane between the wearer's chin and the rigid hard surface of a chin cup interface; and to provide a protective cover assembly which provides additional padding providing enhanced comfort and creating a membrane between the wearer's forehead and the rigid hard surface of a forehead pad interface.

It is another object of the present invention to provide a protective cover assembly that provides a hygienic membrane between the wearer's chin and a chin cup interface; and a hygienic membrane between the wearer's forehead and the orthodontic protraction headgear forehead pad interface.

It is another object of the present invention to provide a protective cover assembly that is easily installed and removed and that it is submersible and washable, allowing it to be maintained in a clean and sanitary condition.

It is an object of the present invention to provide a protective cover assembly that displays buttons in a prominent manner that mimics a face when a cover is installed onto the chin cup interface; and when a protective cover assembly is installed upon a forehead pad interface of the orthodontic protraction headgear appliance.

It is another object of the present invention to provide an upgraded protective chin cup cover assembly and upgraded protective forehead pad cover assembly which is of a predetermined thickness which enables a more secure aerated seal between the patient's chin and a chin cup interface, and which enables a more secure seal between the patient's forehead and a forehead pad interface.

It is another object of the present invention to provide a decorative covering for a chin cup interface and forehead pad interface as a means to conceal the harsh medicinal appearance of an orthodontic protraction headgear appliance and thereby provide a decorative cover assembly for a chin cup interface and for a forehead pad interface with colored soft fleece material and decorative buttons.

It is another object of the present invention to provide a protective cover assembly for an orthodontic protraction headgear appliance chin cup interface; and a protective cover assembly for a forehead pad interface which is versatile and can be changed easily because of need or if desired by the wearer. When the covers become soiled they can be easily removed and washed and then easily reaffixed to the headgear. In addition, if the patient desires a different color or different buttons on the headgear cover the covers can easily be changed and personalized.

It is another object of the present invention to provide a protective cover assembly for orthodontic protraction headgear chin cup interface, and a protective cover assembly for a forehead pad interface which prolongs the life of an orthodontic protraction headgear appliance, and thereby prolonging the life of the headgear appliance curtails the necessity to replace the orthodontic protraction headgear appliance saving costs for the patient, as well as, avoiding a gap in the treatment time due to waiting for a new orthodontic protraction headgear appliance, or replacement chin cup interface, or replacement headgear pad interface.

It is another object of the present invention to provide a protective cover assembly for orthodontic protraction headgear chin cup interface, and forehead pad interface, which is economical to manufacture and requires small amounts of fleece material and fastening devices.

It is another object of the present invention to provide a protective cover assembly for orthodontic protraction headgear chin cup interface, and forehead pad interface, which can be manufactured from recycled products which produce fleece fabric.

It is another object of the present invention to provide a soft absorbent cushioning protective cover assembly for orthodontic protraction headgear chin cup interface, and forehead pad interface, which protects the hard material of a chin cup interface and hard material of a forehead pad from normal wear and tear, soiling, discoloring, caused by rubbing against the wearer's skin oils, perspiration, skin flora, mucous, and other contaminants that are present on the wearer's chin or forehead.

It is another object of the present invention to provide a soft absorbent cushioning protective cover assembly for an orthodontic protraction headgear chin cup interface, and a forehead pad interface, as a means to enable the wearer not to abandon use of the headgear appliance and thereby enable the wearer to successfully complete treatment for Class III Malocclusion disorder.

It is another object of the present invention to provide a protective cover assembly which provides a membrane between the wearer's skin on the chin and underlying tissue so as to prevent engagement of the hard surface of the external orthodontic protraction chin cup interface pressing in direct contact against the wearer's skin of the chin; and to provide a membrane between the wearer's skin of the forehead and underlying tissue so as to prevent engagement of the hard surface of the external orthodontic protraction forehead pad interface pressing in direct contact with the wearer's skin of the forehead.

It is another object of the present invention to provide a protective cover assembly with a pleat that is open ended to provide for better circulation of air, ability to wash and dry outer and inner surfaces of the protective chin cup cover more efficiently.

It is another object of the present invention to provide a protective cover assembly including an aperture wherein an orthodontic protraction vertical main frame can be inserted throughin.

It is another object of the present invention to provide a protective cover assembly including a dart cut-out wherein a screw located on an orthodontic protraction headgear appliance can be passed therein.

It is another object of the present invention to provide a protective cover assembly for orthodontic protraction headgear appliance chin cup interface, and forehead pad interface wherein the fastening means are buttons and may assume a plurality of configurations and designs that project the design of a face.

It is another object of the present invention to provide a protective cover assembly which can be modified for a plurality of orthodontic headgear appliance interfaces having different geometries.

In addition, social, occupational, school participation, sport participation and emotional functioning have been incorporated into the present invention which relate to patient self-image, confidence, personal style, and humorous design which consequently improves overall comfort and compliance of use of the orthodontic protraction headgear appliance.

The creation of this present invention and its reduction to practice was inspired by a mother of an orthodontic patient with Class III Malocclusion disorder. The patient, and fellow patients, were experiencing discomforts associated with treatment and use of the orthodontic protraction headgear appliance, particularly, skin irritation, breakouts, and infection on the site of the patient's chin and forehead and the development of pressure sores aggravated by mucous, saliva, mouth leaks, especially while sleeping, and harboring of skin microbial flora and opportunistic contaminants. Avoidance of wearing the orthodontic protraction headgear appliance, while compassionately understood and justified, was delaying successful treatment of the orthodontic patient. Upon use of the novel, non-obvious, and useful, protective chin cup cover assembly, and protective forehead pad cover assembly, with an orthodontic protraction headgear appliance, discomforts associated with its use were eliminated and abandonment of use of the orthodontic appliance was remarkably reduced, and therefore compliance was increased.

Therefore, it is highly desirable for orthodontists, and parents of patients with Class III Malocclusion undergoing treatment, to provide these patients with the present invention, a protective chin cup cover assembly, and a protective forehead pad cover assembly, to install upon a chin cup interface and forehead pad interface of an orthodontic protraction interface appliance, in order for the patient to improve the control and management of the treatment.

Notably, the present invention has experienced requests by patients and orthodontic physicians for use. A need therefore exists for this novel, useful, non-obvious invention for use with orthodontic protraction headgear appliances by patients with Class III Malocclusion to assuage the discomforts and health issues associated with its use and to promote successful treatment. A need exists for a protective cover assembly that reduces the formation of cracked skin, breakouts, allergic reactions, lingering facial indentations, suction, marks, contact pressure sores, decubitus sores, microbial infection, and other skin disorders, acting on the chin and forehead of patients and at the same time does not diminish or inhibit the effectiveness of the orthodontic protraction headgear appliance in the treatment of Class III Malocclusion disorder. Therefore, protective cover assembly prolongs the use of an orthodontic protraction appliance, enables compliance by orthodontic patients and thereby advances their successful treatment. A reliable soft, absorbent, cushiony, breathable, removable protective cover assembly for an orthodontic protraction headgear chin cup interface, and forehead pad interface, would be an invaluable improvement to an orthodontic protraction headgear appliance and provide comfort to the orthodontic patient, and consequentially provide for increased compliance of patients wearing the orthodontic protraction headgear appliance which would improve the outcome of successful treatment of Class III Malocclusion patients.

The need is met by the present invention as described and claimed below. These and other objects of the invention will be best understood when reference is made to the Brief Description of the Drawings, and Detailed Description of the Invention, which follows hereinbelow.

BRIEF DESCRIPTION

Figure 7:
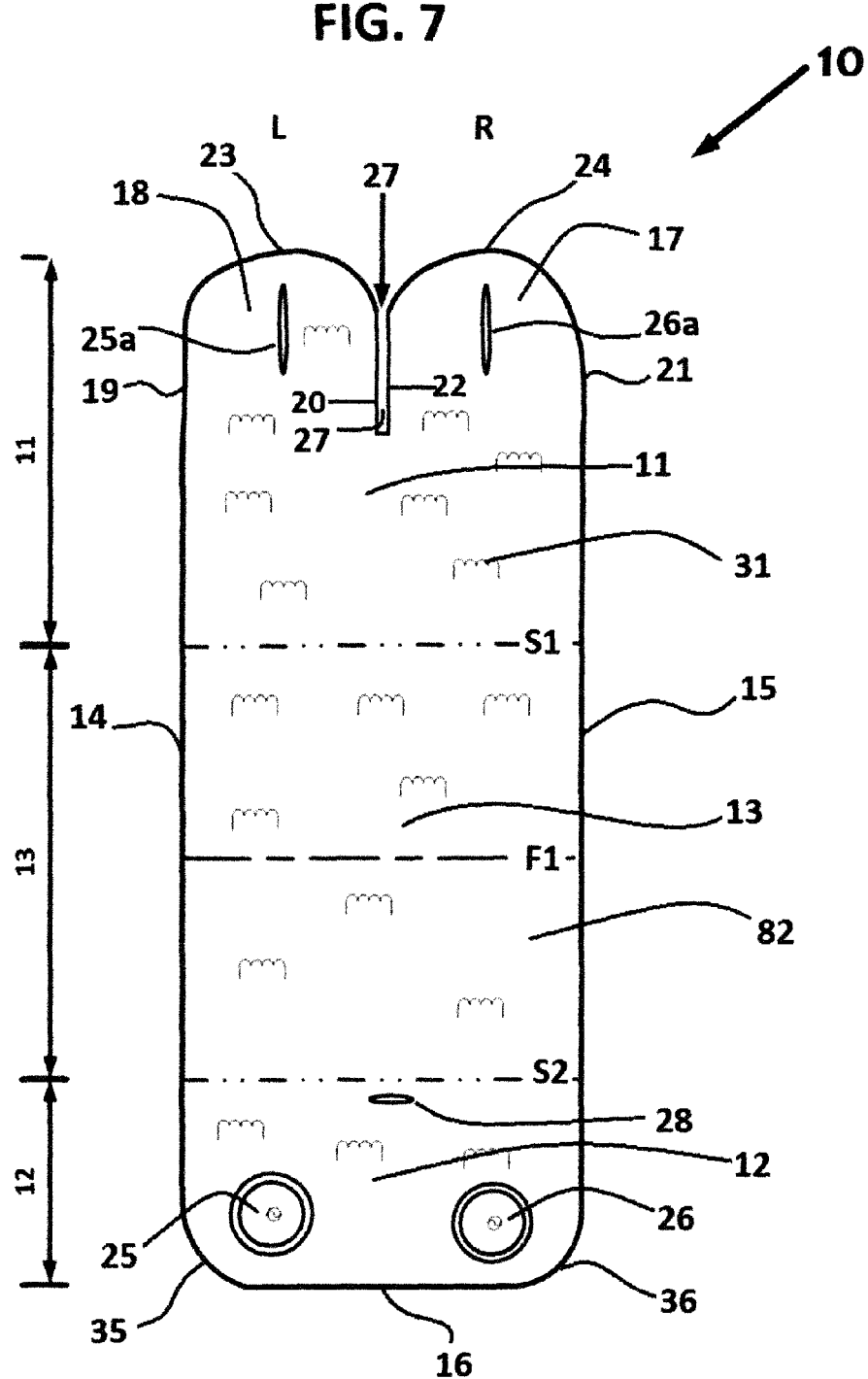

FIG. 7 illustrates a top plan view of an exemplary protective chin cup cover assembly 10, according to the preferred embodiment of the present invention, which is shown in its flat, unpleated state, before the pleat 84 is formed, and the obverse soft side 31 of the fleece material 82, and two buttons 25 and 26, are facing up towards the viewer.

Figure 8:
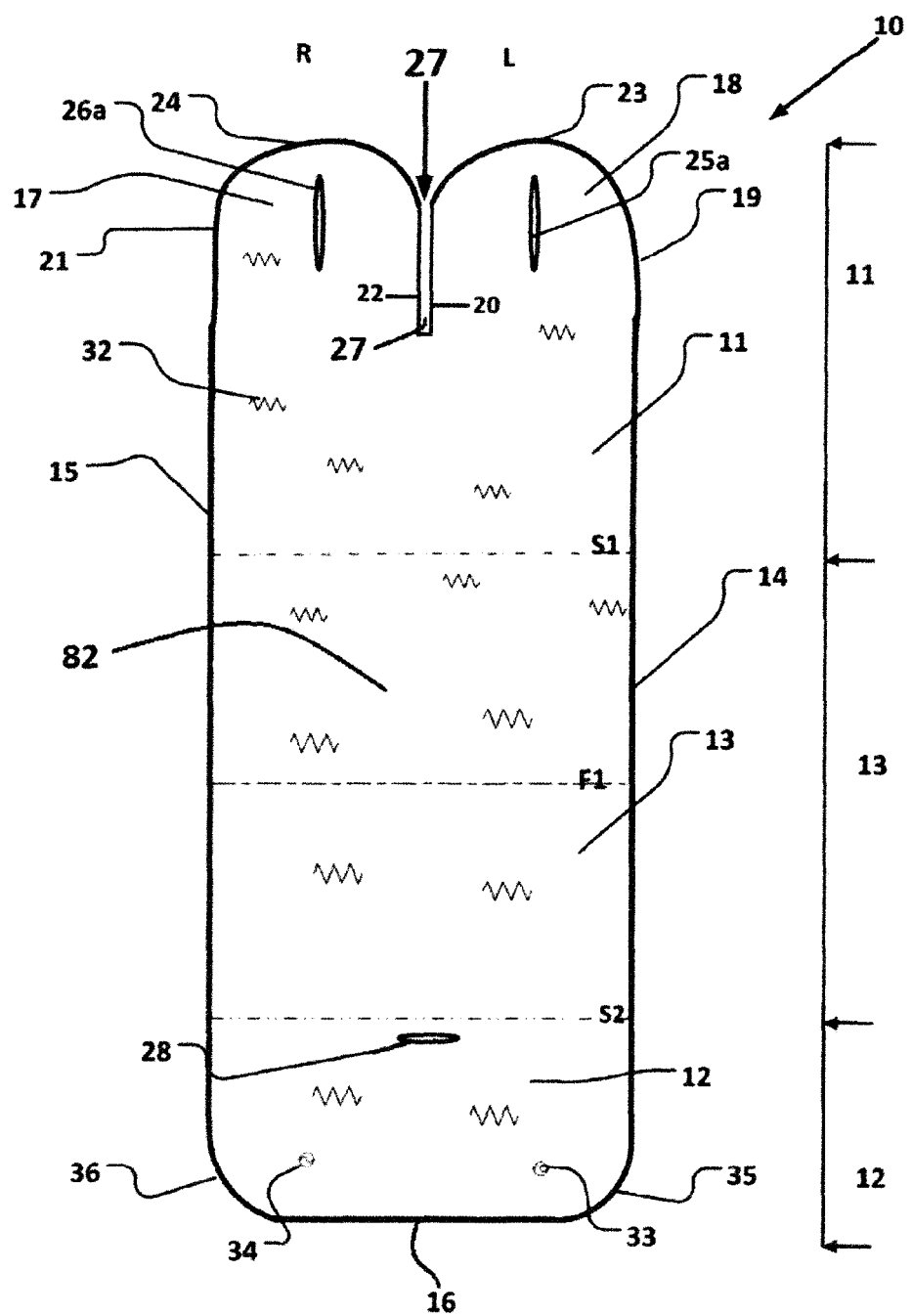

FIG. 8 illustrates a top plan view of the reverse side of FIG. 7, according to the preferred embodiment of the present invention, which is the chin cup cover assembly 10 its flat, unpleated state, before the pleat 84 is formed, showing the dull surface side 32 of the fleece material 82, and back side of affixed buttons 34 and 33.

Figure 9:
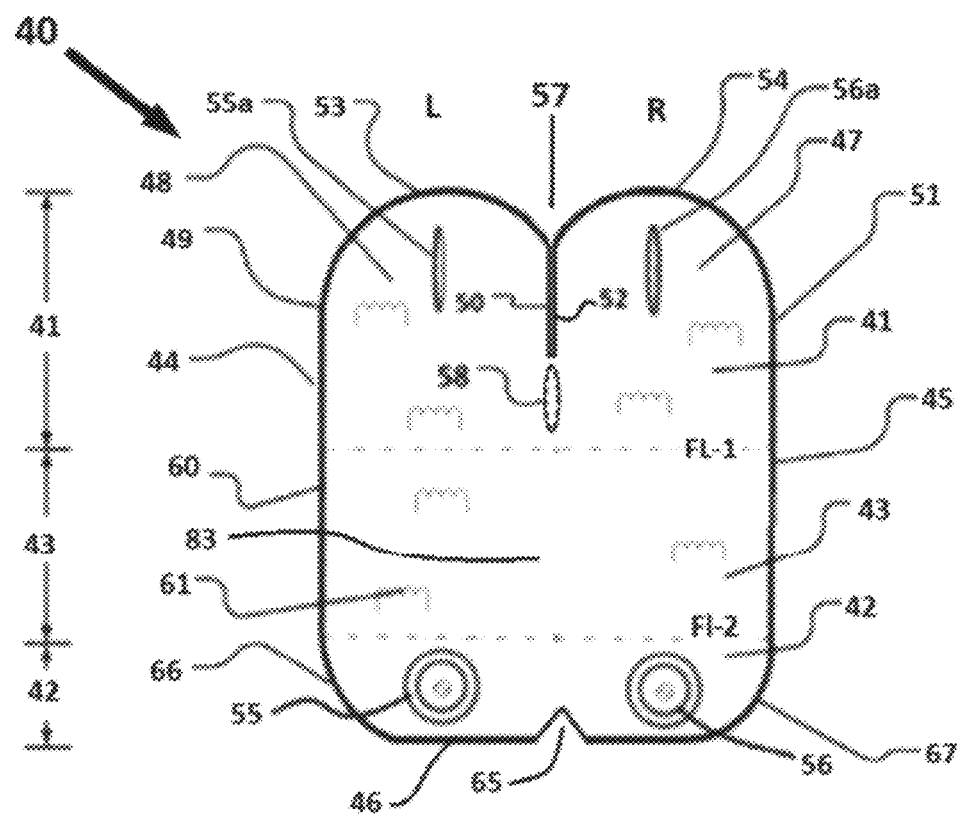

FIG. 9 illustrates a top plan view of a protective forehead pad cover assembly 40, according to the preferred embodiment of the present invention, which is shown in its flat, unfolded state, i.e., before it is installed onto a forehead pad interface of an orthodontic protraction headgear appliance, where the obverse soft side 61 fleece surface 83, and two buttons 55 and 56, are facing up towards a viewer.

Figure 10:
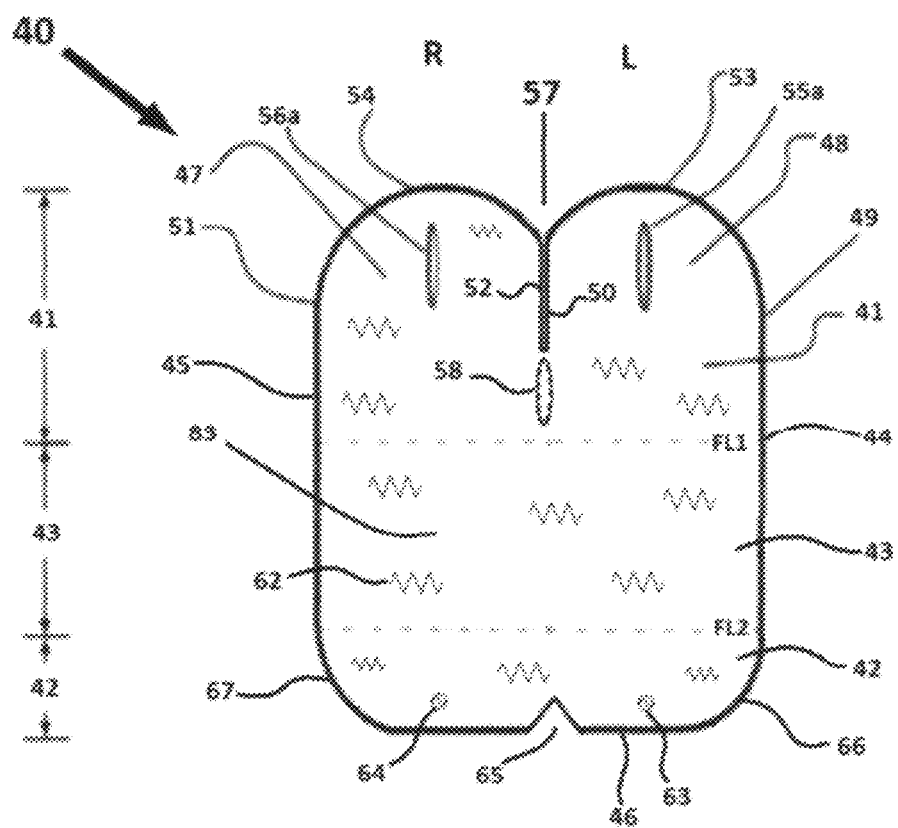

FIG. 10 illustrates a top plan view of the reverse side of an exemplary protective forehead pad cover 40 assembly of FIG. 9, according to the preferred embodiment of the present invention, showing the dull surface side 62 up facing up towards a viewer, and the back side of the affixed buttons 64 and 63.

Figure 11:
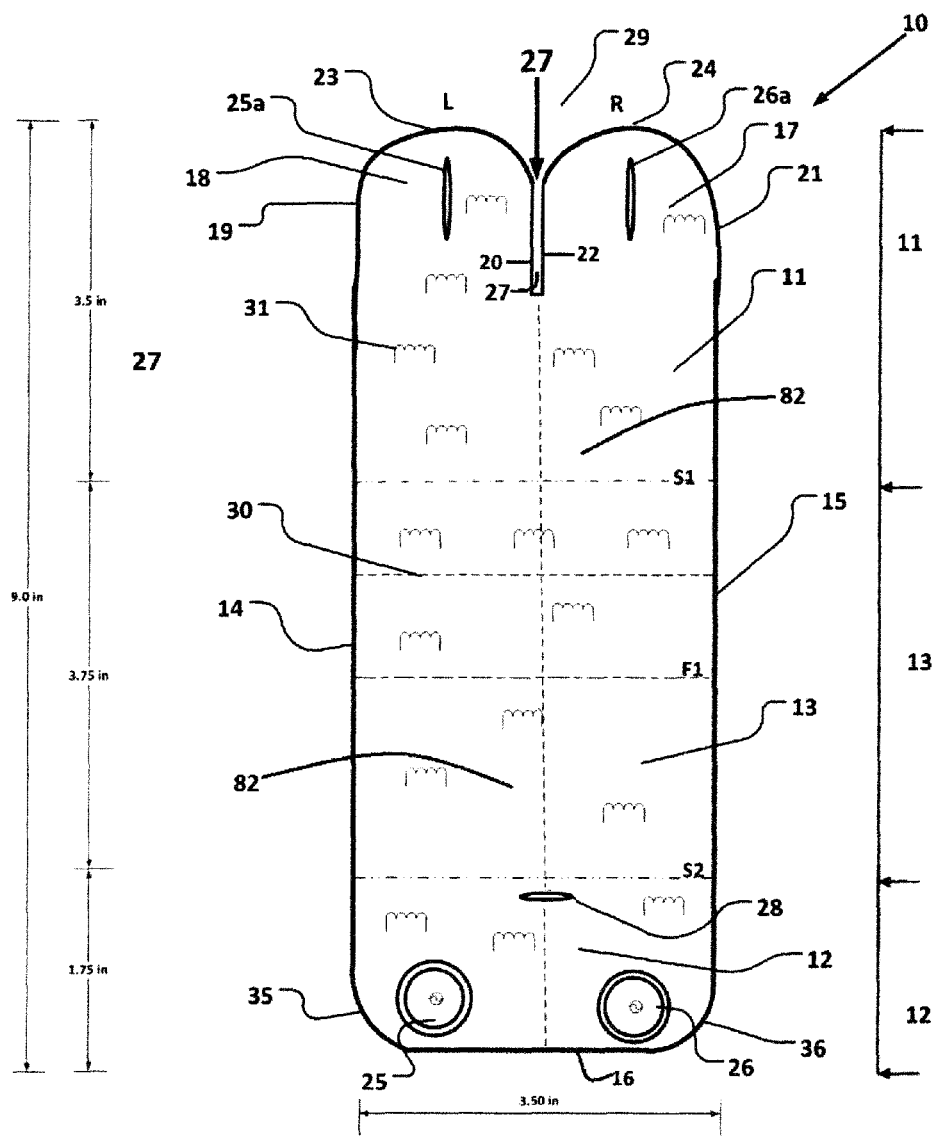

FIG. 11 illustrates a top plan view of the preferred embodiment of a protective chin cup cover assembly 10, according to the preferred embodiment of the present invention, illustrating the dimensions of the chin cup cover assembly 10 to illustrate a pattern and method of making a protective chin cup cover assembly 10, with fold line F1 and seam lines S1 and S2, and longitudinal axis 29, and lateral axis 30, and soft side 31 of the chin cup cover assembly 10, and two buttons 25 and 26, facing up towards a viewer.

Figure 12:
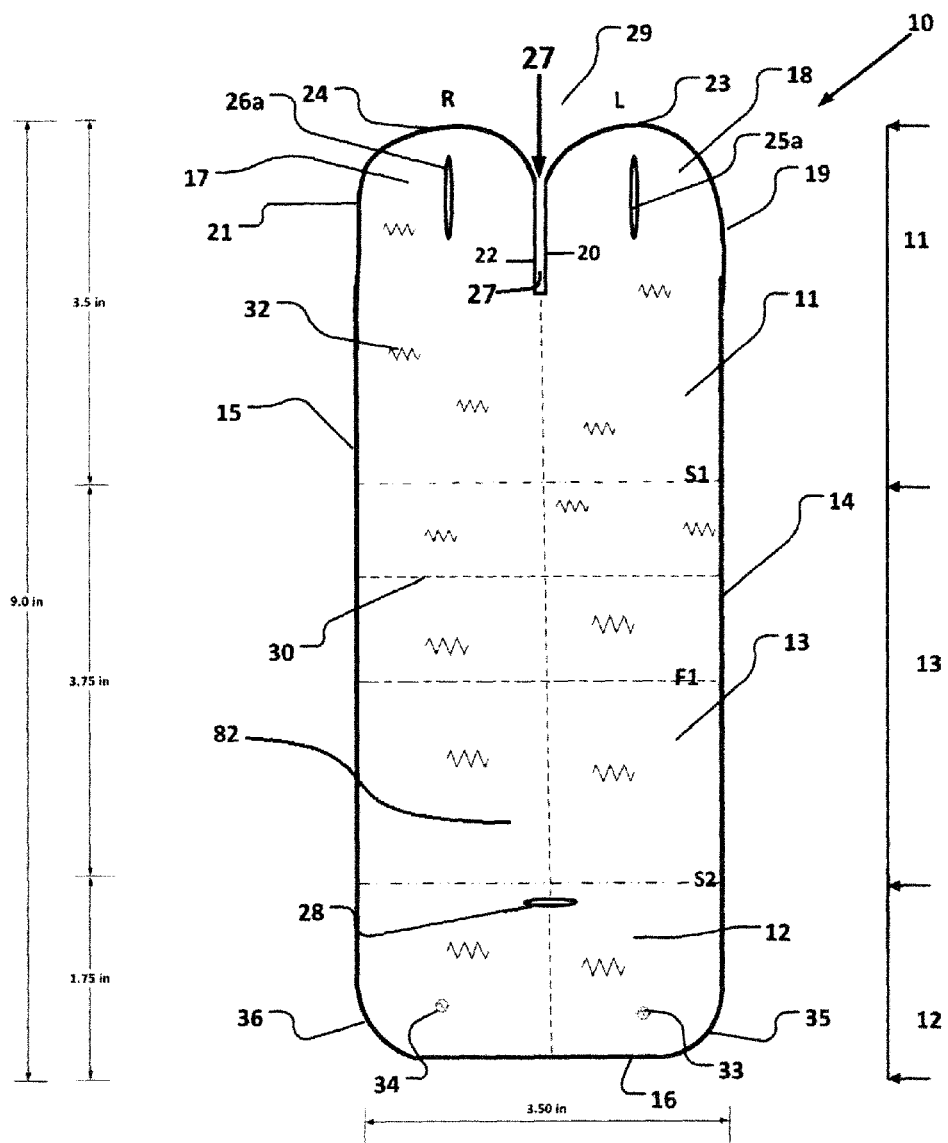

FIG. 12 illustrates a top plan view, according to the preferred embodiment of the present invention, showing reverse side of a protective chin cup cover assembly 10 as illustrated in FIG. 11, illustrating the dimensions of the chin cup cover assembly 10 to illustrate a pattern and method of making of a protective chin cup cover assembly 10, with fold line F1 and seam lines S1 and S2, and longitudinal axis 29, and lateral axis 30, and showing the reverse dull side 32 of the chin cup cover assembly 10, and back side of affixed buttons 34 and 33, facing up towards a viewer.

Figure 13:
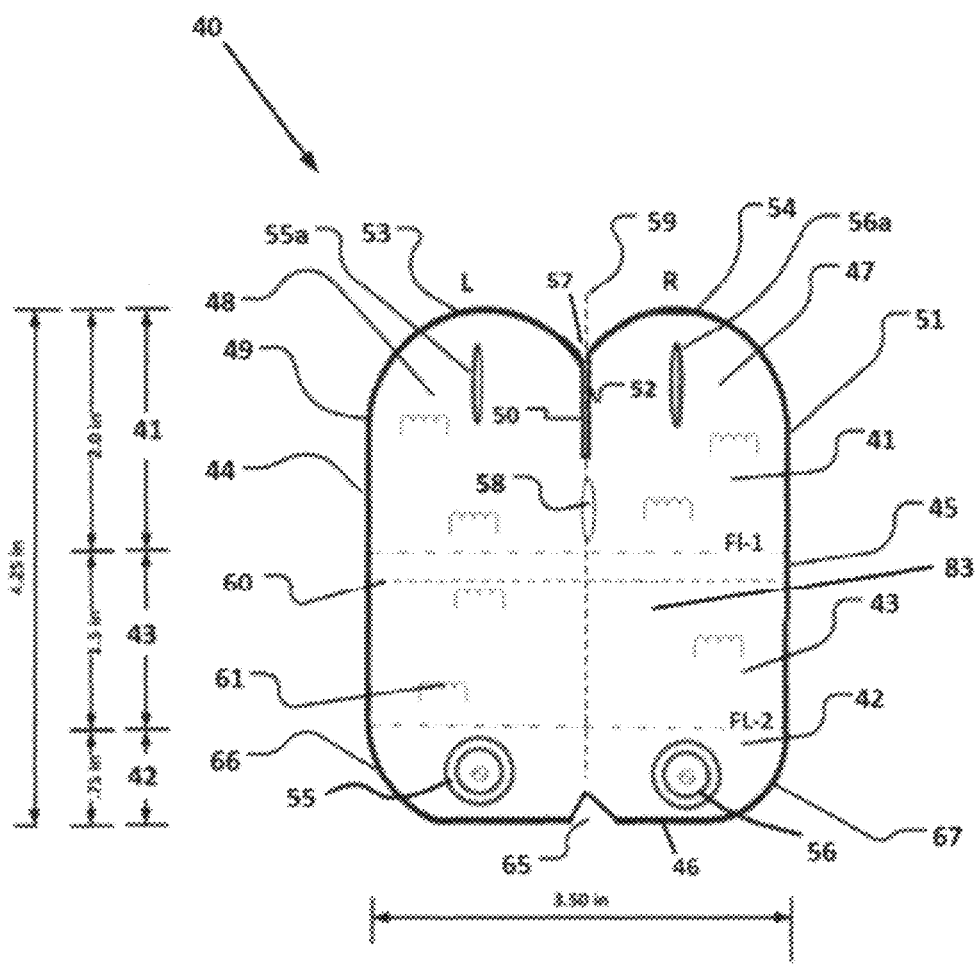

FIG. 13 illustrates a top plan view of the preferred embodiment of a protective forehead pad cover assembly 40, according to the preferred embodiment of the present invention, illustrating the dimensions of a forehead pad cover assembly 40 to illustrate a pattern and method of making a forehead pad cover assembly 40, with fold line F1 and seam lines S1 and S2, and longitudinal axis 59, and lateral axis 60, and showing the obverse soft side 61 of the forehead pad cover 40, and two buttons 55 and 56, facing up towards a viewer.

Figure 14:
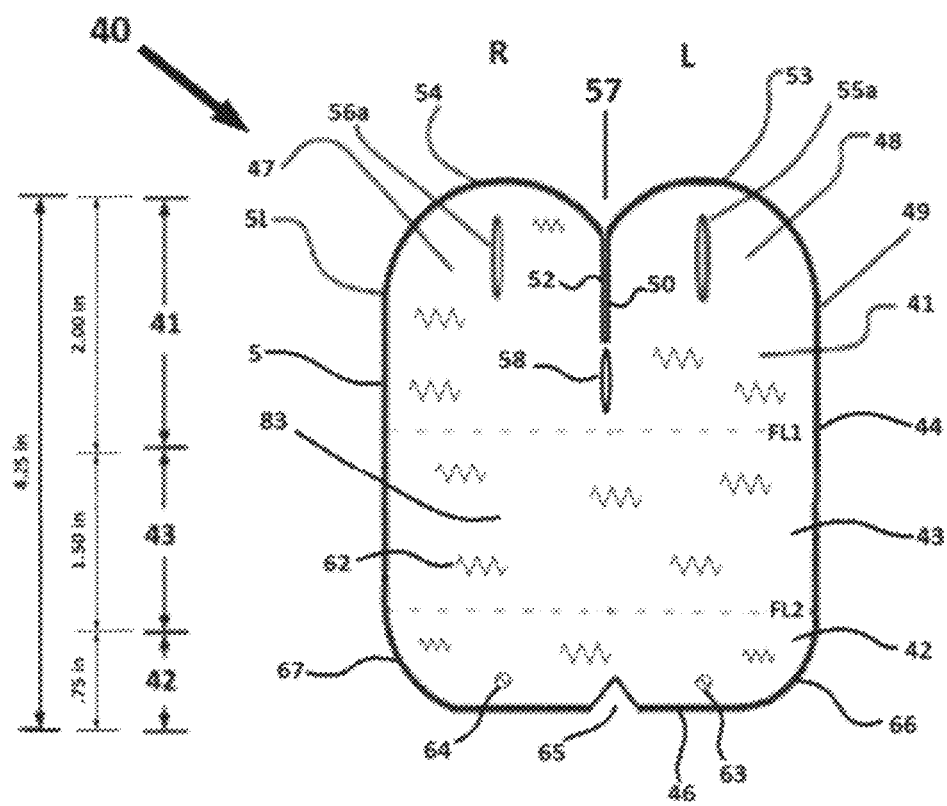

FIG. 14 illustrates a top plan view of the reverse side of a protective forehead pad cover assembly 40 as illustrated in FIG. 13, according to the preferred embodiment of the present invention, illustrating the dimensions of a forehead pad cover assembly 40 to illustrate a pattern and method of making a forehead pad cover assembly 40, with fold line F1, and seam lines S1 and S2, longitudinal axis 59, lateral axis 60, and showing the reverse dull side 62 and back side of affixed buttons 64 and 63.

Figure 15:
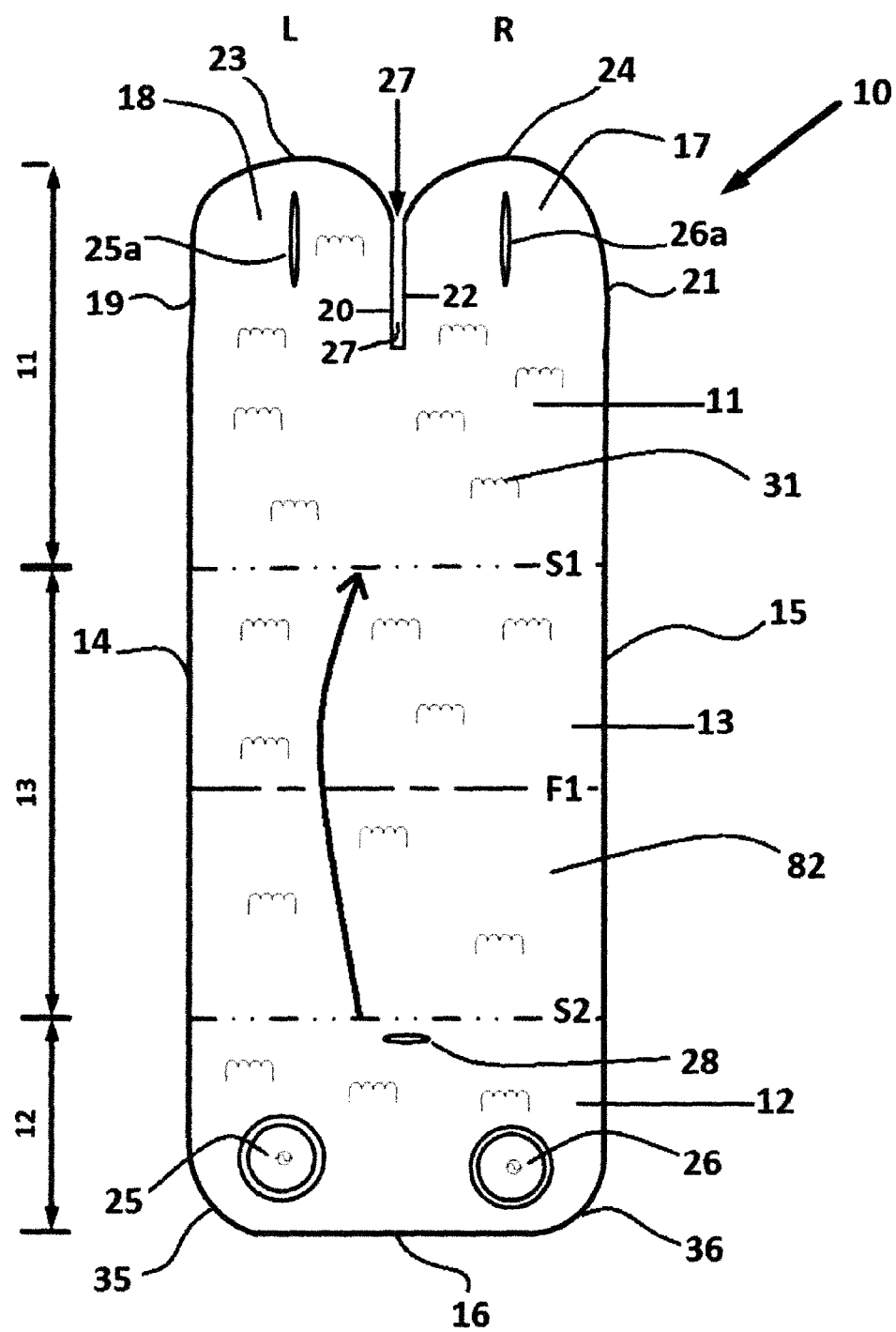

FIG. 15 illustrates a top plan view of a protective chin cup cover assembly 10 with the soft obverse side 31 facing up, illustrating first step in the method of formation of a pleat 84 at the chassis core portion 13, according to the preferred embodiment of the present invention.

Figure 16:
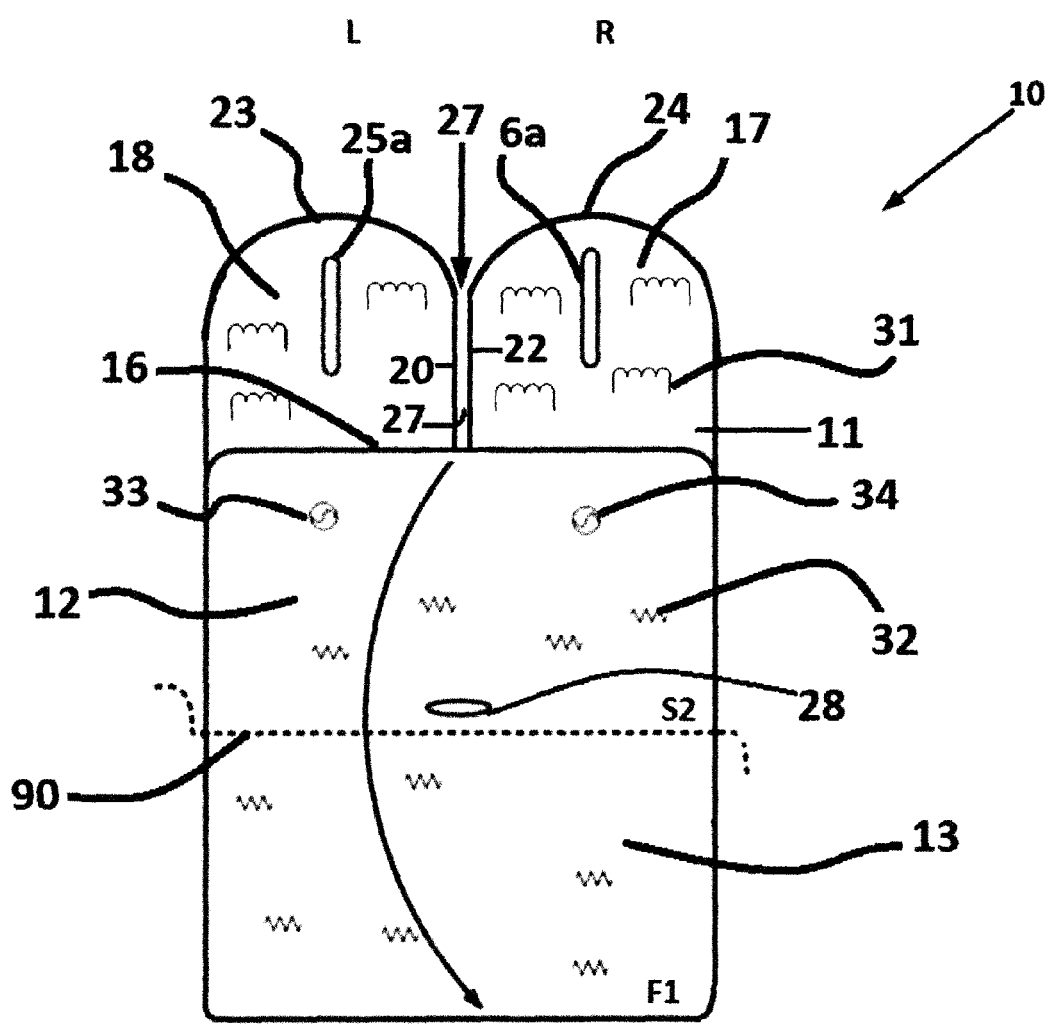

FIG. 16 illustrates a top plan view of a protective chin cup cover assembly 10 illustrating second step in the method of formation of a pleat 84 at the chassis core portion 13, according to the preferred embodiment of the present invention.

Figure 17:
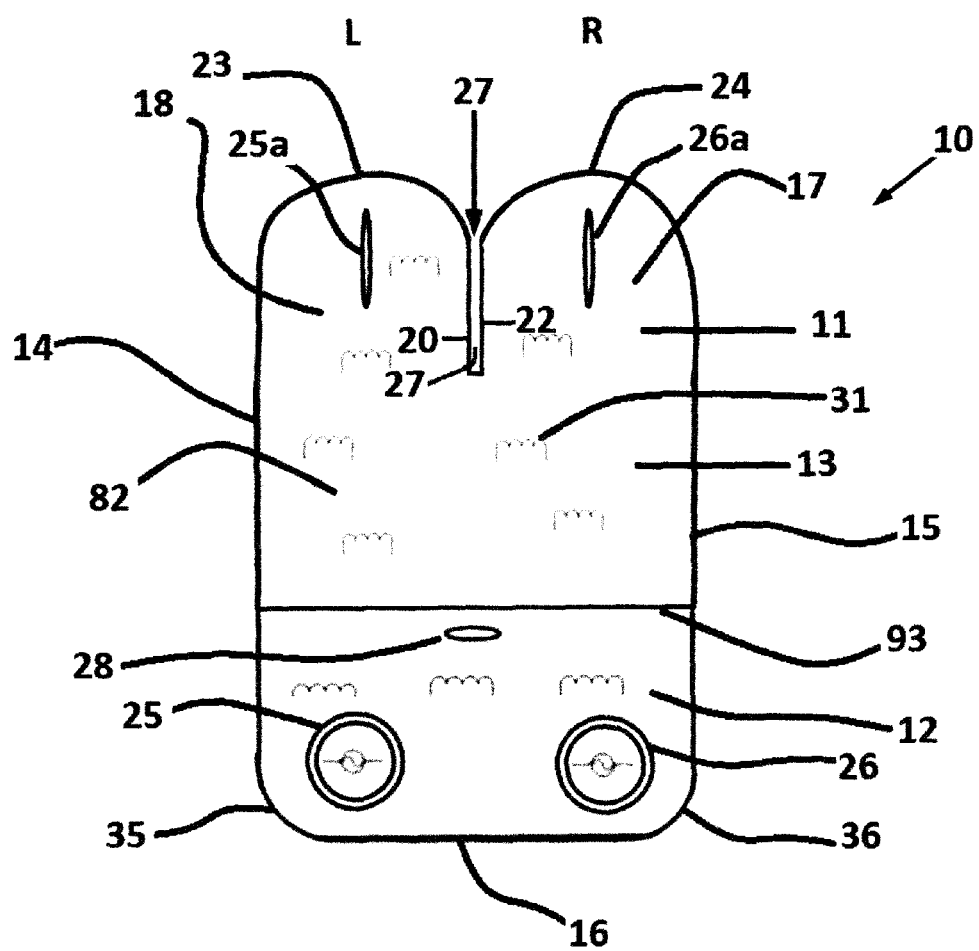
Figure 18:
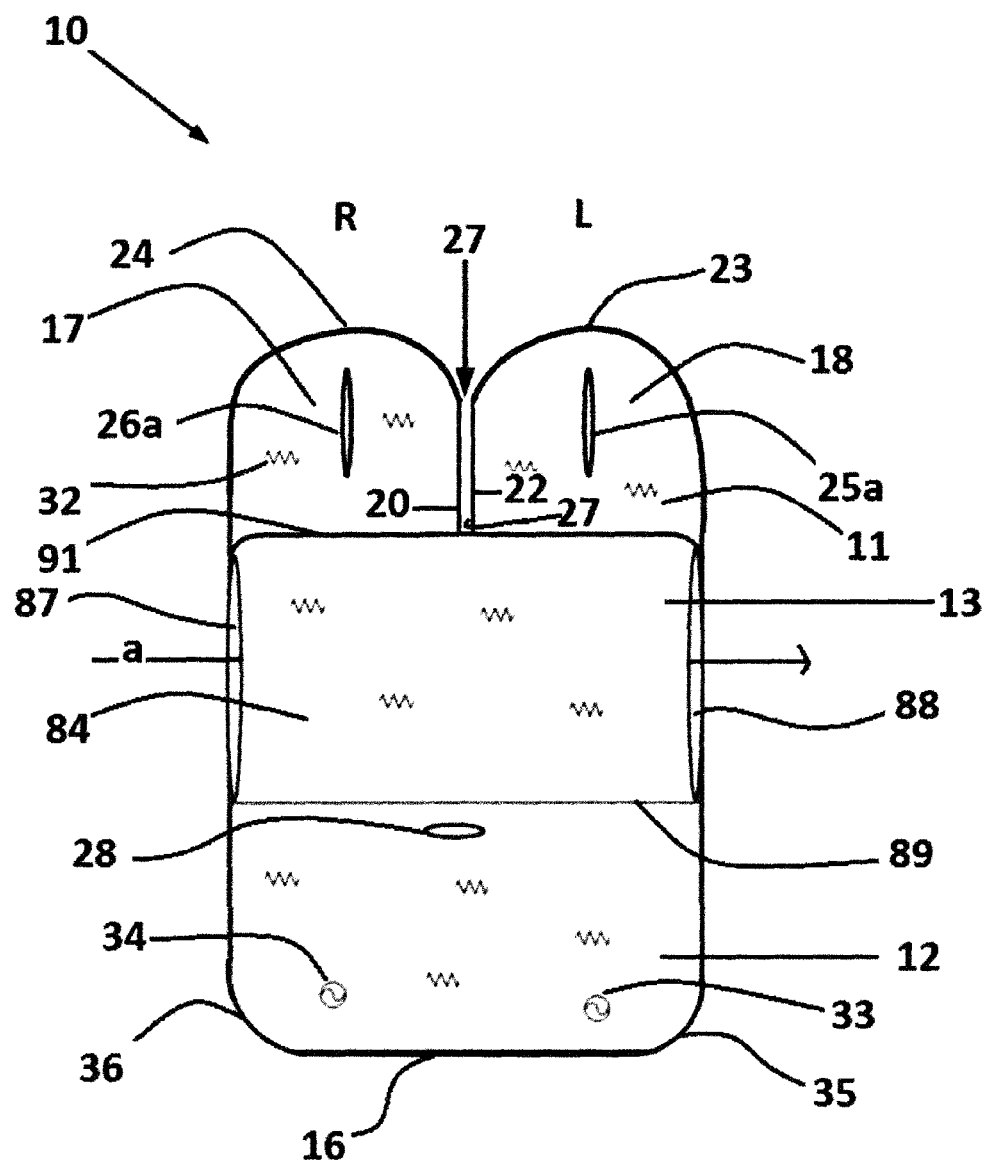

FIG. 17 illustrates a top plan view of a protective chin cup cover assembly 10, with the soft obverse side 31 facing up, so that pleat 84 is on reverse side at the chassis core portion 13, as illustrated in FIG. 18, according to the preferred embodiment of the present invention.

FIG. 18 illustrates a top plan view of the reverse side of a protective chin cup assembly 10 as illustrated in FIG. 17, illustrating a pleat 84 affixed upon the chassis core portion of a chin cup cover assembly 10 having open lateral edges as illustrated by arrow a, according to the preferred embodiment of the present invention.

Figure 19:
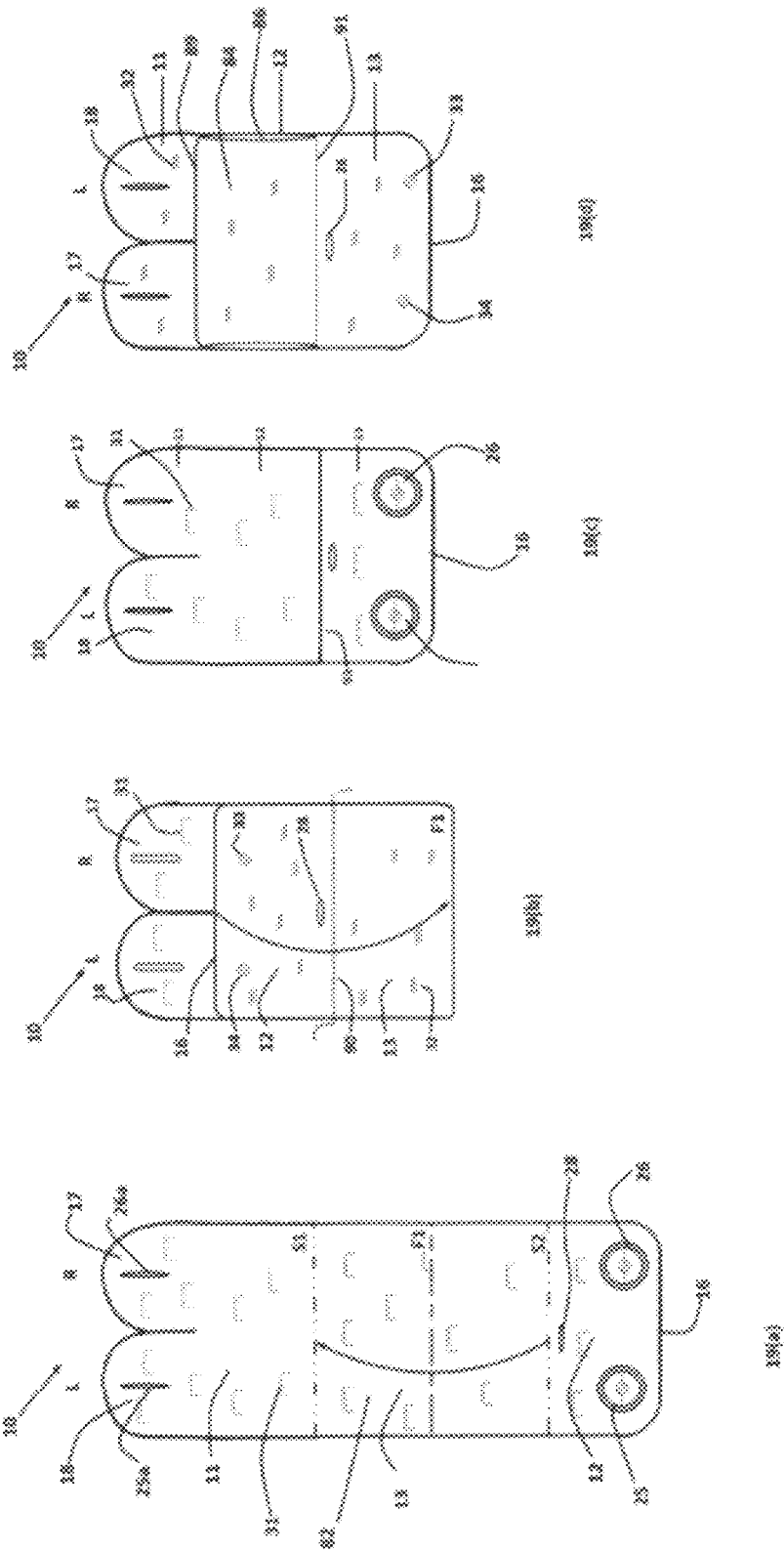

FIG. 19($a$)-($d$) illustrates steps of the method of making a pleat 84 with the fleece material within the chassis core portion 13 of the chin cup cover assembly 10, according to the preferred embodiment of the present invention.

FIG. 20($a$)-($c$) illustrates a side perspective view illustrating the formation of a pleat 84, according to the preferred embodiment of the present invention.

Figure 21:
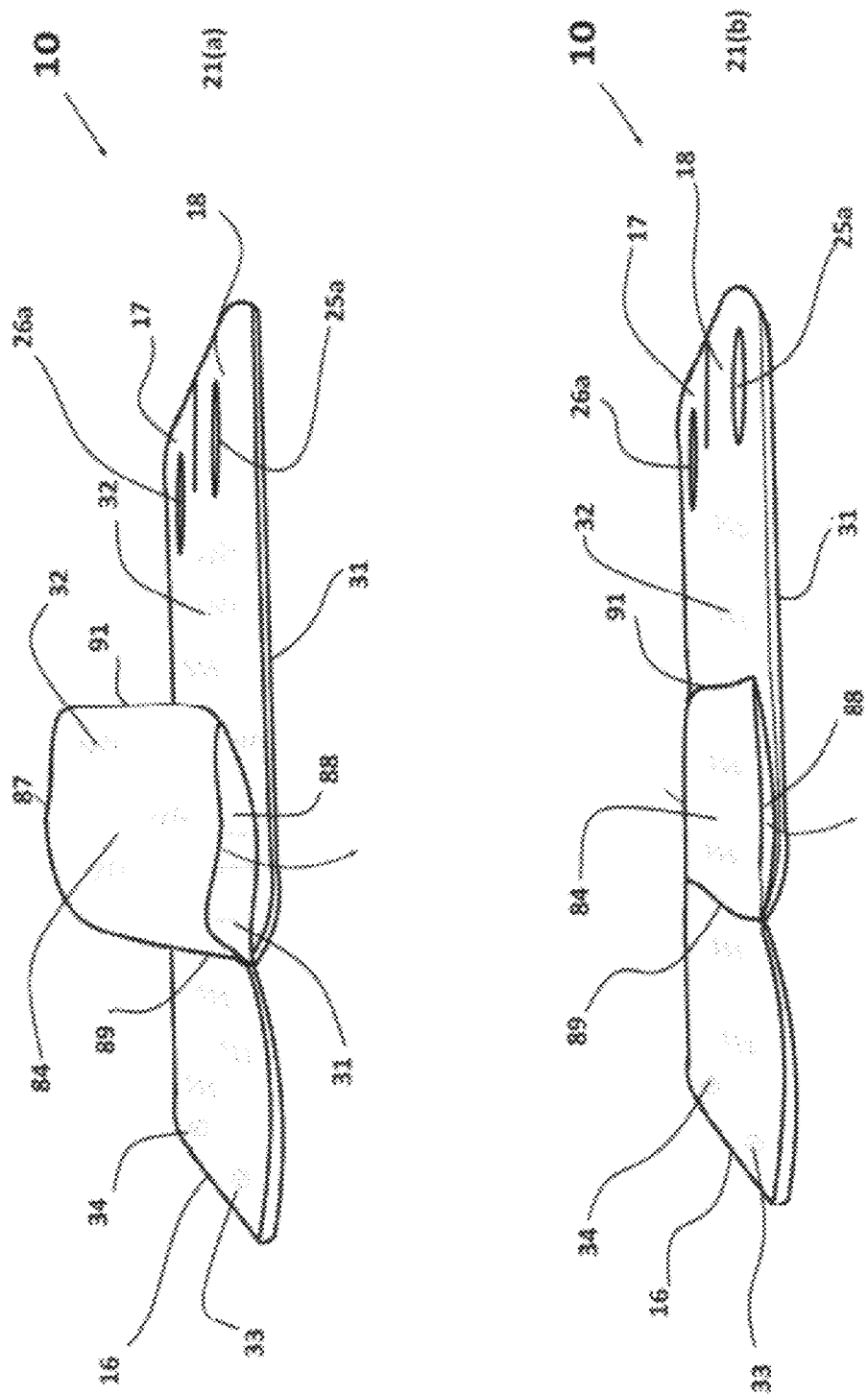

FIG. 21($a$)-($b$) illustrates a side perspective view illustrating a two layered pleat 84 at the chassis core portion of a chin cup cover assembly 10 illustrating the open lateral side edges of the pleat 87 and 88; 21($b$) illustrates a side perspective view of the pleat 84 forming three layered membrane at the chassis core portion 13 on the reverse dull side 32 of the chin cup cover assembly 10, according to the preferred embodiment of the present invention.

Figure 22:
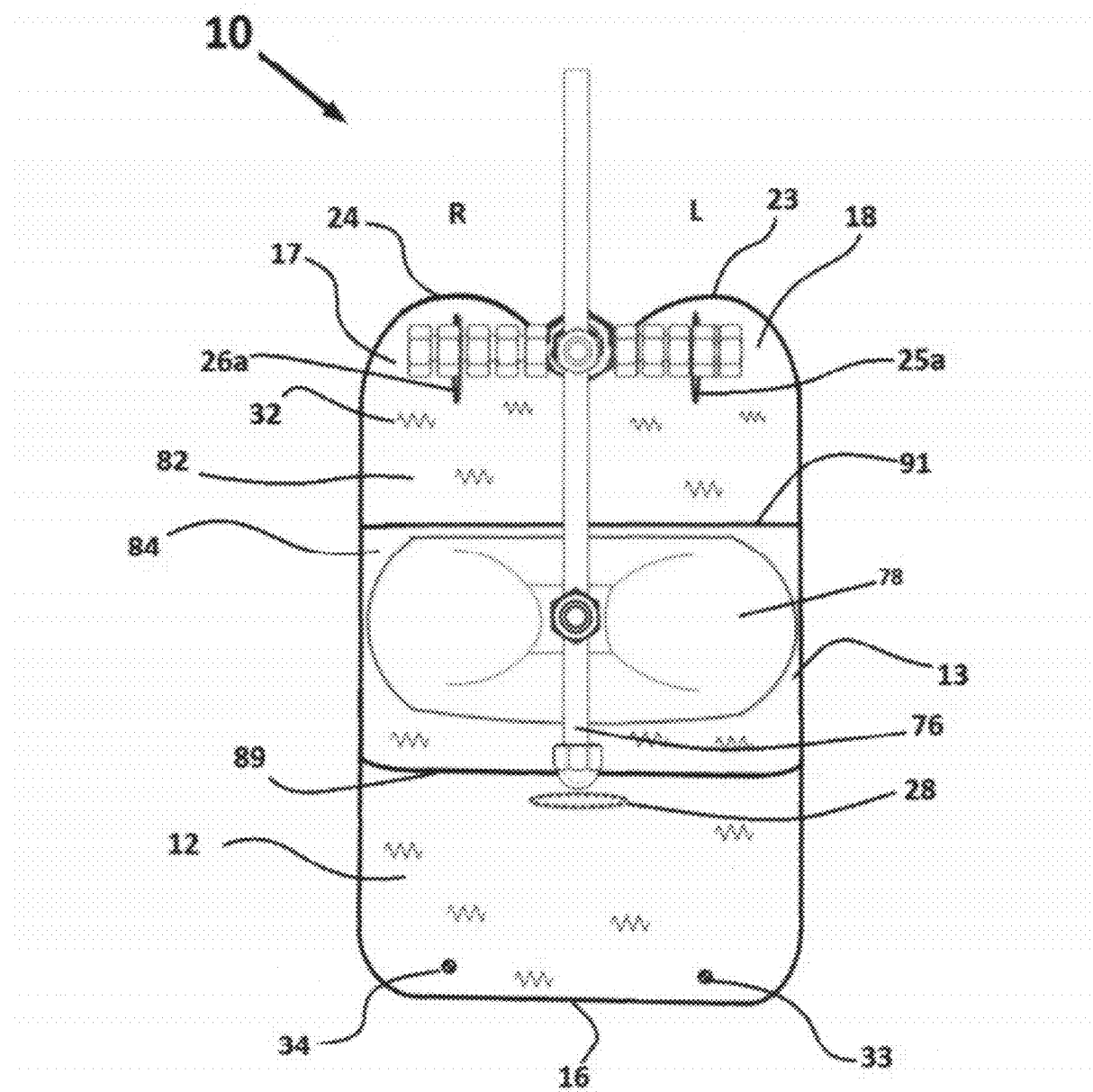

FIG. 22 illustrates a perspective view of a protective chin cup cover assembly 10 maneuvered for installation upon an external chin cup interface member of an external orthodontic protraction headgear appliance, according to the preferred embodiment of the present invention, showing the reverse side 32 of the chin cup cover assembly 10 with pleat 84 positioned behind an external chin cup interface member pivotally positioned to insert the bottom end of the main frame of the appliance into the horizontal aperture 28 of the protective chin cup cover assembly 10.

Figure 23:
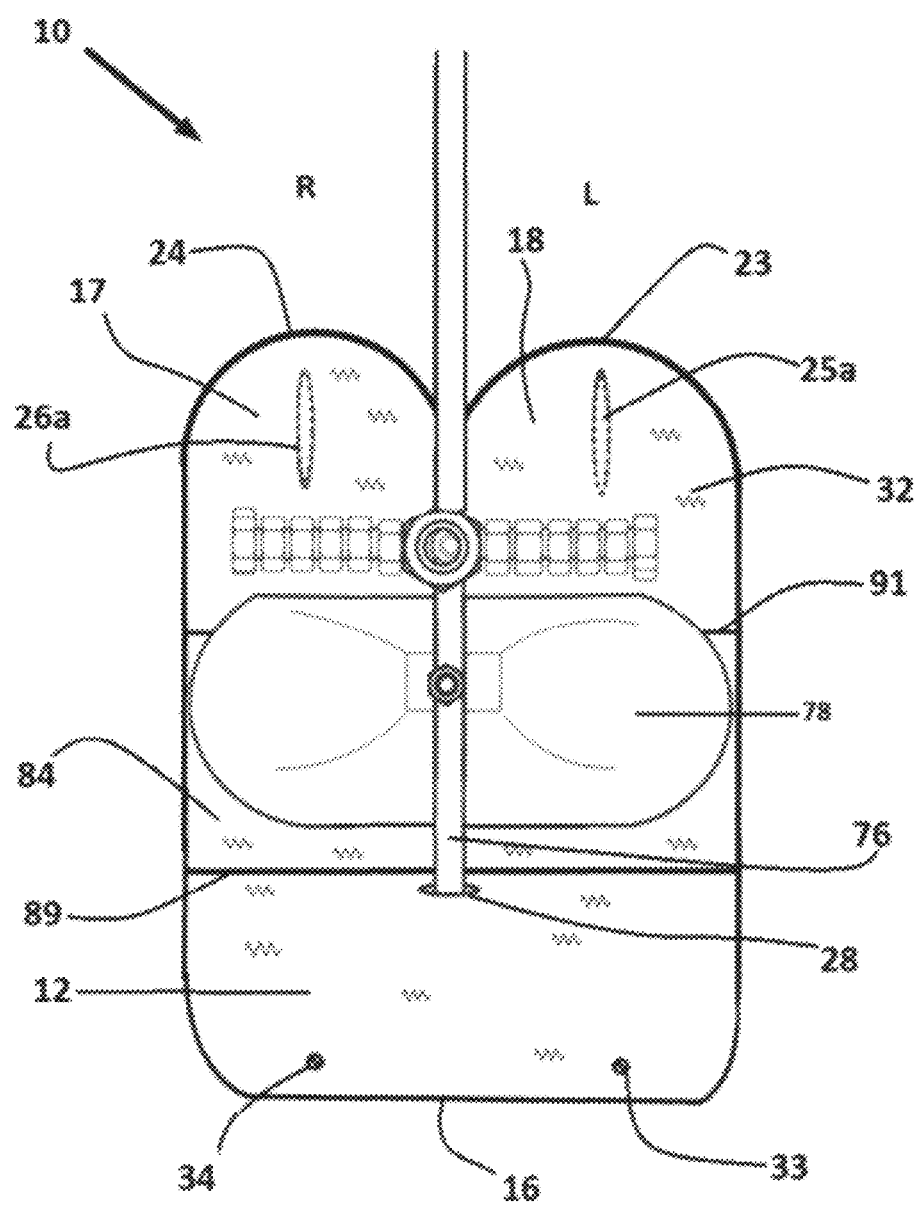

FIG. 23 illustrates a perspective view of a protective chin cup cover assembly 10 maneuvered for installation upon an external chin cup interface member of an external orthodontic protraction headgear appliance, according to the preferred embodiment of the present invention, showing the reverse side 32 of the chin cup cover assembly 10 with pleat 84 positioned behind an external chin cup interface member and bottom end of the vertical main frame of the appliance inserted throughin the horizontal aperture 28 of the protective chin cup cover assembly 10.

Figure 24:
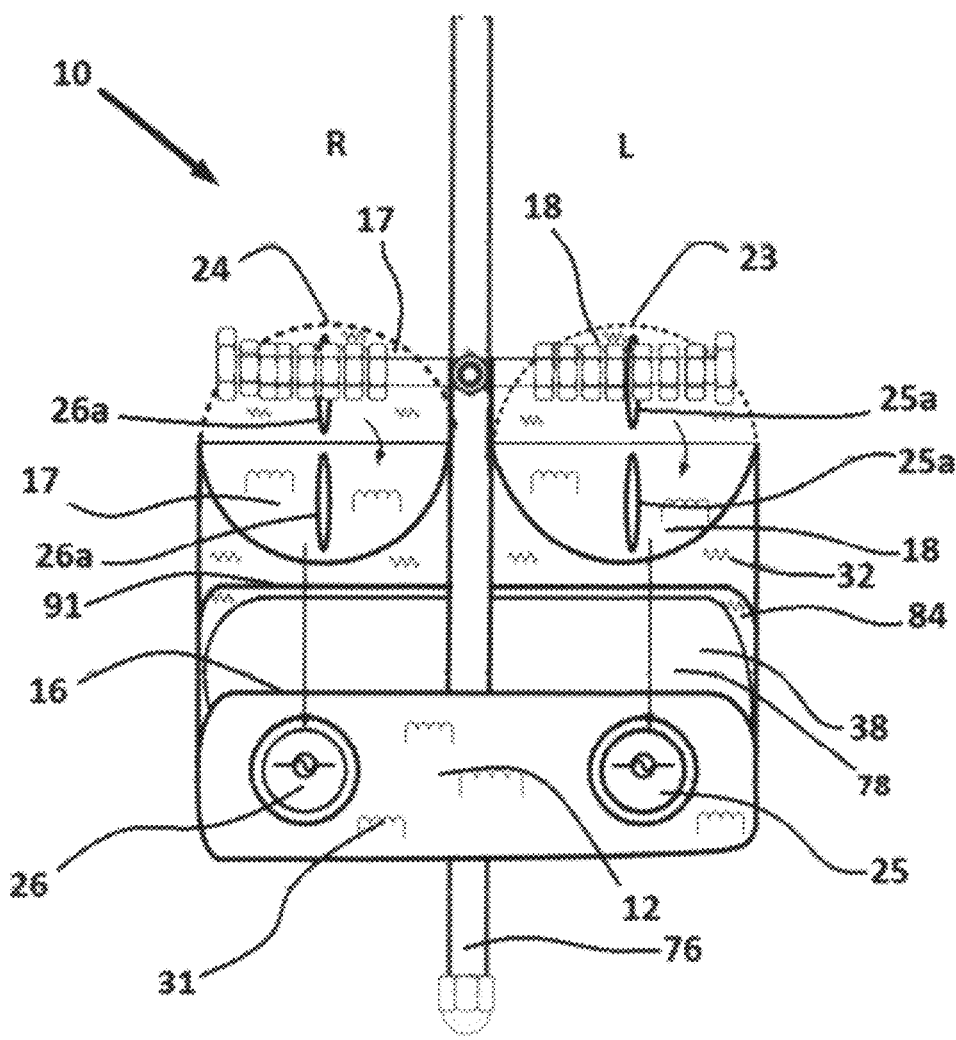

FIG. 24 illustrates a perspective view of a protective chin cup cover assembly 10 showing an external vertical main frame inserted throughin the horizontal aperture 28 of the chin cup cover assembly 10 and showing the posterior portion 12, showing two buttons 25 and 26 therein, folded up and over the bottom edge of the external chin cup interface member, and showing the right anterior flange 17 and left anterior flange 18 positioned on either side of the vertical main frame, and said flanges 17 and 18 beginning to fold over the top edge of the external chin cup interface member.

Figure 25:
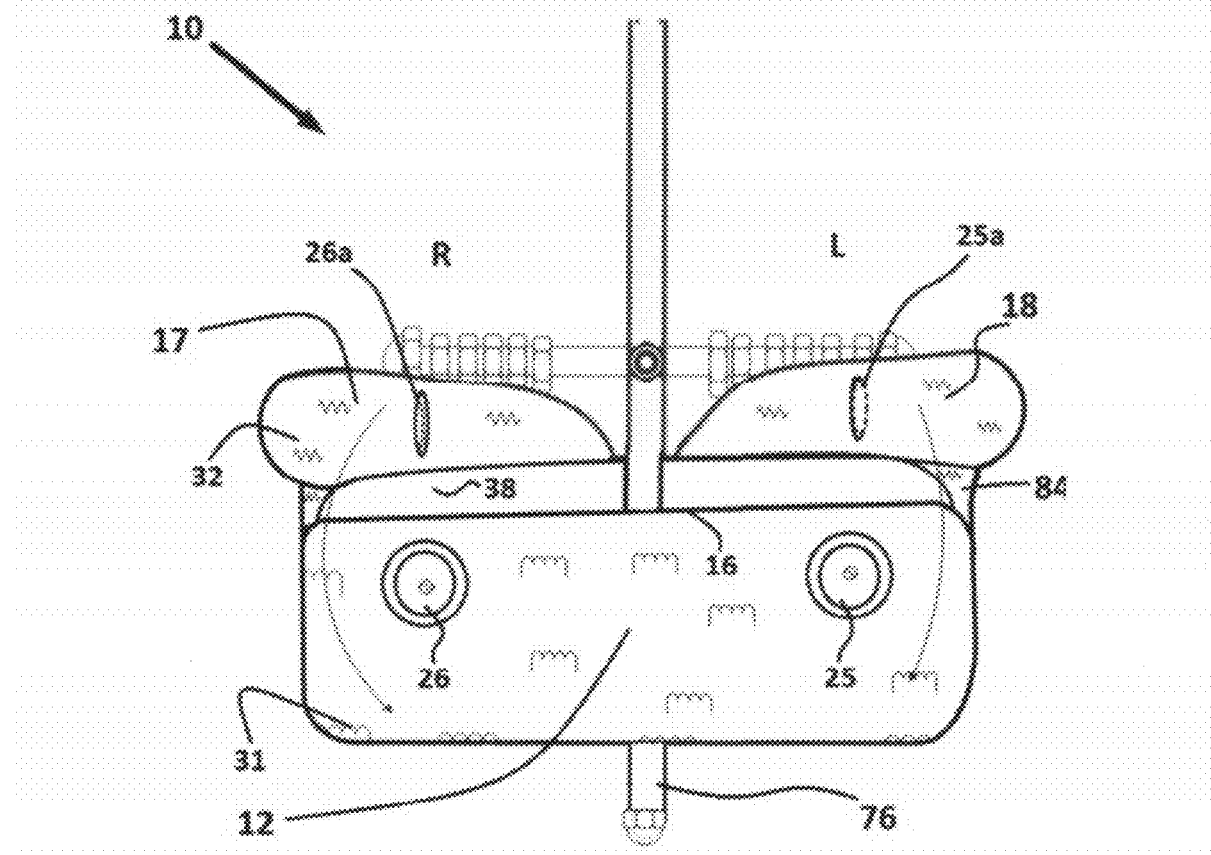

FIG. 25 illustrates a front perspective view of a protective chin cup cover assembly 10, according to the preferred embodiment of the present invention, showing an external vertical main frame inserted throughin the horizontal aperture 28 of the chin cup cover assembly 10 and showing the posterior portion 12, having two buttons 25 and 26 therein, folded up and over the ventral side of the external chin cup interface member and showing the right anterior flange 17 and left anterior flange 18 disposed on either side of the vertical main frame and said flanges 17 and 18 folding over the top edge of the external chin cup interface member ready with button holes 26a and 25a ready to receive corresponding buttons 26 and 25.

FIG. 26(a)-(c), FIG. 26a is a front perspective view of a protective chin cup cover assembly 10, according to the preferred embodiment of the present invention, installed upon an external chin cup interface, showing the protective chin cup cover assembly 10 in the closed buttoned secured position; and FIG. 26(b) illustrating a right side perspective view of the closed chin cup cover 10 against a wearer's chin 94; and FIG. 26(c) illustrating a left side perspective view of the closed chin cup cover 10 against a wearer's chin 94.

Figure 27:
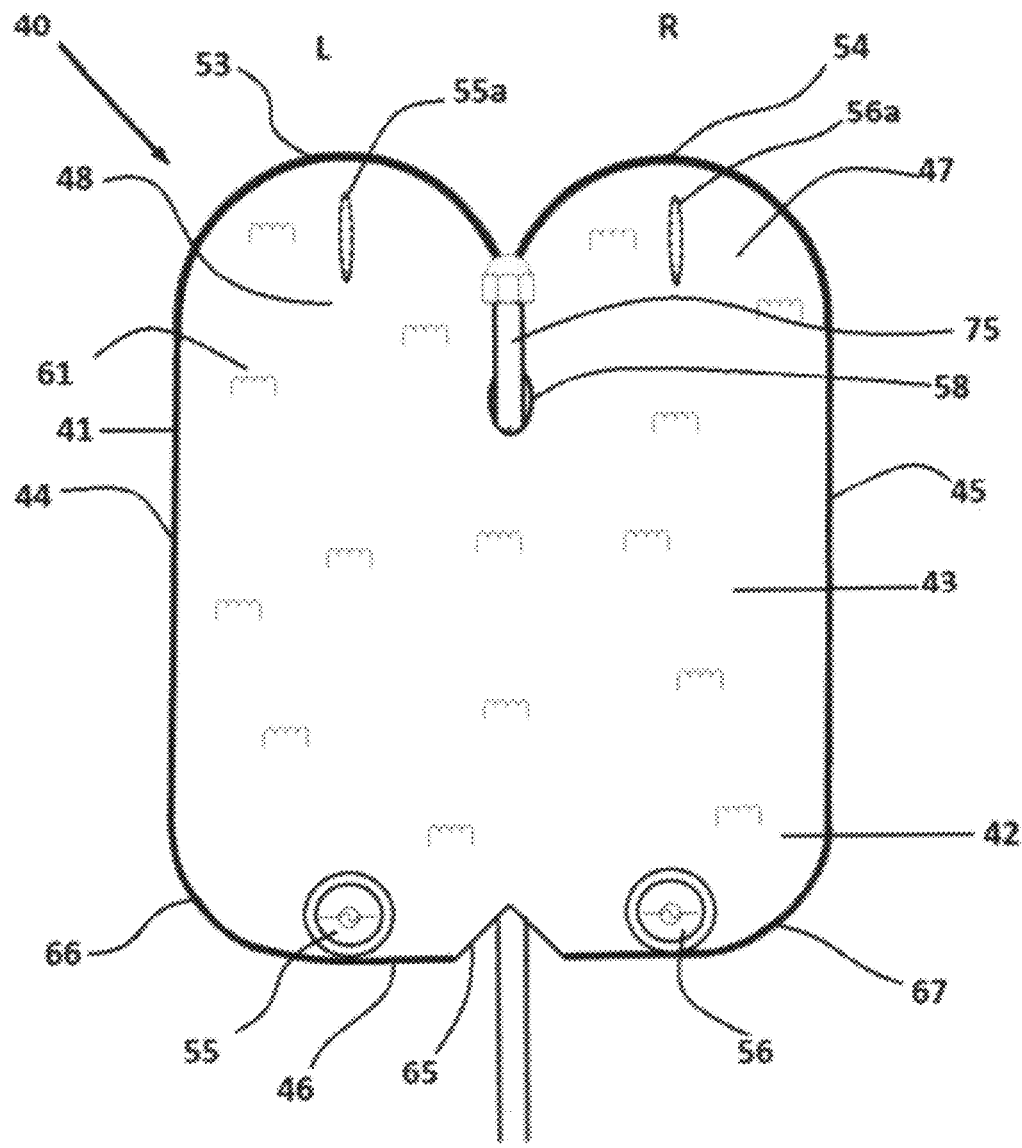

FIG. 27 illustrates the obverse soft side 61 of a protective forehead pad cover assembly 40, according to the preferred embodiment of the present invention, pivotally maneuvered for installation upon an external forehead pad interface, showing the top end of an external orthodontic protraction vertical main frame inserted throughin the vertical aperture 58 of the protective forehead pad cover assembly.

Figure 28:
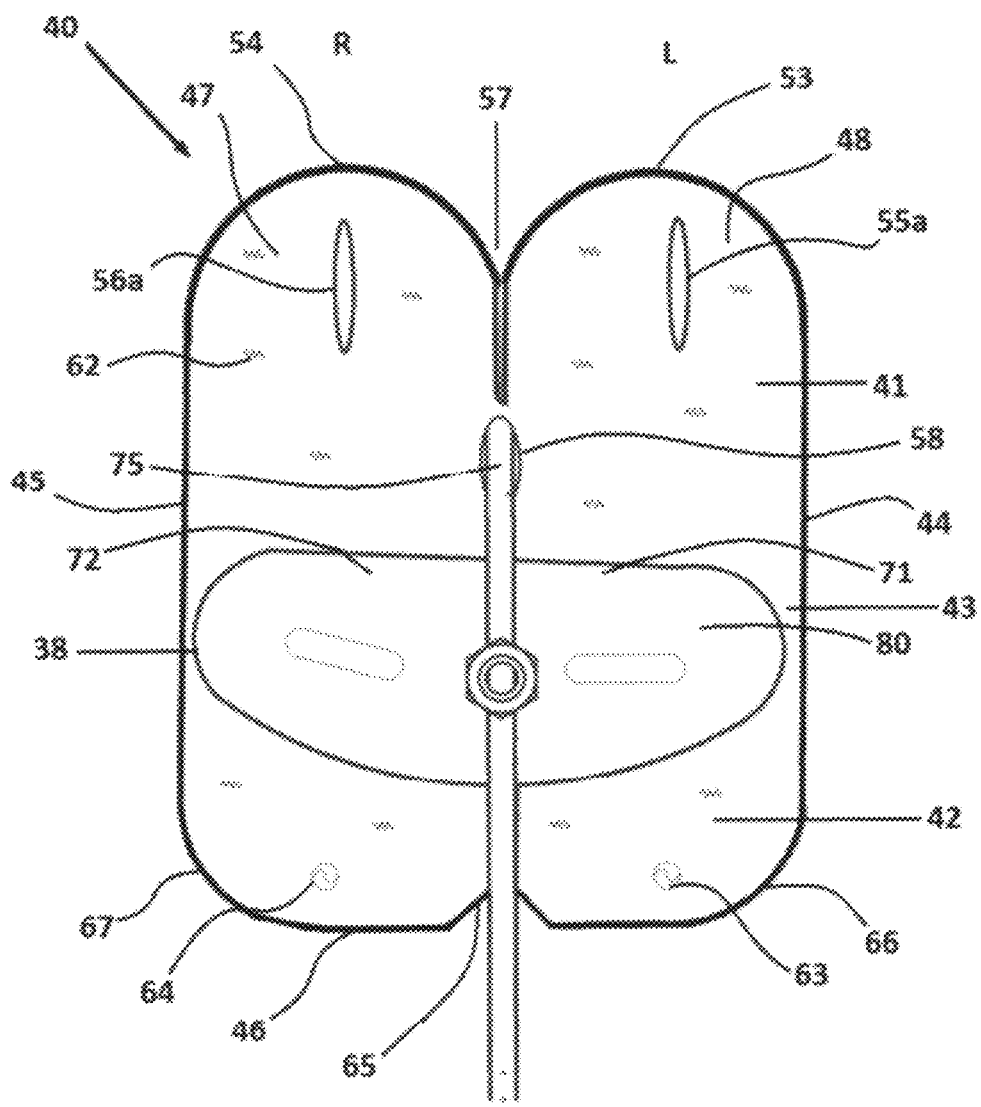

FIG. 28 illustrates a perspective view of a protective forehead pad cover assembly 40, according to the preferred embodiment of the present invention, illustrating the reverse view of FIG. 27, showing reverse dull side 62 of the protective forehead pad cover 40 pivotally positioned behind an external forehead pad interface member of an external orthodontic protraction headgear interface and showing the top end of an external main frame inserted throughin the vertical aperture 58 of a protective forehead pad cover assembly 40.

Figure 29:
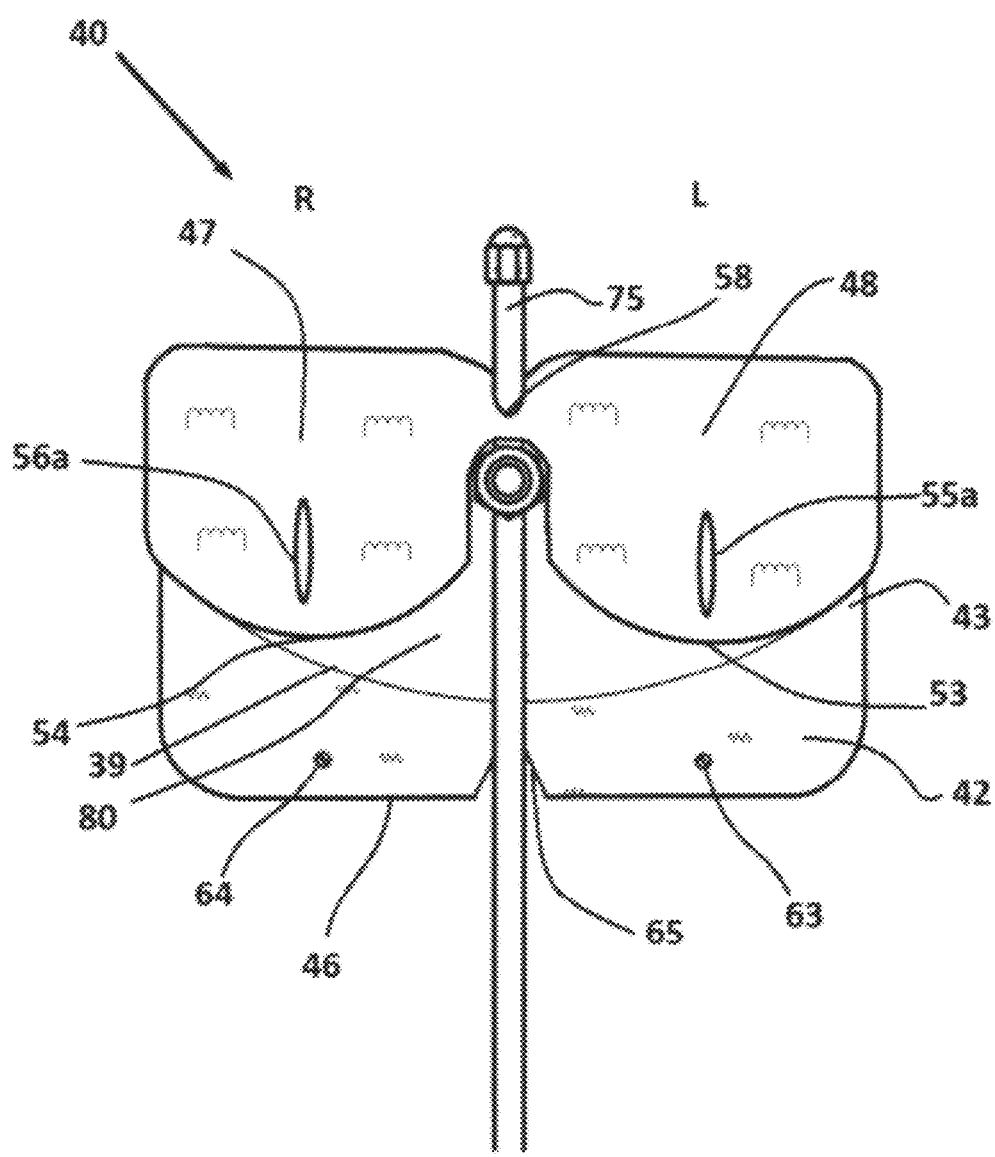

FIG. 29 illustrates a perspective view of a protective forehead pad cover assembly 40, according to the preferred embodiment of the present invention, showing the right anterior flange 47 and the left anterior flange 48, each with a button hole 56a and 56b therein, folded down over the top edge of a forehead pad interface.

Figure 30:
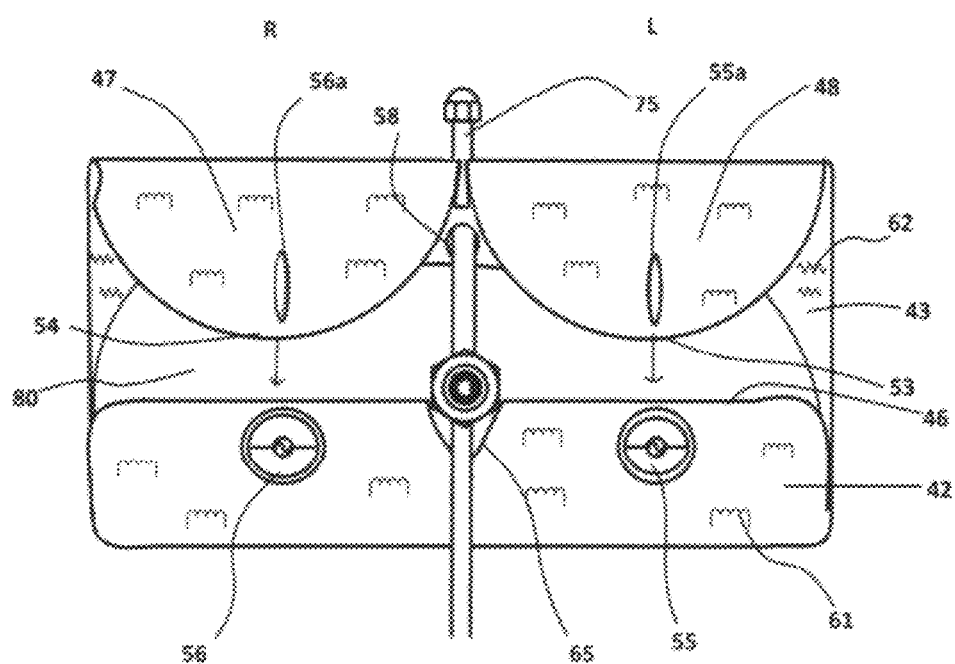

FIG. 30 illustrates a perspective view of a protective forehead pad cover assembly 40, according to the preferred embodiment of the present invention, showing the posterior portion 42 having two buttons 55 and 56, folded up over the bottom edge of a forehead pad cover interface, and the right flange 47 and the left flange 48 showing a button hole 56a and 55a therein, urged towards the corresponding buttons 56 and 55.

FIG. 31(a)-(c), FIG. 31(a) a front view of a protective forehead pad cover assembly 40, according to the preferred embodiment of the present invention, installed upon an external forehead pad interface, showing the protective forehead pad cover assembly 40 in the closed secured buttoned position; FIG. 31(b) illustrating a right side perspective view of the closed forehead pad cover assembly 40 against a wearer's forehead 95; FIG. 31(c) illustrates a left perspective view of the closed forehead pad cover assembly 40 against a wearer's forehead.

Figure 32:
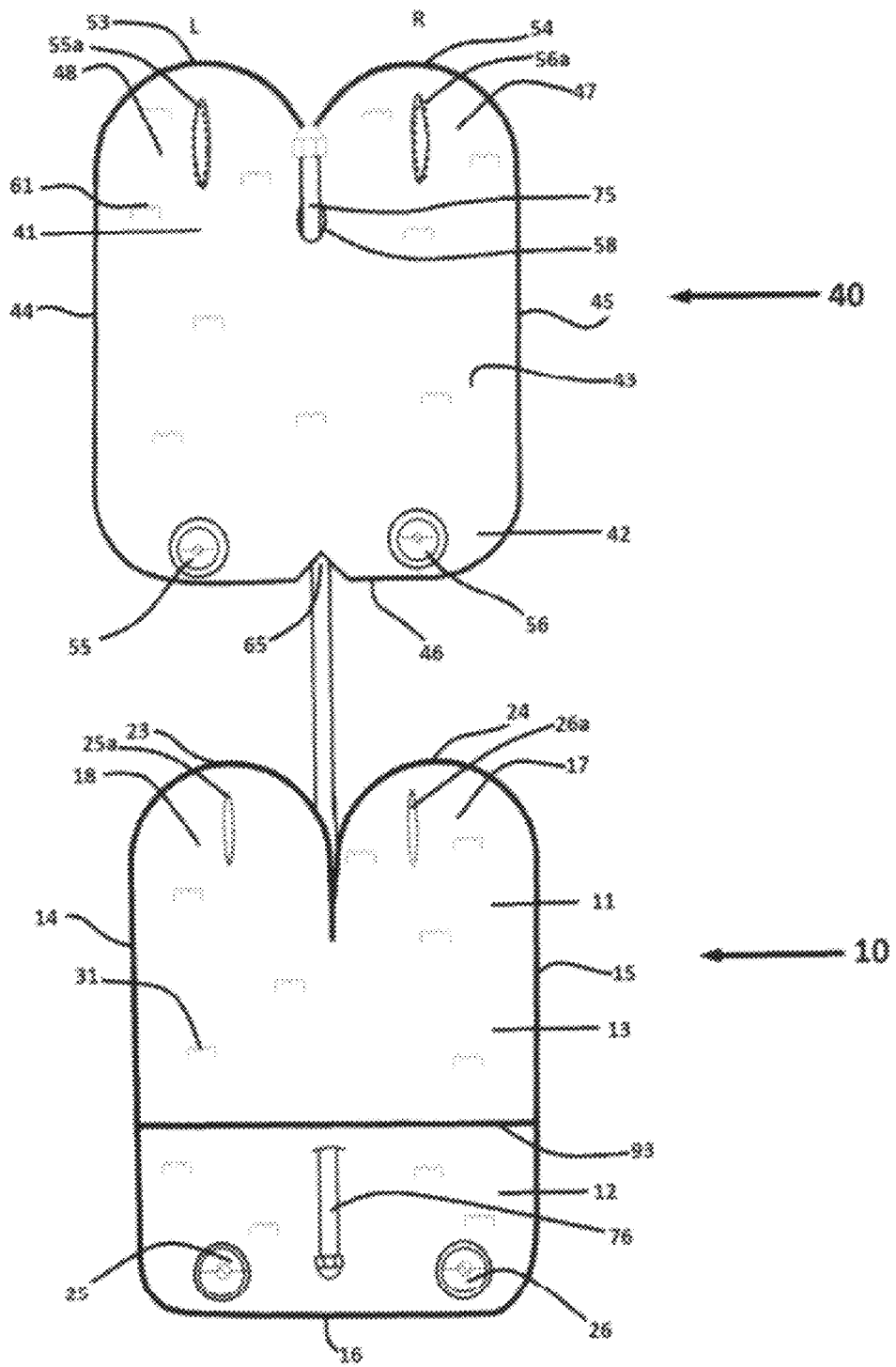

FIG. 32 illustrates a perspective view of a protective chin cup cover assembly 10 and perspective view of protective forehead pad cover assembly 40, according to the preferred embodiment of the present invention, from the perspective of the wearer, upon installation of the protective chin cup cover 10 and forehead pad cover 40 upon the external orthodontic protraction headgear appliance.

Figure 33:
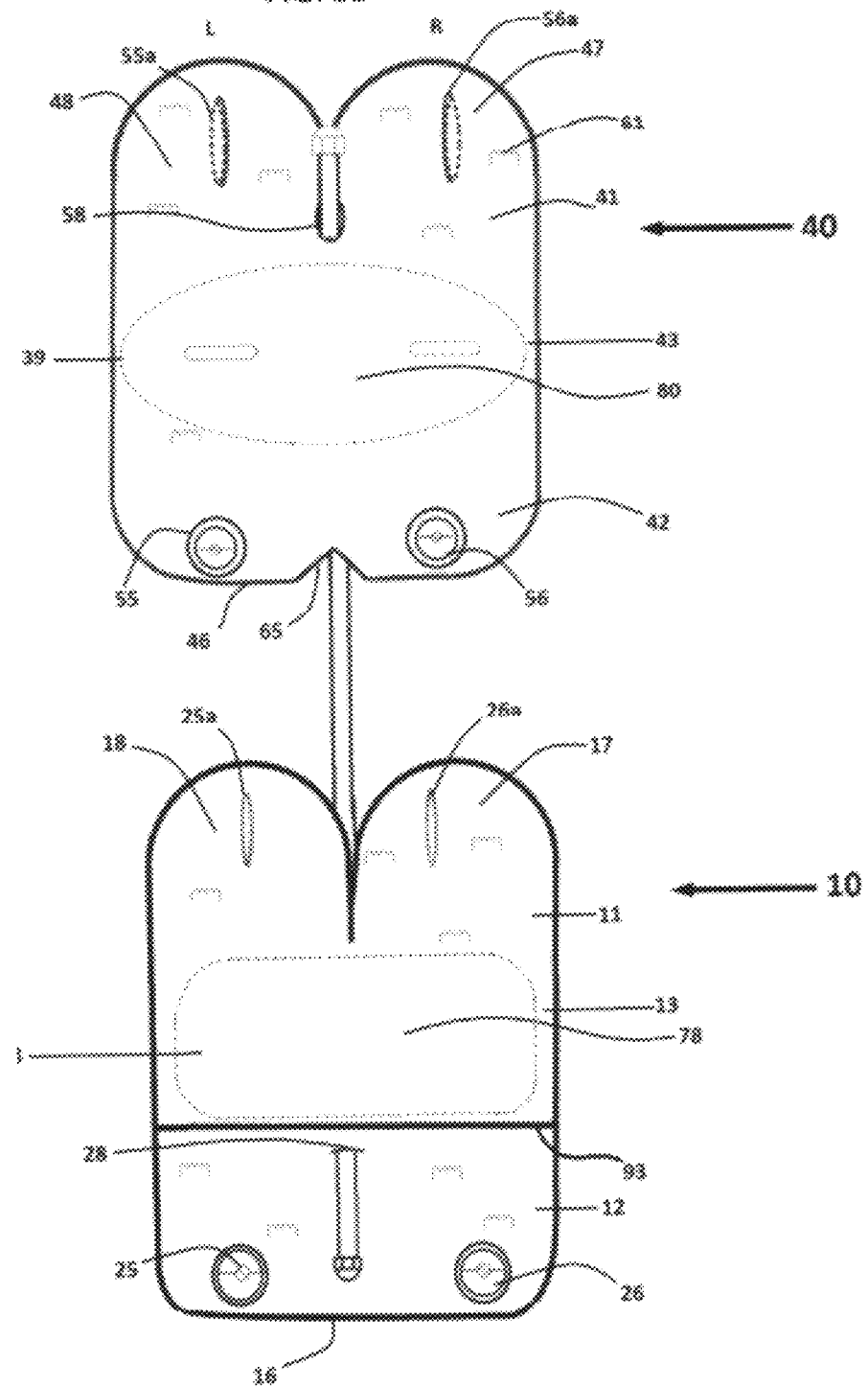

FIG. 33 illustrates a perspective view of FIG. 32, showing the position of the external chin cup interface behind the protective chin cup cover assembly 10; the external forehead pad interface behind the protective forehead pad cover assembly 40, and the position of the vertical mainframe of the orthodontic protraction headgear appliance, upon installation of the chin cup cover 10 and forehead pad cover 40 upon an external orthodontic protraction headgear appliance.

Figure 34:
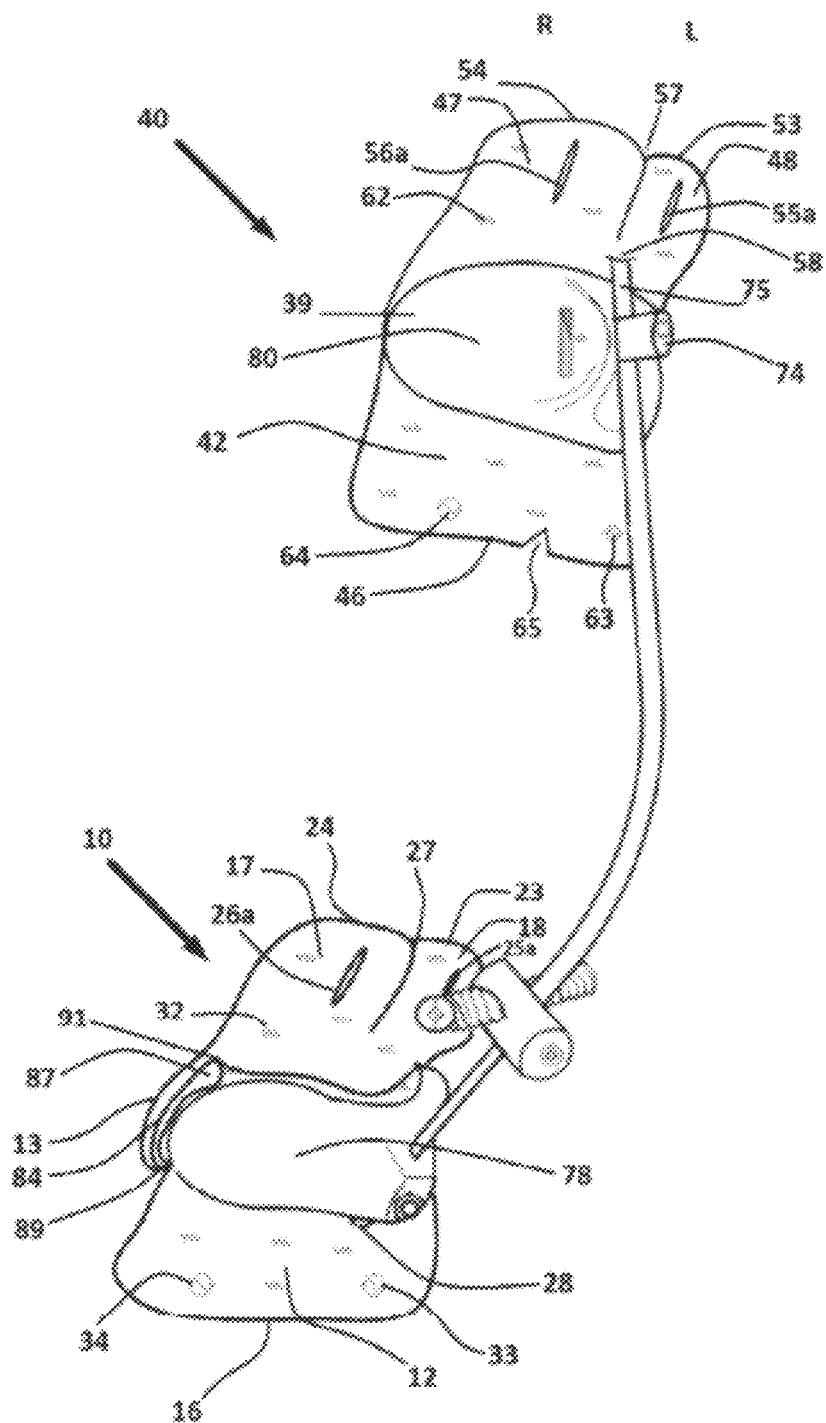

FIG. 34 illustrates a perspective side view of the protective chin cup cover 10 and protective forehead pad cover 40, according to the preferred embodiment of the present invention, showing installation of the protective chin cup cover assembly 10 upon an external chin cup interface and the protective forehead pad cover assembly 40 upon an external forehead pad interface, of an orthodontic protraction headgear appliance.

Figure 35:
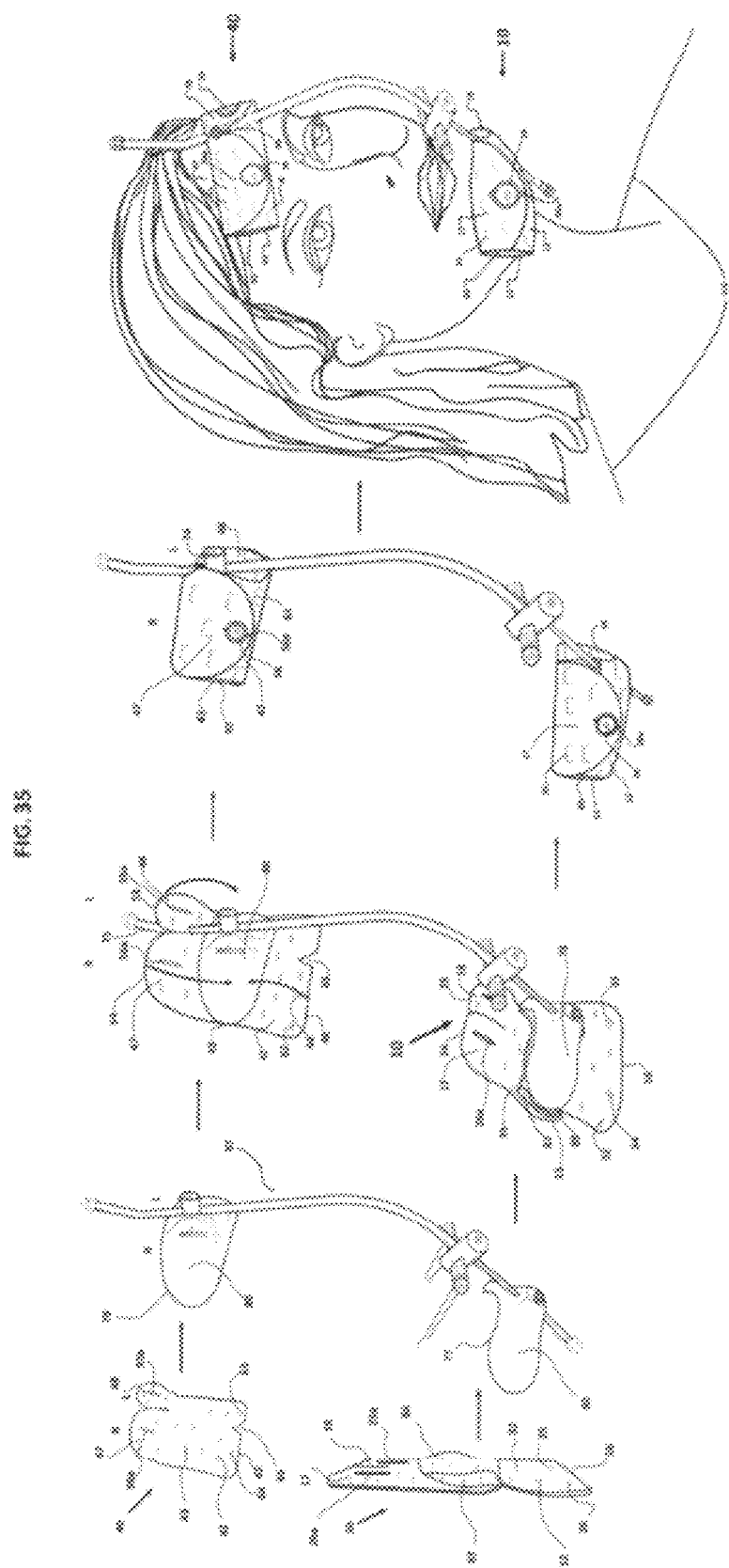

FIG. 35 illustrates a perspective view of method of installation, according to the preferred embodiment of the present invention, of a protective chin cup cover assembly 10 and a protective forehead pad cover assembly 40 upon an orthodontic protraction headgear appliance.

Figure 36:
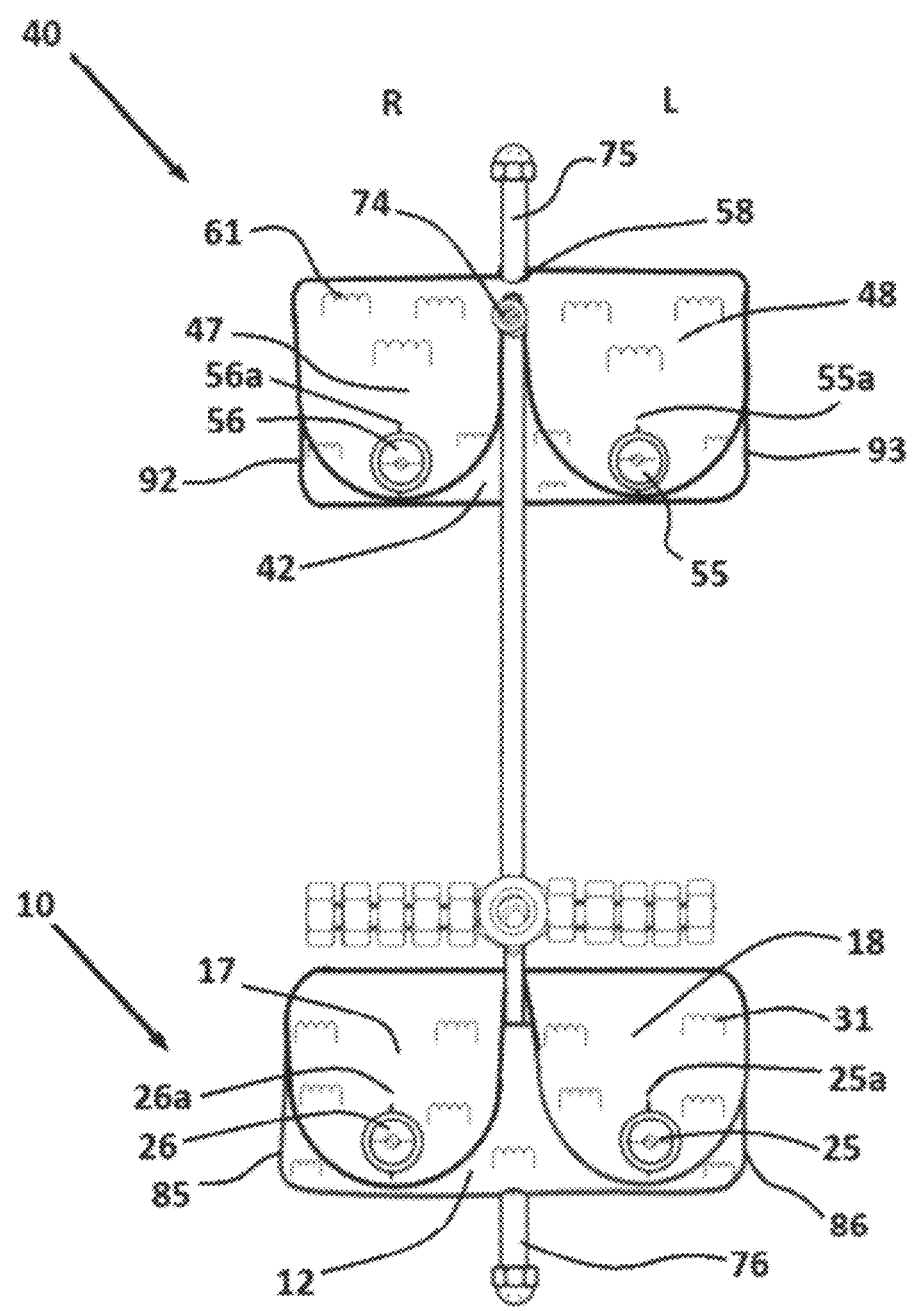

FIG. 36 illustrates a perspective front view, according to the preferred embodiment of the present invention, of a protective chin cup cover assembly 10 and a protective forehead pad cover assembly 40, installed and in closed buttoned position secured on an external orthodontic protraction headgear appliance.

Figure 37:
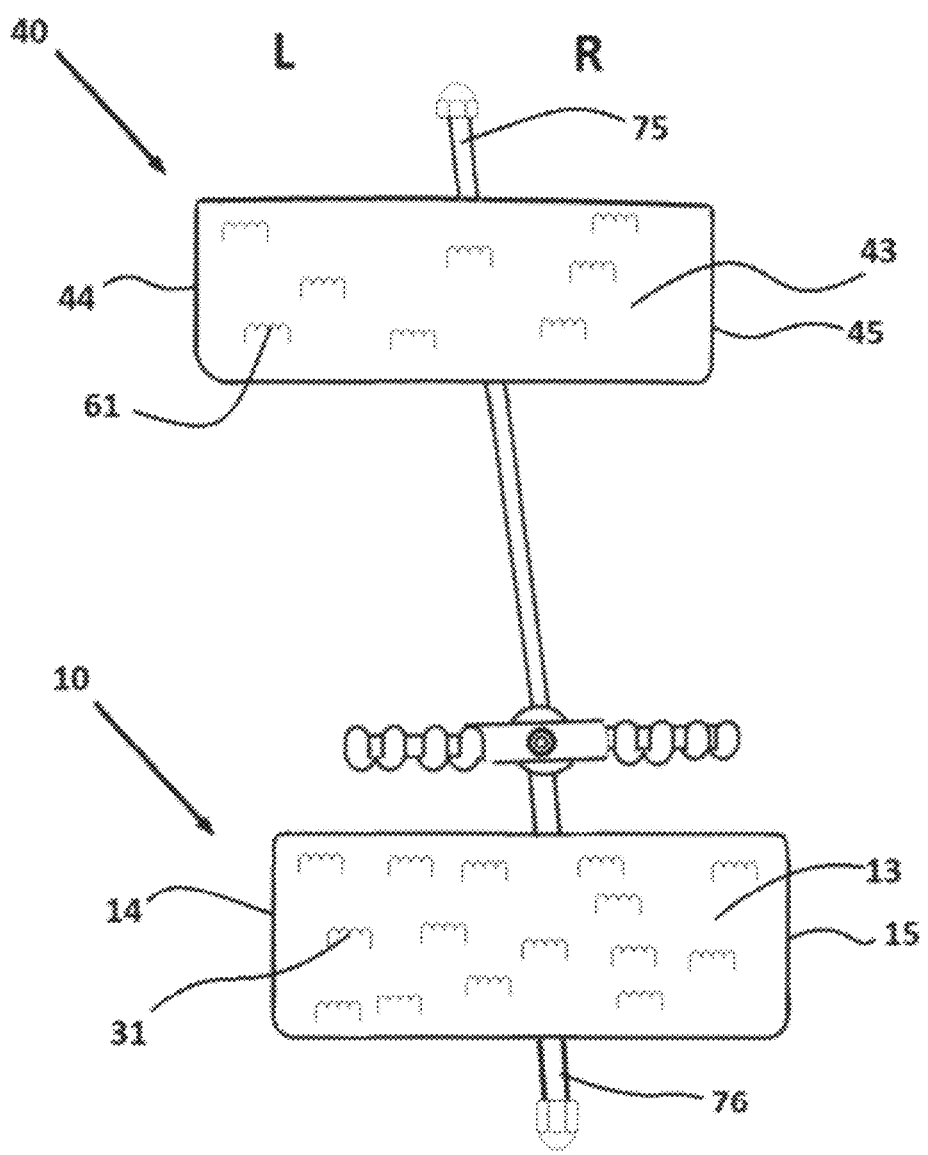

FIG. 37 illustrates a perspective rear view of FIG. 36, according to the preferred embodiment of the present invention, showing protective chin cup cover 10 and a protective forehead pad cover assembly 40 installed upon an external orthodontic protraction headgear appliance.

REFERENCE NUMERALS

Chin Cup Cover
10—CHIN CUP COVER ASSEMBLY
11—ANTERIOR PORTION
12—POSTERIOR PORTION
13—CHASSIS PORTION
14—LEFT LATERAL SIDE EDGE
15—RIGHT LATERAL SIDE EDGE
16—POSTERIOR MARGINAL EDGE
17—RIGHT ANTERIOR FLANGE
18—LEFT ANTERIOR FLANGE
19—LEFT LATERAL SIDE EDGE OF LEFT ANTERIOR FLANGE (exterior)
20—RIGHT LATERAL SIDE EDGE OF LEFT ANTERIOR FLANGE (interior)
21—RIGHT LATERAL SIDE EDGE OF RIGHT ANTERIOR FLANGE (exterior)
22—LEFT LATERAL SIDE EDGE OF RIGHT ANTERIOR FLANGE (interior)
23—LEFT ANTERIOR ARCHED EDGE OF LEFT ANTERIOR FLANGE
24—RIGHT ANTERIOR ARCHED EDGE OF RIGHT ANTERTIOR FLANGE
25—LEFT BUTTON
26—RIGHT BUTTON
25a—LEFT BUTTON HOLE
26a—RIGHT BUTTON HOLE
27—LONGITUDINAL CUT
28—HORIZONTAL APERTURE
29—LONGITUDINAL AXIS
30—LATERAL AXIS
31—OBVERSE SOFT SIDE
32—REVERSE DULL SIDE
33—REVERSE SIDE OF LEFT BUTTON SHOWING THREADS AFFIXED 34—REVERSE SIDE OF RIGHT BUTTON SHOWING THREADS AFFIXED
35—LEFT POSTERIOR ARCUATE CORNER
36—RIGHT POSTERIOR ARCUATE CORNER
82—FLEECE MATERIAL OF CHIN CUP COVER
84—PLEAT
85—RIGHT LATERAL OPENING OF CHIN CUP COVER
86—LEFT LATERAL OPENING OF CHIN CUP COVER
87—RIGHT LA FERAL OPENING OF PLEAT
88—LEFT LATERAL OPENING OF PLEAT
89—PROXIMAL END OF PLEAT
90—STITCHED SEAM
91—DISTAL END OF PLEAT
93—REVERSE SIDE OF STITCHED SEAM AT PROXIMAL END OF PLEAT
94—WEARER'S CHIN
S1—SEAM LINE 1
S2—SEAM LINE 2
F1—FOLD LINE
Forehead Pad Cover
40—FOREHEAD PAD COVER
41—ANTERIOR PORTION
42—POSTERIOR PORTION
43—CHASSIS PORTION
44—LEFT LATERAL SIDE EDGE
45—RIGHT LATERAL SIDE EDGE
46—POSTERIOR MARGINAL EDGE
47—RIGHT ANTERIOR FLANGE
48—LEFT ANTERIOR FLANGE
49—LEFT LATERAL EDGE OF LEFT ANTERIOR FLANGE (exterior)
50—RIGHT LATERAL EDGE OF LEFT ANTERIOR FLANGE (interior)
51—RIGHT LATERAL EDGE OF RIGHT ANTERIOR FLANGE (exterior)
52—LEFT LATERAL EDGE OF RIGHT ANTERIOR FLANGE (interior)
53—LEFT ANTERIOR ARCHED EDGE OF LEFT ANTERIOR FLANGE
54—RIGHT ANTERIOR ARCHED EDGE OF RIGHT ANTERTIOR FLANGE
55—LEFT BUTTON
56—RIGHT BUTTON
55a—LEFT BUTTON HOLE
56a—RIGHT BUTTON HOLE
57—LONGITUDINAL CUT
58—HORIZONTAL APERTURE
59—LONGITUDINAL AXIS
60—LATERAL AXIS
61—OBVERSE SOFT SIDE
62—REVERSE DULL SIDE
63—REVERSE SIDE OF LEFT BUTTON SHOWING THREADS AFFIXED
64—REVERSE SIDE OF RIGHT BUTTON SHOWING THREADS AFFIXED
65—V-SHAPED DART CUT
83—FLEECE MATERIAL FOREHEAD PAD COVER
92—RIGHT LATERAL SIDE OPENING OF FOREHEAD PAD COVER
93—LEFT LATERAL SIDE OPENING OF FOREHEAD PAD COVER
95—WEARER'S FOREHEAD
FL1—FOLD LINE
FL2—FOLD LINE
External Orthodontic Headgear Appliance (not Claimed and Described Only for Illustrative Purposes)
37—EXTERNAL ORTHODONTIC HEADGEAR APPLIANCE
38—EXTERNAL CHIN CUP INTERFACE
39—EXTERNAL FOREHEAD PAD INTERFACE
68—RIGHT SHOULDER MEMBER OF CHIN CUP INTERFACE
69—LEFT SHOULDER MEMBER OF CHIN CUP INTERFACE
72—VERTICAL MAIN FRAME
73—HORIZONTAL BAR
74—SCREW OF FOREHEAD PAD INTERFACE
75—TOP END OF VERTICAL MAIN FRAME
76—BOTTOM END OF VERTICAL MAIN FRAME
77—DORSAL SIDE OF CHIN CUP COVER INTERFACE
78—VENTRAL SIDE OF CHIN CUP COVER INTERFACE
81—ELASTIC BANDS
70—RIGHT MEMBER OF FOREHEAD PAD INTERFACE
71—LEFT MEMBER OF FOREHEAD PAD INTERFACE
79—DORSAL SIDE OF FOREHEAD PAD INTERFACE
80—VENTRAL SIDE OF FOREHEAD PAD INTERFACE
Dictionary
Interface—term means the element of the external orthodontic protraction headgear appliance referred to as the chin cup interface or forehead pad interface. Other terms equivalent to interface is member. i.e., chin cup interface member and forehead interface member.
Wearer—user, patient, orthodontic patient, with Class III Malocclusion disorder
Stretchability, Elasticity—means material or textile or portion thereof made with strands with stretchable properties.
Removably installed—includes the ability to temporarily install the cover on the external appliance and remove the cover from the external appliance by a fastening means and not with the need to alter the cover or the external appliance.
Removably affixed or Intraengaged—fastening means can include a semi-permanent yet detachable means, such as via pivotally placed buttons and button holes, or pivotally placed hook-and-loop fasteners, and/or the like.
Affixed—permanently positioned on a surface, i.e., proximal portion of the pleat is permanently affixed at the seam line having been sewn.
Longitudinal—the term refers to a direction running from a lateral side edge to an opposing lateral side edge of the protective cover assembly and generally parallel to the maximum linear dimension of the cover. Directions within 45 degrees of the longitudinal direction are considered to be "longitudinal."
Lateral—the tend refers to a direction running from a side edge to an opposing side edge of the protective cover assembly and generally at a right angle to the longitudinal direction. Directions within 45 degrees of the lateral direction are considered to be "lateral."
Dispose—the term disposed refers to an element being positioned in a particular place or position in a unitary structure with other elements, and is permanently continuously attached or related to the unitary structure.
Attached—the term refers to elements being connected or united by fastening, adhering, bonding, etc. by any method suitable for the elements being attached together and their constituent material by a fastening means.
Fastening means—the term refers to attaching means which are removably inserted to another of two corresponding members causing the two elements to intraengage.

Proximal and Distal—the terms refer respectively to the location of an element relatively near to or far from the center of a structure, e.g., the proximal edge of a longitudinally extending element is located nearer to the longitudinal axis than the distal edge of the same element is located relative to the same longitudinal axis.

Dorsal and Ventral—the terms refer respectively to the location of an element that is intended to be placed against or toward (dorsal) the body of a wearer patient when a protective cover is installed on the orthodontic protraction headgear appliance interface members according to the preferred embodiment described in the present invention; and the location of an element that is intended to be placed away (ventral) from the wearer or toward a viewer. Dorsal side of the interface faces the wearer and ventral side of the interface faces the viewer. Synonyms for "dorsal" and "ventral" are "interior" and "exterior"; and "inner" and "outer"; and "inside" and "outside".

Obverse and Reverse—obverse refers to front, forward facing, top side of surface. When the protective cover assembly is orientated and disposed or laid out in preparation for construction synonyms include obverse side as the soft upper or soft top side; and reverse refers to underside, interior side, or reverse side as dull side.

Anterior and Posterior—the terms refer respectively to the location of an element that is intended to be place at the top edge margin portion of the protective cover or the bottom edge margin portion of the single body unit.

Copyright Notice

A portion of the disclosure of this patent contains or may contain material which is subject to copyright protection. The copyright owner has no objection to the photocopy reproduction by anyone of the patent document or the patent disclosure in exactly the form it appears in the Patent and Trademark Office patent file or records, but otherwise reserves all copyrights whatsoever.

Trademark Notice

A portion of the disclosure of this patent document contains or may contain material which is subject to trademark protection. The trademark owner has no objection to the photocopy reproduction by anyone of the patent document or the patent disclosure in exactly the form it appears in the Patent and Trademark Office patent file or records, but otherwise reserves all trademarks whatsoever.

DETAILED DESCRIPTION

Figure 1:
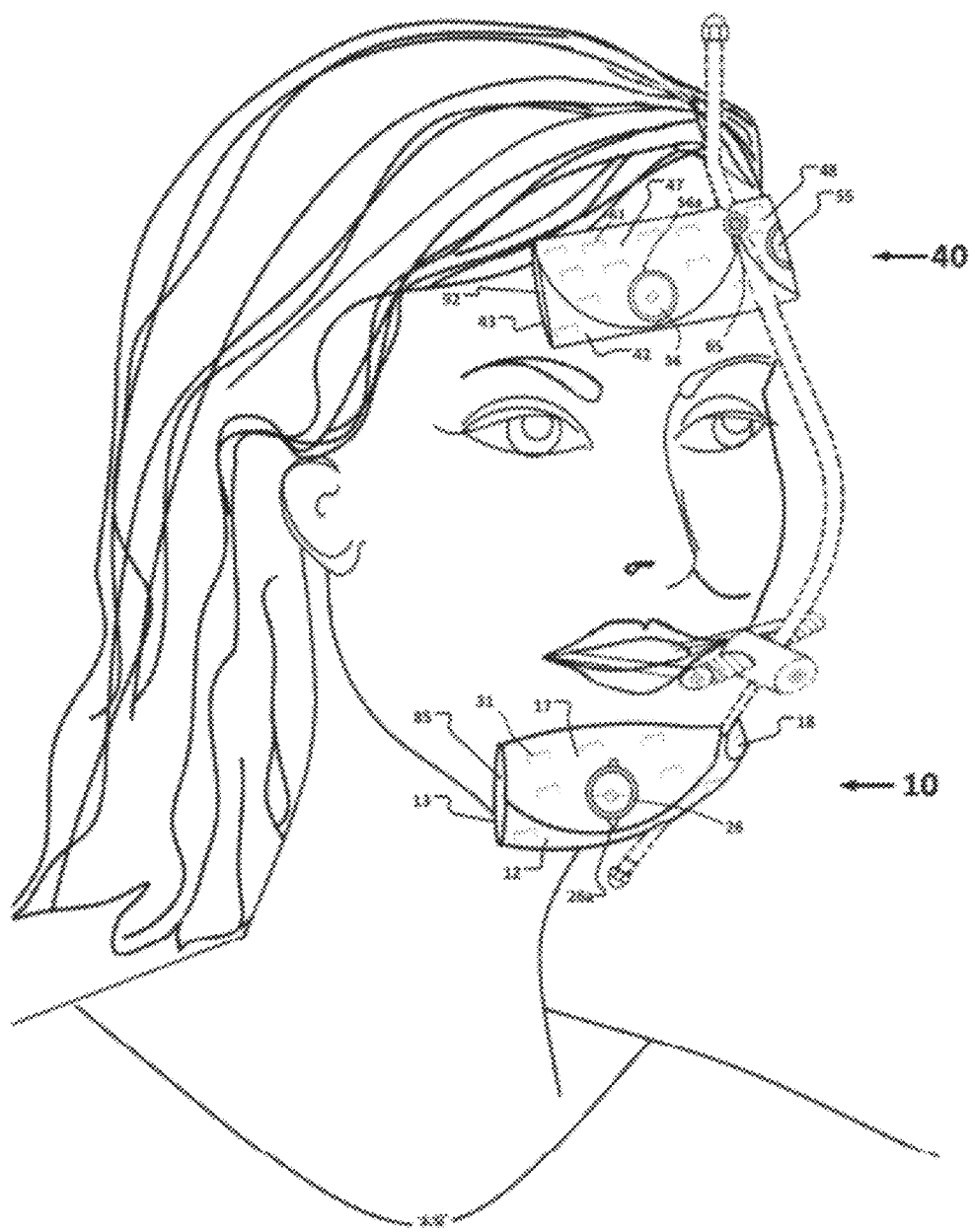
FIG. 1 is a perspective view, according to the preferred embodiment of the present invention, a protective chin cup cover assembly 10 and a protective forehead pad cover assembly 40 in use installed on an orthodontic protraction headgear appliance worn by an orthodontic patient wearer.
Figure 2:
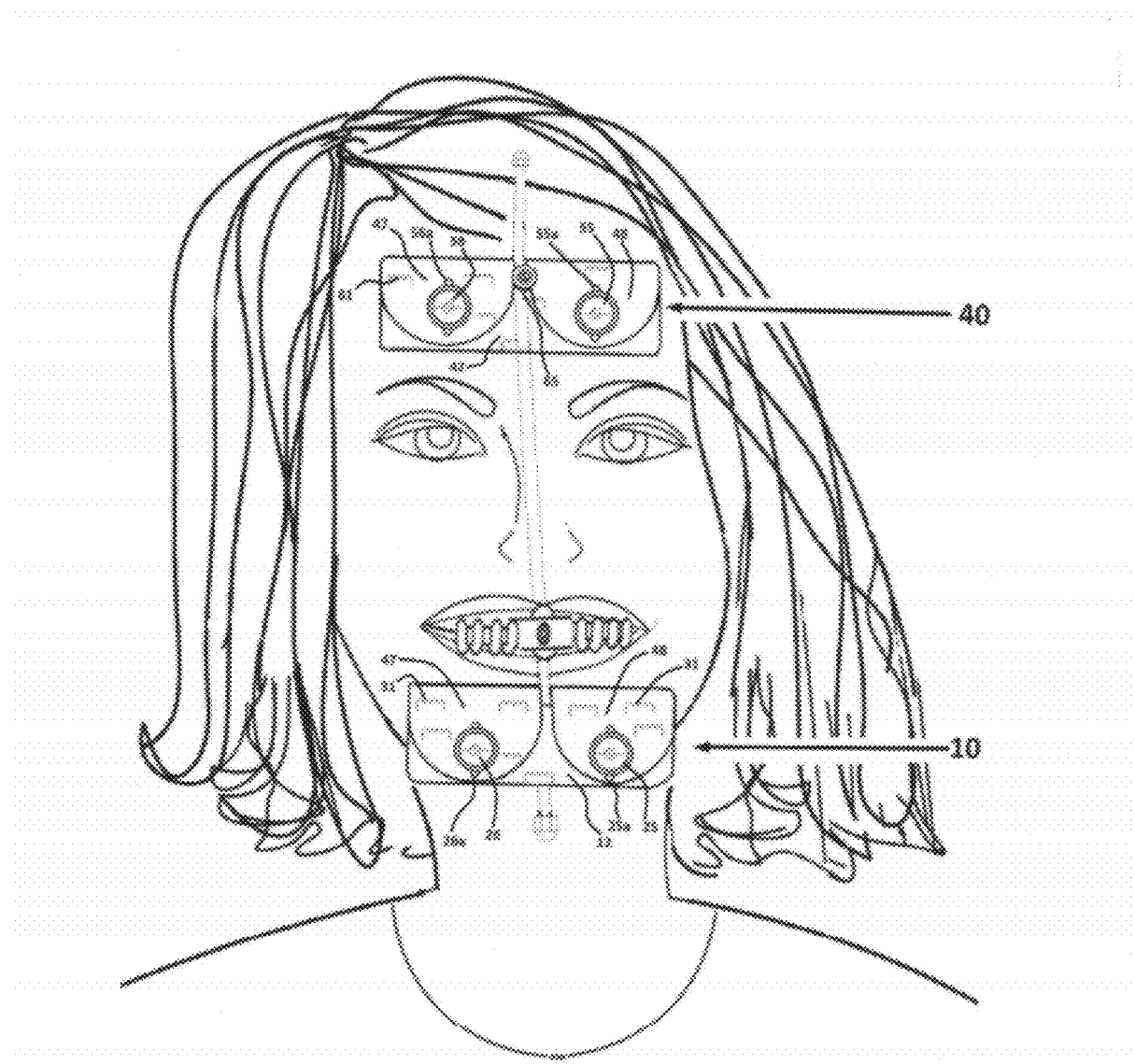
FIG. 2 is a front perspective view, according to the preferred embodiment of the present invention, a protective chin cup cover assembly 10 and protective forehead pad cover assembly 40 installed on an orthodontic protraction headgear appliance worn by an orthodontic patient.
Figure 4:
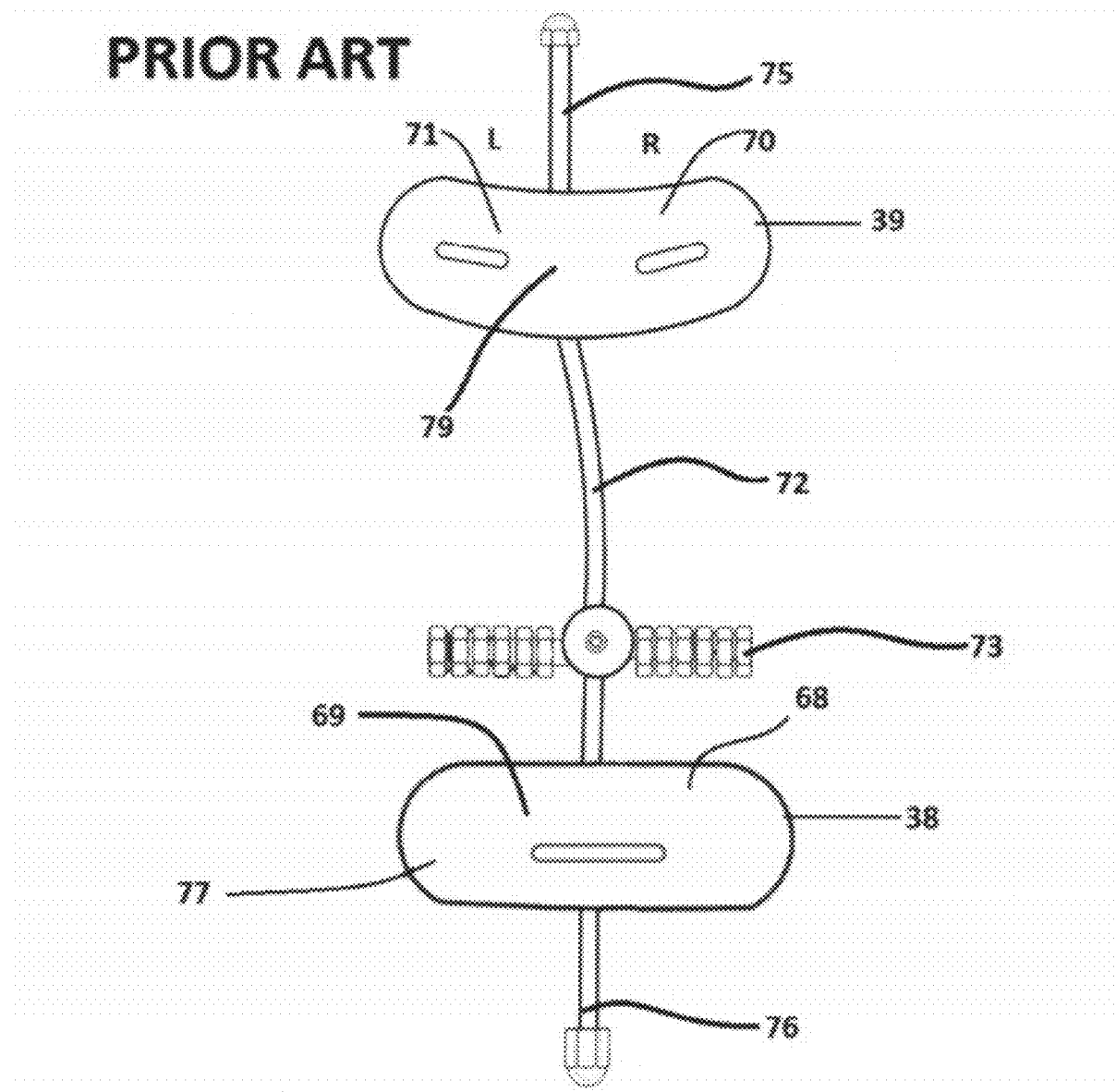
FIG. 4 is prior art of dorsal side of a conventional orthodontic protraction headgear appliance typically used in the treatment of Class III Malocclusion disorder, illustrated for descriptive purposes and not claimed as part of the present invention.
Figure 5:
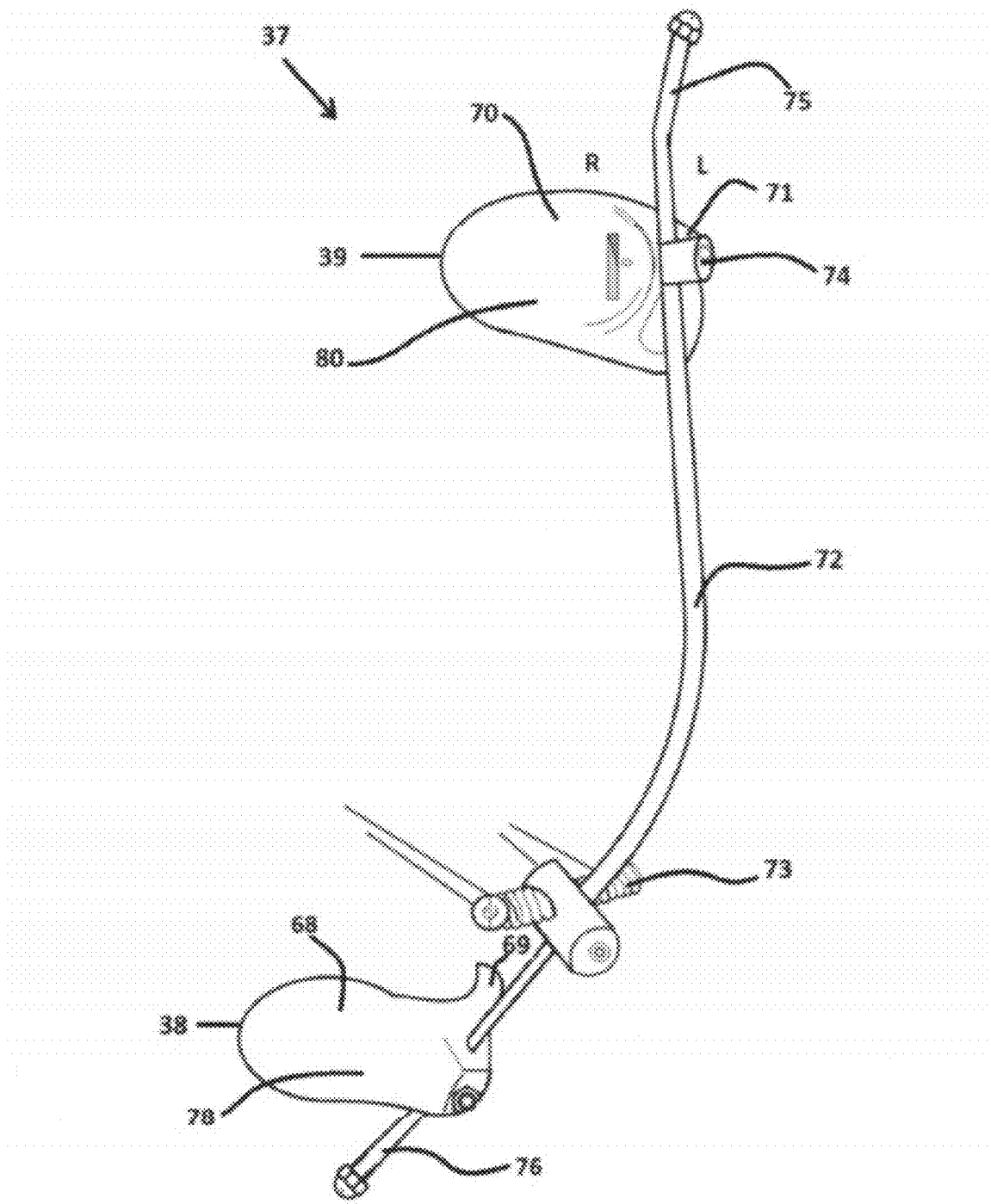
FIG. 5 is prior art of perspective side view of conventional orthodontic protraction headgear appliance used in the treatment of Class III Malocclusion disorder, illustrated for descriptive purposes and not claimed as part of the present invention.
Figure 6:
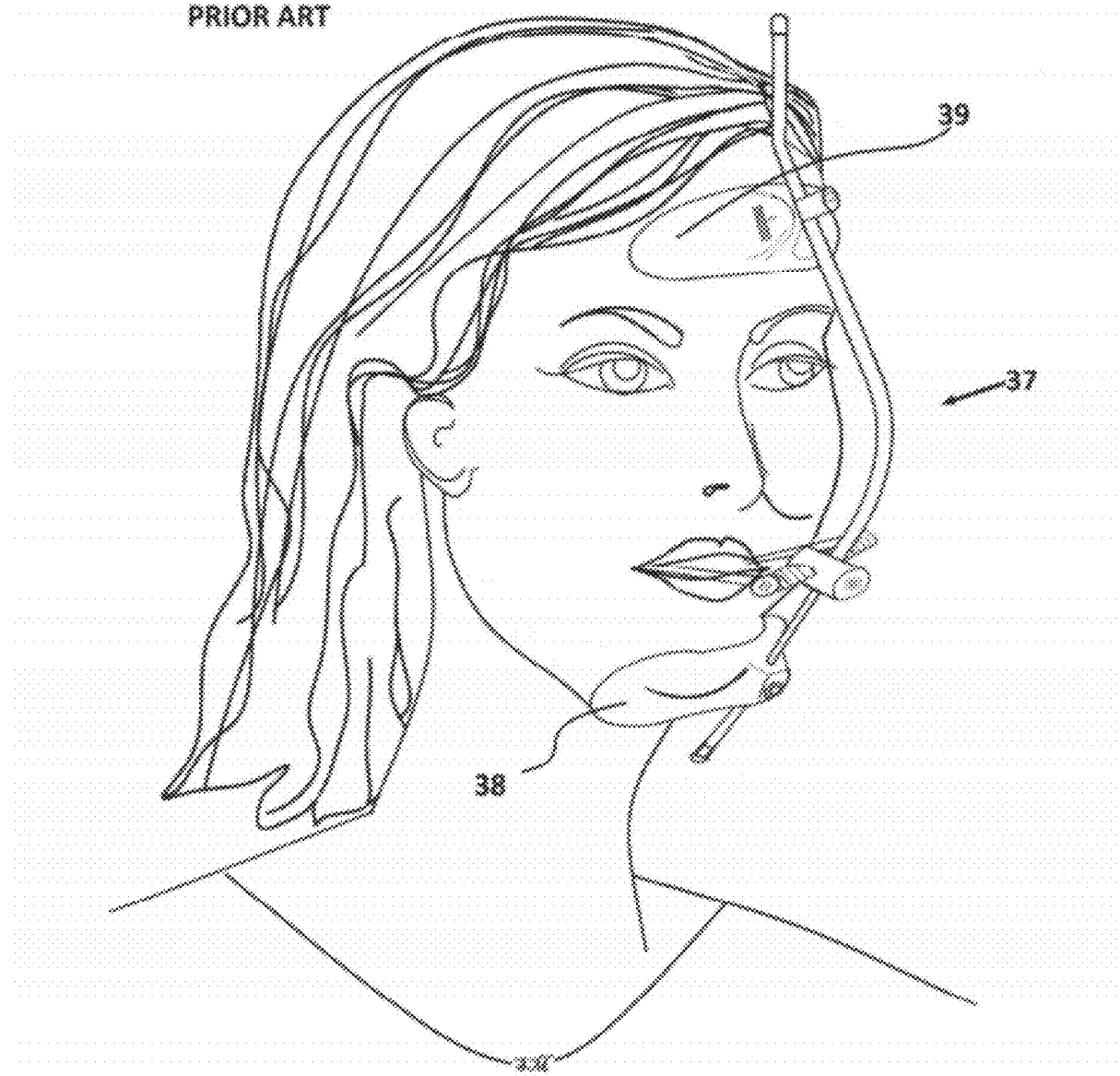
FIG. 6 is a prior art of a perspective view of a conventional orthodontic protraction headgear appliance worn by a patient, and there is no protective chin cup cover assembly installed on the chin cup interface and there is no protective forehead pad cover assembly installed on the forehead pad interface, illustrated for descriptive purposes and not claimed as part of the present invention.

In referring to the drawings herein, the protective chin cup cover assembly 10 and the protective forehead pad cover assembly 40 for the orthodontic protraction headgear appliance 37 external chin cup interface 38 and an external forehead pad interface 39 are described. As illustrated in FIGS. 1 and 2, the protective chin cup cover assembly 10 and the forehead pad cover assembly 40 are typically used by the wearer or patient with one external orthodontic protraction appliance 37 and therefore are described and claimed together. The external orthodontic protraction appliance 37, as illustrated in FIGS. 3, 4, 5, and 6 is not claimed as the present invention but is described in detail to assist in the detailed description of the instant invention. The present invention discloses a protective cover assembly for use with an external orthodontic protraction headgear appliance 37 with chin cup interface 38 and with forehead pad interface 39 such that a first aspect of the invention is a protective chin cup cover assembly 10 for use with an external orthodontic protraction headgear appliance chin cup interface 38; and a second aspect of the present invention is a protective forehead pad cover assembly 40 for use with an external orthodontic protraction headgear appliance forehead pad interface 39. The protective cover assemblies 10 and 40 are configured such that the hard surface of the chin cup interface 38 and the hard surface of the forehead pad interface 39 of the external orthodontic headgear appliance 37 never come into contact with the wearer's facial skin at the chin or the facial skin at the forehead, as illustrated in FIGS. 1 and 2, as they would without the protective chin cup cover assembly 10 and without the protective forehead pad cover assembly, as illustrated in FIG. 6. The protective chin cup cover assembly 10 and the protective forehead pad cover assembly 40 are manufactured with a soft, flexible, breathable, material, preferably polyester fleece, and thereby typically precludes the wearer from removing the orthodontic protraction headgear appliance 37 because of discomfort or because of soreness, and therefore advances the utility of the orthodontic protraction headgear appliance 37 and compliance with use during treatment, particularly with growing children and adolescent patients having Class III Malocclusion disorder.

FIG. 1 illustrates a side perspective view of the protective chin cup cover assembly 10 and the protective forehead pad cover assembly 40 in use installed upon an external orthodontic protraction headgear chin cup interface 38 and a forehead pad interface 39, respectively, as the orthodontic protraction headgear appliance 37 is in use and is being worn by an orthodontic patient, according to the preferred embodiment of the present invention. FIG. 2 is a front perspective view, according to the preferred embodiment of the present invention, illustrating a protective chin cup cover assembly 10 and protective forehead pad cover assembly 40 installed on an orthodontic protraction headgear appliance 37 and shown being worn by an orthodontic patient.

As illustrated in FIGS. 1 and 2, the protective chin cup cover assembly 10 and the protective forehead pad cover assembly 40 is installed upon an orthodontic protraction headgear appliance 37. The orthodontic protraction headgear appliance 37 is illustrated in FIGS. 3-6 and is illustrated for descriptive purposes and not claimed as part of the present invention. FIGS. 1 and 2 further illustrates a chin cup cover assembly 10 secured by a fastening means, preferably two buttons 25 and 26 positioned within the posterior portion 12 of the chin cup cover assembly, such that the two buttons 25 and 26 intraengage button holes 25a and 26a positioned within the anterior flanges 17 and 18, to securely close the protective chin cup cover assembly 10 around the external chin cup interface 38 of the orthodontic protraction headgear appliance 37, as illustrated and described further below in FIGS. 22-26(a)-(c), 36, and 37. Similarly, as further illustrated in FIGS. 1 and 2, the protective forehead pad cover assembly 40, according to the preferred embodiment of the present invention, is installed upon an orthodontic protraction headgear appliance 37 secured by a fastening means, preferably two buttons 55 and 56 positioned within the posterior portion 42 of the forehead pad cover assembly 40, such that the two buttons 55 and 56 intraengages button holes 55a and 56a, positioned within the anterior flanges 47 and 48 to securely close the forehead pad cover assembly 40 around the external forehead pad interface 39 of the orthodontic protraction headgear appliance, as further illustrated and described further below in FIGS. 27-31(a)-(c), 36, and 37.

As shown in FIGS. 1, 2, 26(a)-(c), 36, and 37 the obverse soft side 31 of fleece material 82 of the protective chin cup cover assembly 10, according to the preferred embodiment of the present invention, is visible as the chin cup cover 10 surrounds the total ventral side 78 and dorsal side 77 of the headgear chin cup interface 38 providing a soft, cushioning, absorbing, buffering, membrane between the wearer's facial skin at the site of the wearer's chin and the hard rigid surface of the chin cup interface 38 of the orthodontic protraction headgear appliance 37, and contemporaneously providing a decorative chin cup cover 10 with two buttons 25 and 26 covering the front ventral portion 78 of the chin cup interface 38 of the orthodontic protraction headgear appliance 37, as shown in FIGS. 1, 2, 26(a), and 36.

As mentioned, FIGS. 1, 2, 26(a), and 36, illustrate the protective chin cup cover assembly 10 removably affixed to the external chin cup interface 38 by fastening means, preferably, two buttons 25 and 26, and two corresponding button holes 25a and 26a. The two buttons 25 and 26 and corresponding button holes 25a and 26a provide a fastening means which enables for the easy installation of the protective chin cup cover assembly 10 and the easy removal of the chin cup cover assembly 10 for the patient to maneuver when the chin cup cover assembly 10 needs to be washed, or replaced, or if the wearer desires a different color chin cup cover assembly 10.

FIGS. 1, 2, 31(a), 36 and 37, illustrate the orthodontic protraction headgear forehead pad cover assembly 40 removably affixed to the external forehead pad interface 39 by fastening means, preferably two buttons, 55 and 56, and two corresponding button holes 55a and 56a. As shown, in FIGS. 1, 2, 31(a), 36, and 37, the obverse soft side of the material 61 of the protective forehead pad cover assembly 40, preferably polyester fleece, according to the preferred embodiment of the present invention, is visible as the forehead pad cover assembly 40 and surrounds the total ventral side 80 and dorsal side 79 of the orthodontic protraction forehead pad interface 39 providing a soft, cushioning, absorbing, buffering, membrane between the wearer's facial skin at the site of the wearer's forehead and the hard rigid surface of the forehead pad interface 39 of the orthodontic protraction headgear appliance 37, and contemporaneously providing a decorative forehead pad cover assembly 40 with two buttons 55 and 56 covering the front ventral portion 80 of the external forehead pad interface 39 of the orthodontic protraction headgear appliance 37.

As mentioned, FIGS. 1, 2, 27-31(a), and 36 illustrates the protective forehead pad cover assembly 40 removably affixed to the external forehead pad interface 39 by fastening means, particularly two buttons 55 and 56 and two corresponding button holes 55a and 56a. The two buttons 55 and 56 and two button holes 55a and 56a provide a fastening means which enables for the easy installation of the protective forehead pad cover assembly 40 and the easy removal of the forehead pad cover assembly 40 for the patient to maneuver.

The buttons 25 and 26 affixed to the chin cup cover assembly 10, as illustrated in FIGS. 1, 2, 7, 11, 15, 17, 19, 24, 25, 26(a), 32, 33, and 36; and the buttons 55 and 56 affixed to the forehead pad cover assembly 40 as illustrated in FIGS. 1, 2, 9, 11, 13, 15, 30, 31(a), 32, 33, and 36, can be configured in various shapes, colors, indicia, and logos, and decorative embellishments, and together with the varied colors of available fleece materials available to the patient, provide for a decorative cover for the orthodontic protraction device to disguise the medicinal appearance of the orthodontic protraction headgear appliance. More particularly, as illustrated in FIGS. 1, 2, and 36, the buttons 25 and 26 of the protective chin cup cover 10 and the buttons 55 and 56 of the protective forehead pad cover 40 resemble the eyes of a face; and more particularly buttons 25 and 26 of the protective chin cup cover assembly 10 mimic the eyes of a face and the bottom end 76 of the external vertical main frame 72 can be extended resembling a tongue and therefore enable the orthodontic protraction headgear appliance 37 to be fun and humorous for the orthodontic patient to wear. In addition, the soft obverse side 31 of the fleece material 82 of the protective chin cup cover assembly 10, and the soft obverse side 61 of the fleece material 83 of the protective forehead pad cover assembly 40, together with the cushioned membrane they provide, the additional absorbency they provide, and the decorative aesthetic they provide, allow for improved compliance by the orthodontic patient with wearing the orthodontic protraction headgear appliance 37 during the day and while the patient is sleeping.

As illustrated in FIGS. 1, 2, and 26(b)-(c) the protective chin cup cover 10 installed upon an external chin cup interface 38 and as used by a patient wearing an external orthodontic protraction appliance 37 provides an absorbent membrane positioned between the wearer's chin 94 and the hard surface of the external chin cup interface 38 to provide an absorbing means to enable protection against discomfort, deposits of saliva and mouth leaks, perspiration, lingering facial indentations, suction marks, pressure sores, decubitus sores, irritation, cracked skin, redness, breakouts, allergic reactions, and other skin disorders, that arise as a result of wearing the orthodontic protraction headgear appliance during treatment of Class III Malocclusion, particularly when the patient wears the appliance during the night for a consecutive 8-12 hours while the patient is sleeping.

Similarly, as illustrated in FIGS. 1, 2, and 31(b)-(c), the protective forehead pad cover assembly 40 installed upon an external forehead pad interface 39 and used by a patient wearing an external orthodontic protraction headgear appliance 37 provides an absorbent membrane positioned between the wearer's forehead 95 and the hard surface of the external forehead pad interface 39 to provide an absorbing means to enable protection against discomfort, deposits of perspiration and facial flora, and protection against lingering facial indentations, suction marks, redness, cracked skin, breakouts, allergic reactions, microbial infections, pressure sores, decubitus sores, and other skin disorders, that arise as a result of wearing the orthodontic protraction headgear appliance 37, as noted above, especially during the night while the wearer is sleeping while wearing the orthodontic appliance 37 for a consecutive 8-12 hours.

As shown in FIGS. 1 and 2 the chin cup cover assembly 10, according to the preferred embodiment of the present invention, provides a soft absorbent membrane between the hard plastic external chin cup 38 interface and the facial skin of the wearer's chin; and the forehead pad cover assembly 40, provides a soft absorbent membrane between the hard plastic external forehead pad interface 39 and the facial skin of the wearer's forehead, and thereby both protective cover assemblies provide a cushioning means to alleviate pressure upon the skin and underlying tissues immediately surrounding the chin and forehead portions of the face congruent with the external chin cup interface 38 and forehead pad interface 39, respectively, without interfering with the prescribed forces applied by the orthodontic protraction headgear appliance 37 upon the patient's teeth and facial bones during treatment of Class III Malocclusion disorder.

According to the preferred embodiment of the present invention, as shown in FIGS. 7, 8, 11, and 12, the protective chin cup cover assembly 10 is manufactured of soft polyester fleece material 82; and as shown in FIGS. 9, 10, 13, and 14, the forehead pad cover assembly 40 is manufactured of soft polyester fleece material 83. In general, fleece material is preferred because it is slightly stretchable and can be stretched approximately ½ inch at its side borders along its lateral axis. Other materials were experimented with but no other material was as enabling as fleece for stretch material of sufficient pile thickness, obverse softness, cushioning, and absorbency, to assuage skin irritation, cracked skin, breakouts, lingering facial indentations, pressure sores, and decubitus sores, as experienced by patients wearing the orthodontic protraction headgear appliance 37 during treatment. In addition, the fleece material is preferred because it has two surfaces, and obverse top surface which is soft with a characteristic pile, and it has an underside which is dull with a lesser pile. In addition, polyester fleece is preferred because of its resiliency when cut and inherent property to remain free from raveling upon cutting, allowing no need to sew or hem the edges, thereby allowing less bulk at the peripheral edges of the protective chin cup cover assembly 10 and the peripheral edges of the protective forehead pad cover assembly 40 and avoids interference with installation and use of same. More particularly, having no need for hems or seams prohibits uneven bulkiness which can interfere with the application of fastening means. Further, the fleece material comes in a plurality of colors, with patterns, and with designs, from which the patient can select from and express their favorite colors and personal style. The wearer selected choice of fleece can accessorize an outfit or bed clothing or display a patient's favorite sports team colors or logos, or even cartoons.

The protective chin cup cover assembly 10 and the protective forehead pad cover assembly 40, according to the present invention, can closely imitate the contours of the orthodontic protraction headgear appliance 37 chin cup interface 38, and forehead pad interface 39, and more particularly the fleece protective chin cup cover assembly 10 and the forehead pad cover assembly 40 can closely imitate the facial contours of the chin and the forehead, respectively, and because of its relative softness and suppleness can conform to particular facial structures with minimum force, and without a tendency to fold or crease. Therefore, the protective chin cup cover assembly 10, and the forehead pad cover assembly 40 does not leave red marks, or indentations on the wearer's chin or forehead, respectively.

Figure 3:
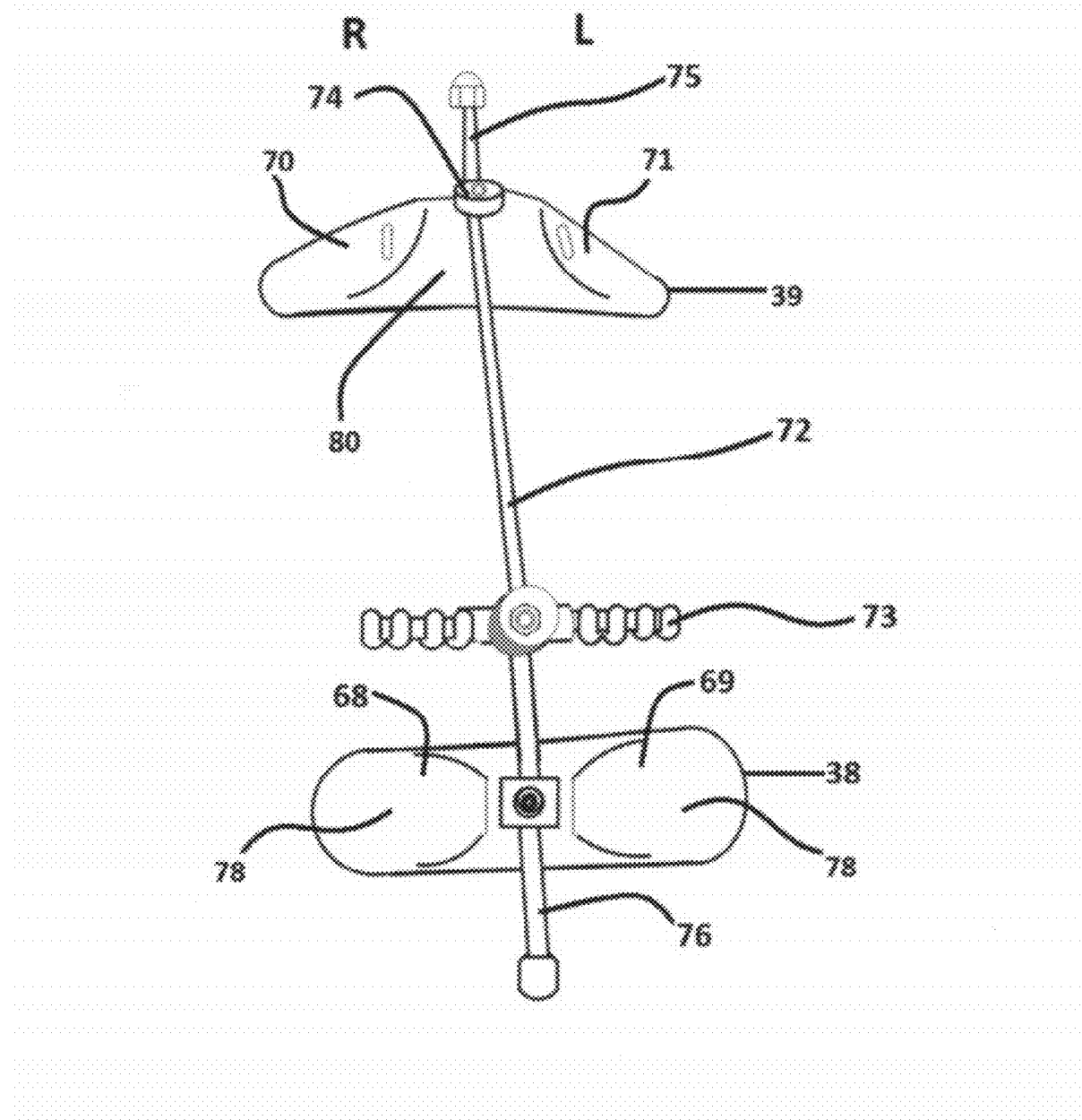
FIG. 3 is prior art of ventral side of a conventional orthodontic protraction headgear appliance typically used in the treatment of Class III Malocclusion disorder, illustrated for descriptive purposes and not claimed as part of the present invention.

FIG. 3 is prior art of a perspective view of the ventral side of a conventional orthodontic protraction headgear appliance 37 which is typically worn by an orthodontic patient during treatment of Class III Malocclusion disorder, which is the side facing out towards a viewer, and is illustrated for descriptive purposes and not claimed as part of the present invention. FIG. 4 is a prior art of a perspective view of the dorsal side of a conventional orthodontic headgear appliance 37, which is the side facing the wearer, and is illustrated for descriptive purposes and not claimed as part of the invention. As shown in FIGS. 3 and 4 a conventional orthodontic protraction headgear appliance 37 includes a chin cup interface 38, having a ventral side 78 and a dorsal side 77, and the chin cup interface 38 is configured with a right side member 68 and a left side member 69. The orthodontic protraction headgear appliance 37 also includes a forehead pad interface 39 having a ventral side 80 and a dorsal side 79 and the forehead pad interface is configured with a right side member 70 and a left side member 71. In addition, the orthodontic protraction headgear appliance 37 includes a vertical main frame 72 having a top end 75 and a bottom end 76, and along the vertical main frame is affixed a horizontal crossbar 73. Also, the forehead pad interface 39 includes a durable screw 74 which affixes the forehead pad interface to the vertical main frame 72. FIG. 5 is prior art of a side perspective view of conventional orthodontic protraction headgear appliance 37, illustrated for descriptive purposes and not claimed as part of the present invention, and as illustrated shows the horizontal crossbar 73 configured with elastic bands 81. In addition, FIG. 5 illustrates a side perspective view of a conventional orthodontic protraction headgear appliance 37 including a chin cup interface 38 showing chin cup left side member 69; and a forehead pad interface 39 with forehead pad left side member 70. The external chin cup interface 38 of the conventional orthodontic protraction headgear appliance 37 is manufactured with a hard rigid material, typically plastic, shaped to conform to a patient's curve of the chin to come in contact with the wearer's chin and to provide pressure thereon; and similarly the external forehead pad interface 39 is manufactured with a hard rigid material, typically plastic, shaped to conform to a patient's curve of the forehead to come in contact with the wearer's forehead and to provide pressure thereon. FIGS. 3, 4, 5, and 6, also, illustrate a chin cup interface 38 and a forehead pad interface 39 which comprises hard rigid plastic with no padding. As illustrated in FIG. 6 the headgear chin cup interface 38 and forehead pad interface 39 of an orthodontic protraction headgear appliance are pivotally positioned upon the wearer's face in a manner which allows pressure to be applied to the patient's chin and forehead. The chin cup interface 38 is pivotally positioned against the patient's chin to hold the chin cup while supporting the pull force applied by the elastic bands on the patient's teeth while said same elastic bands 81 are simultaneously attached to the horizontal crossbar 73 of the orthodontic protraction headgear appliance 37. Contemporaneously, the headgear forehead pad interface 39 is pivotally positioned upon the patient's forehead allowing a pressure force against the forehead sufficient to sustain the prescriptive force of the orthodontic protraction headgear appliance 37. The chin cup interface 38 and forehead pad interface 39 of the orthodontic protraction headgear appliance 37 have no covers to create a soft, comfortable, absorbing, cushioning, membrane between the patient's skin and the hard rigid plastic surfaces of a chin cup interface 38 and a forehead pad interface 39. Therefore, there is no enabling means to protect against the formation of deposits of saliva, mucous, mouth leakage, drool, skin flora and the cultivation of pressure sores, decubitus sores, irritation, cracking of skin, redness, microbial infection, discomfort, lingering facial indentations, facial suction marks, allergic reactions, and other skin disorders, on the patient's chin or forehead. Consequently, the need for a protective chin cup cover assembly 10 and forehead pad cover assembly 40, according to the preferred embodiment of the present invention, is apparent.

Protective Chin Cup Cover Assembly 10

A first aspect of the present invention, a protective chin cup cover assembly 10 as illustrated in FIGS. 1, 2, 7, 8, 11, 12, 15-19, 22-26(a)-(c), 32, 33, 34, 35, 36 and 37, discloses and claims a protective chin cup cover assembly 10 configured to be installed upon an external chin cup interface 38 of an external orthodontic protraction headgear appliance 37 and thereby provides a soft absorbent membrane between the patient's skin on the chin and the hard surface of the external chin cup interface 38. The chin cup cover assembly 10 provides a means to assuage discomforts presented by use of an external orthodontic protraction headgear appliance 37 to a wearer's facial skin at the site of the chin and underlying tissues and prevents the development of pressure sores, decubitus sores, lingering facial indentations, cracked skin, redness, breakouts, allergic reactions, minimizes mouth leaks, and when used maximizes compliance to wearing the orthodontic headgear appliance during treatment of Class III Malocclusion disorder. The protective chin cup cover assembly 10, according to the preferred embodiment of the present invention, discloses and claims a protective chin cup cover assembly 10, as illustrated in FIGS. 1, 2, 26a-b, 34, 35, 36, and 37 which surrounds and conceals the external orthodontic protraction headgear chin cup interface 38 of an orthodontic protraction headgear appliance 37 thereby providing a soft absorbent membrane shielding and protecting the wearer's skin and underlying tissues at the site of the wearer's chin, and which provides a means for impeding the negative elements and assuaging discomforts presented by use of an external orthodontic protraction headgear appliance 37, and particularly a chin cup interface 38, to a wearer's facial skin at the site of the chin and underlying tissues.

FIGS. 7, 11, and 15 illustrates a flat top planar view of the protective chin cup cover assembly 10 according to the preferred embodiment of the present invention with the obverse soft side 31 up towards the viewer. FIGS. 8 and 12 illustrates a flat planar view of the reverse side of the protective chin cup cover assembly 10, with the dull side 32 up towards the viewer. The protective chin cup cover 10, as illustrated in FIGS. 7 and 8 comprises a single body unit of soft flexible material 82 configured with predetermined dimensions, as described below, to surround the surface area of the external chin cup interface 38. Illustrated in FIGS. 7, 11, and 15, the soft flexible material 82 includes a top obverse surface with soft pile 31; and as illustrated in FIGS. 8 and 12, the soft flexible material 82 includes a reverse or underside surface which is dull 32 comprising a shorter length pile than its obverse side 31, such that the dull side still 32 maintains the soft absorbent flexible characteristic inherent of the fleece material 82. In the present invention, the fleece material 82 of the chin cup cover assembly preferably comprises 100% polyester fleece, but can also be manufactured using polar fleece, baby fleece, and the like, that comprises a soft obverse pile 31 and a dull reverse surface 32. In addition, the fleece material of the chin cup cover 82 is selected to exhibit high wicking characteristics such that it dries quickly while being worn by a wearer, especially while sleeping, so as to provide an absorption means for mouth leaks, perspiration, and other related oral fluids. The fleece material 82 of the chin cup cover assembly 10 is flexible, lightweight and made highly breathable, even when damp. Fleece is a soft, lightweight, flexible material and it retains much of its insulating powers even when wet, and it is highly breathable. Perspiration is able to readily pass through the fabric. It is machine washable and dries quickly. The preferable fleece material 82 is formed with a soft relatively upright pile that provides a soft comforting surface to the wearer and a soft stretchable fit to the external chin cup interface 38. Also, if desired, the fleece fabric 82 may be comprised in major part of recycled polyester plastics. The chin cup cover assembly 10 further comprises a soft fleece 82 stretchable material which is stretchable in at least two directions having two-way stretch extending along the lateral axis 30, as defined by phantom line 30, as illustrated in FIGS. 11 and 12. Also, if desired or needed, the fleece material 82 may be comprised with four-way stretch.

The chin cup cover assembly 10 aspect of the present invention is described in FIGS. 7, 11, 15-17, and 19 as the viewer is looking at the top planar view of the fleece material 82, therefore, directional words correspond to the viewer's right hand and the viewer's left hand, and the directional connotations assigned travel with the fleece fabric 82 of the chin cup cover assembly 10 throughout the illustrations presented herein.

Furthermore, as illustrated in FIG. 7 illustrates the chin cup cover assembly 10, according to the preferred embodiment of the present invention, is made from a single body unit of fleece material 82 generally rectangular double-arched in shape. This novel configuration of the orthodontic protraction headgear chin cup cover assembly 10 is further illustrated in FIGS. 7, 8, 11, 12, and 15. The protective chin cup cover assembly 10 is a single body unit of fleece material 82 having a soft obverse side 31 and a dull reverse side 32. The obverse side 31 of the fleece material 82 is the preferred side to be congruent with the wearer's chin which will provide a membrane to assuage the many discomforts of the external plastic chin cup interface 38 of the orthodontic protraction headgear appliance 37. It is recommended to mark this side as the obverse side with a removable tab or marking to guarantee consistency in manufacturing and configuration of the protective chin cup cover assembly 10.

In addition, the generally rectangular double-arched shaped fleece material 82 of the chin cup cover assembly 10 further when laid flat comprises two opposing lateral side edges, a left lateral side 14 and a right lateral side 15, and said two lateral opposing side edges 14 and 15 are joined to opposing longitudinal edges, a posterior longitudinal edge 16 and anterior double bilaterally symmetrical inverted U-shaped arched edges 23 and 24, as illustrated in FIGS. 7, 9, 11, and 12. The posterior longitudinal edge 16 is generally linear having two opposing arcuate corner edges which when joined to the two opposing lateral edges form two posterior arcuate opposing corners 35 and 36. In addition, anterior double-arched edges 23 and 24 borders double bilaterally-symmetrical inverted U-shaped arched flanges, a right anterior flange 17 and a left anterior flange 18; and all together forming a protective chin cup cover assembly 10 having a single body unit of fleece material having a generally rectangular-double arched shape, further having a longitudinal axis 29 and a lateral axis 30, as seen in FIGS. 11, 12, and 15.

In addition, as seen in FIGS. 7, 8, 11, and 12, the chin cup cover assembly 10 comprises a generally rectangular in shape posterior portion 12, and a generally rectangular double-arched anterior portion 11, and a generally rectangular chassis core portion 13 continuously disposed between the posterior portion 12 and anterior portion 11, and together all three portions 11, 12, and 13, are of predetermined dimensions and configuration in size sufficient for covering an external orthodontic protraction chin cup interface 38. As illustrated in FIGS. 7, 8, 11, 12, and 15 the anterior portion 11 further comprises double bilaterally-symmetrical inverted U-shaped anterior flanges 17 and 18, formed by a longitudinal cut 27, and flanges 17 and 18 disposed on a generally rectangular portion, and further each inverted U-shaped anterior flange 17 and 18 is disposed on either side of the longitudinal axis 29 forming a right anterior flange 17 and a left anterior flange 18.

Wherein, the right anterior flange 17 comprises two generally parallel lateral sides, an exterior right lateral side 21 and an interior left lateral side 22, joined by an inverted-U shape anterior edge 24; and the left anterior flange 18 comprises two generally parallel lateral sides, an exterior lateral left side 19 and an interior lateral right side 20, joined by an inverted U-shaped anterior edge 23.

As illustrated in FIGS. 22-26(a), 33, 34, 36, and 37, the posterior longitudinal edge 16 and the anterior arched flanges 17 and 18 of the chin cup cover assembly 10 are of a sufficient width to allow the chin cup cover assembly 10 to extend across the longitudinal width of the orthodontic protraction headgear chin cup interface 37. As illustrated in FIGS. 1, 2, 26(a), and 36, the lateral sides 14 and 15 of the chin cup cover assembly 10 are of sufficient length to allow the chin cup cover assembly 10 to fold entirely around the external chin cup interface 37 with allotment for anterior portion to overlap the posterior portion.

As illustrated in FIGS. 11 and 12 a longitudinal axis 29 extends through the chin cup cover assembly 10 from the longitudinal cut 27 between the inverted anterior U-shaped arched flanges 17 and 18 and the posterior longitudinal edge 16; and a lateral axis 30 extends through the midpoints of the two lateral side edges 14 and 15. The chin cup cover assembly 10, as noted above, comprises two arcuate posterior corner edges 35 and 36; and anterior arched flanges 17 and 18 with anterior arched-edges 23 and 24. The arcuate corners 35 and 36 and anterior arched edges 23 and 24 are preferred because the arched configuration averts otherwise curling of the edges of the chin cup cover assembly 10 during use.

Looking more particularly at FIGS. 7 and 11, a top planar view of the preferred embodiment of the protective chin cup cover assembly 10 is illustrated comprising a single body unit of fleece material 82 with the obverse soft side up 31 generally rectangular double-arched in shape having a chassis core portion 13 continually seamlessly joined to a posterior portion 12 and an anterior portion 11, all cut from a flat piece of fleece material 82. FIGS. 8 and 12, illustrates a planar view of the reverse dull side 32 of the chin cup cover assembly 10 facing up towards the viewer. The chassis core portion 13 is generally rectangle in shape and integrally seamlessly disposed between the posterior portion 12 and the anterior portion 11 and is the longest in length among the posterior 12 and anterior portion 11, and is configured with sufficient length and width of material to form a pleat 84, which is described below, which provides a means for two additional layers of membrane between the wearer's chin and the dorsal side of the hard surface of the chin cup interface 38. As illustrated within the chin cup cover assembly 10, a fold line is defined at phantom line F1 and two seam lines defined at phantom lines S1 and S2 which will described below in the formation of a pleat 84.

In addition, the chassis portion 13 is disposed between the posterior portion 12 and the anterior portion 11 such that the obverse surface 31 of the chassis core portion 13 defines the soft material membrane between the wearer's facial skin of the chin and the hard surface of the chin cup interface 38.

The posterior portion 12 is generally rectangular in shape and further configured with predetermined dimensions half the size of the anterior portion 11 and sufficient length and width of material to comprise a fastening means therein, preferably at least two buttons 25 and 26, and to cover a bottom portion of the ventral side 78 of the external chin cup interface 38. The anterior portion 11 is generally rectangular double-arched in shape and further configured with sufficient length and width to comprise therein two bilaterally-symmetrical inverted U-shaped flanges 17 and 18 wherein each flanged 17 and 18 further comprises a fastening means therein, preferably vertical reinforced button holes 25*a* and 26*a*, which corresponds to fastening means affixed to the posterior portion 12, preferably buttons 25 and 26. The anterior portion 11 is of sufficient size to cover a portion of the ventral side 78 of the external chin cup interface 38 and further to overlap the posterior portion 12 of the protective chin cup cover assembly 10 upon installation, as illustrated in FIGS. 1, 2, 26(*a*), and 36. The fastening means, preferably two buttons 25 and 26 with corresponding button holes 25*a* and 26*a* provides a means for securing the protective chin cup cover 10 to the external chin cup interface 38 and closing the protective chin cup cover assembly 10 around the external chin cup interface 38. In addition, the buttons 25 and 26 provide a decorative means to the chin cup cover assembly 10 and can resemble the eyes of a face presenting an aesthetic and humorous improvement on the medicinal appearance of the orthodontic protraction headgear appliance 37 which can improve compliance by the orthodontic patient to wear the orthodontic protraction headgear appliance 10.

In addition, the posterior portion 12 of the protective chin cup cover assembly 10, according to the preferred embodiment of the present invention comprises a horizontal aperture 28 or opening through in the surface of the soft fleece material 31 of the chin cup cover assembly 10 which extends through to the opposite dull surface 32 of the fleece material 82 of the chin cup cover 10. This aperture 28 is dimensionally constructed and pivotally positioned a short distance from seam line S2, as defined by phantom line S2, and intersects with the longitudinal axis 29 of the chin cup cover assembly 10, and is of sufficient size as to permit the insertion of the bottom end 76 of an external vertical main frame 72 of the external orthodontic protraction headgear appliance 37 into the horizontal aperture 28 which when the chin cup cover 10 is installed upon the external chin cup interface 38, as illustrated in FIGS. 22-25, 32, 33, 34, 35, and 36 will permit the chin cup cover 10 to be anchored thereon in the desired position and direction. The marginal edges of the horizontal aperture 28 are secured with sewn stiches as seen more clearly in FIG. 22. In addition, the horizontal aperture 28 prohibits the chin cup cover 10 from sliding off the external chin cup interface 38.

In the exemplary embodiment of the present invention, as illustrated in FIGS. 1, 2, 26(*a*), and 36, a fastening means, preferably two buttons 25 and 26, removably affixes the chin cup cover assembly 10 to the external orthodontic headgear chin cup interface 38. Each inverted U-shaped anterior flange 17 and 18 further comprises a pivotally positioned member of a fastening means, preferably vertical slit shaped apertures vertically cut therein, preferably button holes 25*a* and 26*a* configured a predetermined size such that they can receive a corresponding member of said fastening means, preferably buttons, 25 and 26, which are pivotally positioned and affixed therein to the posterior portion 12 of the chin cup cover assembly 10. The vertical apertures, or button holes 25*a* and 26*a* are reinforced at the marginal edges with sewn stitches, as clearly shown in FIGS. 23 and 25. The posterior portion 12 comprises a fastening means, preferably two buttons 25 and 26 laterally distanced from each other and affixed at a predetermined distance from the posterior longitudinal edge 16 and pivotally aligned with the corresponding vertical button holes 25*a* and 26*a* and further affixed to the top obverse side 31 of the fleece material 82 of the chin cup cover assembly 10. This configuration and alignment of the buttons 25 and 26 and the vertically aligned button holes 25*a* and 26*a*, enables the chin cup cover 10 when installed and in use to properly align around the external entire chin cup interface 38 of the orthodontic protraction headgear appliance 37 and allows for the buttons 25 and 26 to be exposed forward to be seen by the viewer, as illustrated in FIGS. 1, 2, 26(*a*), and 36. Moreover, the buttons 25 and 26 and button holes 25*a* and 26*a* will not be facing the wearer's chin.

The preferred fastening means are buttons 25 and 26 because they are easy to manipulate, provide secure fastening means, economical, and easy to replace. In addition, the buttons 25 and 26 can be used in a plurality of colors and designs and therefore add a decorative and fanciful design to the protective chin cup cover assembly 10. As illustrated in FIGS. 7, 11, and 15 each button hole 25*a* and 26*a* are cut within each anterior flange 17 and 18 pivotally positioned at a predetermined distance apart on the same lateral axis and pivotally positioned at a site generally in the center of each anterior flange 17 and 18 and pivotally aligned with the corresponding buttons 25 and 26 such that when the chin cup cover assembly 10 is installed on the headgear chin cup interface 38 the buttons 25 and 26 are juxtaposed on either side of the vertical mainframe 72 of the orthodontic protraction headgear appliance 37 when used and worn by the patient such that the buttons 25 and 26 mimic a face, as illustrated in FIGS. 1, 2, and 36.

As mentioned above, the anterior portion 11 of the protective chin cup cover assembly 10 includes a left anterior flange 18 and a right anterior flange 19 wherein each flange 18 and 19 includes a button hole 25a and 26a affixed thereto; and the posterior flange 12 includes corresponding buttons 25 and 26 affixed thereto for removably attaching or intraengaging the posterior portion 12 with each of the anterior flanges 18 and 19 to close the chin cup cover assembly 10 around the chin cup cover interface 38. As illustrated in FIGS. 1, 2, 26(a), and 36, together the two anterior flanges 18 and 19 of the protective chin cup cover assembly 10 define the top front cover of the protective chin cup cover assembly 10. Generally, the posterior portion 12 defines the bottom front cover of the protective chin cup cover assembly 10.

As further illustrated in FIGS. 15-21, and FIGS. 34 and 35 the chassis portion, further comprises a pleat 84 formed within, as described below, which defines the three layered membrane which is disposed between the skin of the wearer's chin and the dorsal side 77 of the hard surface of the external chin cup interface 38, as illustrated in FIGS. 26 (b)-(c), and 35.

Further as illustrated in FIGS. 24 and 25 the posterior portion 12 of the chin cup cover assembly folds up and over the bottom edge of the external chin cup interface 38 and covers generally the bottom portion of the chin cup interface 38 revealing the obverse soft side 31 of the chin cup cover fleece material 82 and the two buttons 25 and 26 affixed therein. Further as illustrated in FIGS. 24, 25, and 26(a) the left anterior flange 18 folds over the left shoulder member 69 of the external chin cup interface 38 revealing the obverse soft side 31 of the fleece material 82 and left button hole 25a; and the right flange 17 folds over the right shoulder member 68 of the external chin cup interface 38 revealing the obverse soft side 31 of the fleece material 82 and the right button hole 26a; and thereby covers a portion of the ventral side 78 of the external chin cup interface 38, revealing the obverse soft side 31 of the chin cup cover fleece material 82 and the fastening means, preferably at least two vertical button holes 25a and 26a. The chin cup cover assembly 10 fastening means, preferably at least two buttons 25 and 26 provides a means to fully open and close the chin cup cover assembly 10 around the external chin cup interface shoulder members 68 and 69, and provide for easy installing of the chin cup cover assembly 10 on and off the external chin cup interface 38, and also, the two buttons 25 and 26 provide a humorous embellishment which resemble the features of a face, and a secure fastening means to mount the protective chin cup cover assembly 10 thereon the external chin cup cover interface 38.

The side lateral openings 85 and 86 formed on each side of the chin cup cover assembly 10 remain open and unsealed, where right lateral opening 85 is illustrated in FIG. 1, and the left lateral opening 86 is identical, as illustrated in FIG. 26(c), to provide for proper aeration of the chin cup cover assembly 10 when the orthodontic protraction headgear appliance 37 is worn by the patient during treatment.

Pattern and Method of Construction of Protective Chin Cup Cover Assembly 10

FIGS. 7, 8, 11, and 12, illustrates in general the pattern or blank of the single body unit of material of fleece 82 which forms the protective chin cup cover assembly 10. FIGS. 7 and 11 illustrates a single body unit of fleece material 82 with the obverse side 31 facing up towards the viewer. FIG. 8 illustrates a single body unit of fleece material 82 as seen in FIG. 7 but with the reverse dull side 32 facing up towards the viewer. More particularly, FIG. 11 illustrates the pattern or blank of the single body unit of fleece 82 with the soft obverse side 31 facing up towards the viewer, which forms the protective chin cup assembly 10 further showing the predetermined dimensions of the protective chin cup cover assembly 10, according to the preferred embodiment of the present invention. FIG. 12 illustrates the reverse dull side 32 of FIG. 11 showing the reverse side of the fleece material 82 with dimensions, forming the protective chin cup cover assembly 10 according to the preferred embodiment of the present invention.

The protective chin cup cover assembly 10 is of predetermined measurements, as illustrated in FIGS. 11 and 12 such that when the chin cup cover 10 is maneuvered around the external chin cup interface 38 and the chin cup cover 10 folds over the posterior edges and the anterior edges of the external chin cup interface 38, the anterior flanges 17 and 18 of the protective chin cup cover 10 overlaps the posterior portion 12 of the chin cup cover assembly 10 on the ventral side 78 of the chin cup interface 38, and the posterior portion 12 underlaps the anterior flanges 17 and 18 on the ventral side of the chin cup interface 38, and thereby the protective chin cup cover assembly 10 completely covers the distal and ventral sides of the external chin cup interface 38, as illustrated in FIGS. 1, 2, 26(a) and 36.

Upon construction of the protective chin cup cover assembly 10, according to the preferred embodiment of the present invention, as illustrated in FIGS. 7, 11, and 15 a single piece of fleece material 82 forming the protective chin cup cover assembly 10 is disposed supine on a flat surface with the obverse soft side 31 facing up and the dull side down 32 congruent with the surface of the flat surface. The obverse soft side 31 of the fleece material 82 is the preferred side comprising sufficient pile, softness, cushion, and absorbency to enable the assuaging of the discomforts of the plastic chin cup of the orthodontic protraction headgear appliance 39. It is recommended to mark this side as the obverse soft side 31 with a removable tab or marking to guarantee consistency in manufacturing and configuration of the protective chin cup cover assembly 10. The fleece material 82 of the protective chin cup cover 10 assembly further comprising a generally rectangular double-arched shape with a length and width and thickness, as defined below, and further comprising two seam lines, defined at S1 and S2 therein such that the first seam line S1 is defined at a predetermined distance from the anterior double-arched edges 23 and 24, and a second seam line S2 defined at a predetermined distance from the posterior longitudinal edge 16; and thereby a single body unit is formed having an anterior double-arched portion 11 and posterior portion 12 joined by a chassis core portion 13 disposed therebetween; and having a longitudinal axis 29 and a lateral axis 30, as further illustrated in FIGS. 11 and 12. Within the anterior portion is a longitudinal cut 27; a horizontal aperture 28; and a fastening means, preferably two vertical button holes 25a and 26a. Within the posterior portion are two fastening means, preferably two buttons 25 and 26.

FIGS. 8, and 12, illustrate the reverse dull side 32 of FIGS. 7 and 11 illustrating the rectangular-double arched shape of the protective chin cup cover assembly 10 and substantially identical dimensions to FIGS. 7 and 11, according to the preferred embodiment of the present invention: except for the reverse dull side 32 reveals the affixing stitches at 34 and 35 of the two buttons 25 and 26, affixed to the dull side 32 of the fleece material 82 of the chin cup cover assembly 10.

The generally rectangular double-arched piece of fleece material 82 is further configured with predetermined measurements, as illustrated in FIGS. 11 and 12 which are preferred, because they correspond to conventional orthodontic protraction headgear chin cup interface 38 used in treatment of orthodontic patients with Class III Malocclusion disorders. When the fleece material 82 is cut upon construction of the protective chin cup cover assembly 10 it is preferred to cut the fleece material 82 with the direction of stretch extending in two opposing directions along the lateral axis 30 as defined by phantom line 30. This lateral direction of stretch is preferred because the stretch is therefore antagonist to the pull of the anterior flanges 17 and 18 and posterior portion 12 when urged towards each other longitudinally when stretched over and around the external chin cup interface 38 upon installation and thereby extending the life of the protective chin cup cover assembly 10.

The material forming the protective chin cup cover assembly 10 is preferably 100% polyester fleece, as explained above, because it does not ravel upon cutting, thereby there is no need to seam or hem the edges of the cover assembly, and therefore any extra bulkiness is avoided which may interfere with the posture of the chin cup cover assembly 10 when installed upon an external chin cup cover interface 38.

As illustrated in detail in FIGS. 11 and 12, the fleece material 82 which eventually forms the chin cup cover assembly 10 further comprises a predetermined width measuring substantially 3.5 inches in width along the posterior longitudinal edge 16, substantially 3.5 inches in width along the width of combined anterior double-arched edges 23 and 24 extending from lateral sides 21 to 19; and substantially 9.0 inches in length along the lateral side edges 14 and 15, according to the preferred embodiment of the present invention. The fleece material 82 is preferably substantially $\frac{1}{16}$-$\frac{2}{16}$ inches in thickness. The anterior portion 11 within the chin cup cover assembly 10 is configured with a predetermined measurement of substantially 3.5 inches in width and configured a predetermined distance of substantially 3.5 inches in length from the anterior longitudinal-arched edges 23 and 24 to seam line S1; posterior portion 12 is configured with a predetermined measurement of substantially 1.75 inches in length from the posterior longitudinal edge 16 to seam line S2 and substantially 3.5 inches in width; and chassis core portion 13 of the chin cup cover assembly 10, upon construction is configured with a predetermined measurement of substantially 3.75 inches in length extending from seam line S1 to seam line S2, and substantially 3.5 inches in width and thereby having more material than the anterior portion 11 and posterior portion 12 to allow for the formation of a pleat 84. The seam lines S1 and S2 are parallel and longitudinally spaced apart from each other a predetermined distance of substantially 3.5 inches such that upon folding the chassis core portion 13 along fold line F1, defined by phantom line F1, to form a pleat, the chassis core portion 13 is now generally in size proportionate to the dorsal side of the external chin cup interface 38, as illustrated in FIG. 34. Further, when the pleat 84 is formed and seam lines S1 and S2 stitched together, as illustrated in FIG. 16, in the manner to be described below, the chassis core portion 13 with pleat 84 thereupon measure substantially 1.78 inches in length and substantially 3.5 inches in width such that the pleat 84 provides additional two layers to the single membrane of the chassis core portion 13 forming a three layered membrane disposed on the chassis core portion 13 and thereby providing additional cushioning, buffering, absorbency, at the site of the wearer's chin and thereby providing maximum protection to the skin of the wearer at the site of the chin that would otherwise come into contact with the hard surface of the external orthodontic protraction chin cup interface 38.

As further illustrated in FIGS. 7, 8, 11, and 12, cutting between the anterior double-arched edges 23 and 24 is a substantially 1-1.50 inch(es) longitudinal cut extending therein the anterior portion 11 forming two bilaterally-symmetrical anterior inverted U-shaped flanges, a right anterior flange 17 and a left anterior flange 18, and each flange 17 and 18 generally inverted U-shaped having two generally parallel lateral sides joined to one anterior arched anterior edge. The right anterior flange 17 is formed by two lateral sides, an exterior right lateral side 21 and an interior left lateral side 22 joined by anterior arched-edge 24. The left anterior flange 18 is formed by two lateral sides, an exterior left lateral side 19 and interior right lateral side 20 joined by an anterior arched-edge 23.

Further, as illustrated in FIGS. 7, 8, 11, and 12, cutting throughin the top obverse soft surface 31 of the fleece material 82 through the reverse dull side 32 of the fleece material 82 forms a horizontal aperture 28 pivotally positioned a short distance below seam line S2 along the longitudinal axis 29 and extending in opposing directions along the lateral axis 30 forming a horizontal aperture 28 sufficient to allow a vertical main frame 72 of an orthodontic protraction headgear appliance 37 to pass throughin, as illustrated in FIGS. 22-25. The marginal edges of the horizontal aperture 28 are reinforced with sewn stitches along the apertures 28 marginal edges, as seen more clearly in FIG. 22.

With the obverse soft side 31 of the fleece material 82 facing up towards the viewer, a fastening means element, preferably at least two buttons 25 and 26 are laterally spaced a predetermined distance from each other pivotally aligned to corresponding fastening means; at least two button holes 25a and 26a, and the buttons 25 and 26 are affixed a short distance from the posterior longitudinal edge 16. It is important to affix the two buttons 25 and 26 to the obverse soft side 31 of the fleece material 82 because upon installation of the chin cup cover assembly 10 onto the external chin cup interface 38, the two buttons 25 and 26 are facing out towards the viewer from the ventral side 78 of the external chin cup interface 38 and, more importantly, not towards the wearer's chin.

In addition, at least two buttons 25 and 26 are preferred fastening means because upon installation of the protective chin cup cover assembly 10 to the external chin cup interface 10 the buttons 25 and 26 resemble eyes on a face with the bottom end 76 of the vertical main frame 72 resembling a tongue that can extend up and down within the chin cup cover assembly 10. This preferred configuration of the chin cup cover assembly 10 disguises the medicinal and harsh appearance of the external chin cup interface 38; and is humorous which promotes a friendlier looking orthodontic protraction headgear apparatus 37, and thereby the chin cup cover assembly 10 promotes increased compliance by an orthodontic patient to use the external orthodontic protraction headgear appliance, especially growing children and adolescents.

The protective chin cup cover assembly 10 upon construction further comprises two corresponding fastening means, as illustrated in FIGS. 7, 8, 11, and 12, preferably button holes 25a and 26a. Each button hole 25a and 26a is further configured and cut throughin the fleece material 82 with a substantially 1.0 inch generally vertical aperture pivotally positioned throughin each of the anterior flanges 17 and 18 such that a first vertical button hole 25a, is formed within the left anterior flange 18 by cutting a substantially 1.0 inch vertical cut through the top obverse soft surface 31 of the fleece material 82 throughin to the dull underside 32 of the fleece material 82 pivotally positioned at a distance substantially ¾ of an inch from the left exterior lateral side edge 19 extending into the left anterior flange 18 of the chin cup cover assembly 10 and substantially ¾ of an inch from the right lateral interior side 20 of the left anterior flange 18 and substantially ⅜ inch from the anterior longitudinal-arched edge 23 of the left anterior flange 18. Respectively a second vertical aperture, preferably a button hole 26a is formed within the right anterior flange 17 by cutting an approximately 1 inch vertical cut through the top obverse surface 31 of the fleece material 82 throughin to the dull underside 32 of the fleece material 82 pivotally positioned at a distance substantially ¾ of an inch distance from the right exterior lateral side edge 21 of the right anterior flange 17 and extending into the right anterior flange 17 of the chin cup cover assembly 10 and substantially ¾ inch from the left interior lateral side 22 of the right anterior flange 17 and substantially ⅜ inch from the anterior longitudinal-arched edge 24 of the right anterior flange 17. The apertures of the button holes 25a and 26a are reinforced by sewing stitches around the marginal edges of the apertures thereby forming two secure apertures or button holes 25a and 26a, as more clearly illustrated in FIG. 23, to removably intraengage two corresponding buttons 25 and 26 positioned within the posterior portion 12 of the chin cup cover assembly 10.

The protective chin cup cover assembly 10, according to the preferred embodiment of the present invention further comprises a unique pleat 84 configuration having a double layer which is disposed upon the chassis core portion 13 thereby forming three layers of absorbent membrane, as illustrated in FIGS. 18, 19(d), 20, 21, 34, and 35 which enables the protective chin cover assembly 10 to provide increased absorbency, cushioning, and buffering membrane between the wearer's chin and the hard plastic of the external chin cup interface 38 when wearing the orthodontic protraction headgear appliance 37.

Turning to FIGS. 15-20 the construction and formation of the double layered pleat 84 of the chin cup cover assembly 10 is illustrated. A pleat 84 is formed which will provide two additional layers disposed upon the membrane of the chassis core portion 13 of the chin cup cover assembly 10 which will provide increased absorbency, cushioning, membrane to the skin of the wearer's chin; provide additional absorption of mouth drool, liquids, and mouth leakage from a patient wearing the orthodontic protraction headgear appliance 37 especially during sleep when the orthodontic patient's mouth is likely to be open; and provide additional absorption of pressure against the wearer's chin and thereby prevent against the formation of pressure sores, facial indentations, cracked skin, breakouts, allergic reactions, and similar skin irritations, as noted above. As illustrated in FIGS. 15-19, with the obverse side 31 of the fleece material 82 facing up towards the viewer the fleece material 82 is folded at the fold line F1, as illustrated more particularly in FIGS. 15 and 19(a) and 19(b), and further the fleece material 82 is folded at the fold line F1 as defined by phantom line F1, configured at a predetermined distance medially between seam line S1 and seam line S2; such that the obverse soft side 31 of the posterior longitudinal edge 16 extends over the obverse soft side 31 of the chassis core portion 13 to be laid upon the obverse soft side 31 into the anterior portion 11a distance substantially of 1.75 inches from seam line S1, as indicated by phantom line S1. As a result of folding the fleece material 82 in this manner, two obverse soft sides 31 are facing each other, as illustrated from a side perspective in FIG. 20(a) and the dull side 32 of a portion of the fleece material 82 is exposed to the viewer as illustrated in FIGS. 15, 16, 19(b) and illustrated from a side prospective 20(a). The two soft obverse soft sides 31 meet each other at the seam lines S1 and S2 as further illustrated in FIGS. 15, 16, and 20(b); and seam lines S1 and S2 are affixed to each other by sewing them together with threaded stitches 90, as illustrated in FIGS. 16 and 20(c); and the posterior edge 16 is folded back at seam line S1 concealing the stitches of the affixed seam 90 and revealing the obverse soft side of the posterior portion 12 having two button 25 and 26, chassis core portion 13, and anterior flanges 17 and 18 having two button holes 25a and 26a, to the viewer, as illustrated in FIGS. 17, 19(c) and 20(d). On the reverse side 32 of the chin cup cover assembly as illustrated in FIGS. 18, 19(d) and 20(d) a pleat 84 is formed with the obverse soft sides 31 of the fleece material 82 forming the interior surfaces within the fold of the pleat 84 and with the dull side 32 of the fleece material 82 forming the exterior surfaces of the pleat 84 such that the pleat 84 formed further comprises a dull top side 32 and a dull underside 32 and two layers of interiorly folded soft fleece side 31 of material disposed upon the chassis core portion 13 thereby forming three layers of membrane to provide added absorbency, cushioning and buffering between the patient's chin and the hard surfaces of the external chin cup interface 38 as illustrated more particularly in FIGS. 18, 19(d), 21a-b, 34, and 35.

Further, as illustrated in FIGS. 18, 19(d), 20(a)-(c), and 21, the pleat 84 is formed such that its proximal end 89 is adjacent to the reverse dull side 32 of the chassis core portion 13 of the chin cup cover assembly 10 at the stitched seam line 90 formed at the meeting of seam line S1 and S2, and the pleat 84 is further folded forward from its proximal end 89 to its distal end 91 extending toward the reverse dull side 32 of anterior flanges 17 and 18 such that the pleat 84 is congruent with the dull side 32 of the chassis core portion 13 forming three layers of membrane, as illustrated in FIG. 21 an exploded side view of the pleat 84, and FIG. 34

FIGS. 17 and 19(c) illustrates the formed uninstalled chin cup cover assembly 10 with obverse soft side up towards a viewer, horizontal aperture 28, right anterior flange 17 having right vertical button hole 26a therein, left anterior flange 18 having left vertical button hole 25a therein, and buttons towards a viewer; and FIGS. 18 and 19(d) illustrates reverse of FIGS. 17 and 18, illustrating the formed uninstalled chin cup cover assembly 10 with dull side 32 up towards viewer ready, pleat 84, horizontal aperture 28, reverse side of affixed left button 33, reverse side of affixed right button 34, right anterior flange 17 having right vertical button hole 26a therein, left anterior flange 18 having right vertical button hole 25a therein, ready for installation upon an external chin cup interface 38.

A perspective side view sequence of constructing the pleat 84 is illustrated schematically in FIG. 20(a)-(c). The pleat 84 is constructed by folding the chassis portion 13 at fold line F1, as indicated by phantom line at F1, illustrated in FIG. 20a, with the obverse soft side 31 of the fleece material 82 facing each other to align the two lateral seam lines S1 and S2, indicated in phantom at S1 and S2 located at opposing ends of the chassis core portion 13 such that the dull surface of each seam line S1 and S2 are facing up towards the viewer. As well illustrated in FIG. 20(b) the two obverse soft sides 31 meet each other at said seam lines S1 and S2 and therefore are congruent to each other. The seam lines S1 and S2 are permanently sewn together to form stitched seam 90 with thread to anchor the proximal end 89 of the pleat 84 continuously with the dull side 32 of the chin cup cover assembly 10; the seam 90 is sewn along seam lines S1 and S2 from one lateral side 14 to the other lateral side 15, as illustrated in FIG. 20(b). In addition, a pleat 84 is formed comprising soft interior surfaces 31 and dull exterior surfaces 32 having a top side and an underside and an arcuate distal edge 91. The lateral side edges 87 and 88 of the pleat remain open and are not hemmed or seamed, as illustrated in FIGS. 18, 20, and 21, which allows for proper aeration around the wearer's chin; and assists in efficient washing and drying of the chin cup cover assembly, such that all surfaces can be reached for washing and drying. As illustrated in FIG. 18, and arrow defined by a, shows the pleat is open throughin from right lateral opening 87 of the pleat 84 to the left lateral opening 88 of the pleat 84.

The pleat 84 is folded down as illustrated in FIG. 20(c) such that the proximal end 89 of the pleat 84 is adjacent to the dull side 32 of the chin cup cover 10 laterally along the stitched seam 90 and the proximal end 89 extends to the distal end 91 of the pleat 84 along the longitudinal axis 29 towards the anterior portion 11 of the chin cup cover assembly 10. The dull 32 underside of the pleat 84 extends over the dull side 32 of the chassis core portion 13 of the chin cup cover assembly 10 and is congruent therewith and thereby foil is three layers of fleece membrane at the chassis portion 13, as illustrated in an exploded side view in FIG. 21a-b, and which will form the membrane between the wearer's chin and the hard surface of the external chin cup interface 38 of the orthodontic protraction headgear appliance 37, as illustrated in FIGS. 26(a) and 35.

Moreover, as a result of the construction and configuration of the pleat 84 within the chassis core portion 13 of the chin cup cover assembly 10 an unobstructed seamless obverse top soft surface 31 is maintained for the chin cup cover assembly 10 and more particularly, a three layered fleece membrane is formed at the chassis portion 13 which provides a three layer membrane for the chin cup cover which upon installation is positioned such that the folded pleat 84 side is congruent with the dorsal side 77 of the external chin cup interface 38 and the soft obverse unobstructed side 31 is congruent with the wearer's chin and thereby provides a three layered fleece membrane between the wearer's chin and the external chin cup interface 38, as illustrated in FIGS. 1, 34, 35, and 37.

As mentioned, the lateral sides 87 and 88 of the chin cup pleat 84 are open to enable increased aeration and circulation therein and provides access to the inside surface area of the pleat 84 for efficient washing and drying of the protective chin cup cover assembly 10. The pleat 84 comprises open non-seemed or non-hemmed edges to provide for better air circulation between the wearer's chin and the hard surface of the external chin cup interface 38, as illustrated in FIGS. 26(b)-(c), 34 and 35. It is also advantageous that the protective chin cup cover assembly 10 is manufactured with fleece material 84 which is air permeable and therefore supports an air permeable pleat 84, such that the skin of the chin remains relatively aerated. In addition, the pleat 84 provides extra cushion to the membrane between the patient's chin and the hard surface of the chin cup interface 38 thereby sustaining an improved seal with the chin thereby allowing the orthodontic protraction headgear appliance 37 and external chin cup interface 38 to deliver treatment more effectively.

In another embodiment of the chin cup cover assembly 10 with pleat 84, the lateral edges of the pleat 84 can be closed and reinforced by seams sewn along each of the lateral edges of the pleat 84. In another embodiment of the present invention, a soft foam pad configured in size slightly smaller than the interior of the pleat 84, can be inserted into the hollow of the pleat 84 and the lateral sides 87 and 88 of the pleat 84 can then be closed by seams sewn along each of the lateral edges 87 and 88 of the pleat 84, providing additional padding to the protective chin cup cover assembly 10 against the hard surface of the external chin cup interface 38.

It is advantageous to the protective chin cup cover assembly 10, according to the preferred embodiment of the present invention, that construction and manufacture of the protective chin cup cover assembly 10 is economical, straightforward, and uses a minimal amount of material and fastening means.

The completed uninstalled protective chin cup cover assembly 10 with the obverse soft side 31 up is illustrated in FIGS. 17 and 19(c), and with the dull reverse side 32 up in FIG. 18. As will be observed, in FIGS. 26(a) and 37 the obverse soft surface 31 of the chassis core portion 14 of the chin cup cover assembly 10 is soft, smooth, seamless, and unobstructed, to afford optimum comfort to the wearer. As a result of this construction, the obverse soft unobstructed side 31 of the chassis core portion 13 will be congruent to the wearer's facial skin on the chin, as shown in FIGS. 1, 26(a)-(b), 34, 35 and 37, and contemporaneously the folded pleat 84 on the reverse side 32 of the chassis core portion 13 will be congruent with the hard surface of the dorsal side 77 of the external chin cup interface 38. The chin cup cover assembly 10, as shown in FIGS. 35 and 37 has a smooth contour conformably fitting the external chin cup interface 38 contemporaneously conformably fitting the contours of the wearer's chin and thereby effective to mitigate friction and chaffing to the wearer's chin and consequentially preventing the development of lingering facial indentations, suction marks, cracked skin, redness, pressure sores, decubitus sores, and other skin disorders, and infection. Further, there are no overlapping stitches and thus no bulky multiple stitched points or areas in the obverse soft side 31 of chassis core portion 13, as illustrated in FIGS. 17, 32, 33, and 37. Consequently, the wearer will not be exposed to the irritation and chaffing that can be caused by ridged or ribbed stitching.

In addition, the three fleece layers disposed at the chassis portion 13, including a pleat 84, as illustrated in FIGS. 18, 19(d), 21(a)-(b), 34 and 35, of the chin cup cover assembly 10 are sufficient to provide additional cushioning to the chin and helps distributes the forces acting on the skin localized at contact points, thereby reducing the amount of friction in between the skin and the hard surface of the external chin cup interface 38; and thereby reduces chaffing, but does not interfere with the proper fit of the external chin cup interface 38 and the forces imposed by same. More particularly, it can be seen that the obverse soft 31 surface of the chin cup cover assembly 10 cushions the skin on the chin, including any pre-existing pressure sore that may be present on the chin.

Protective Forehead Pad Cover Assembly 40

FIGS. 1 and 2 illustrates a second aspect of the present invention, a protective forehead pad cover assembly 40 installed on an external forehead pad interface 39 of an external orthodontic protraction headgear appliance 37 as worn by an orthodontic patient during treatment of Class III Malocclusion disorder, according to the preferred embodiment of the present invention. The protective forehead pad cover assembly 40 provides a soft absorbent membrane between the wearer's forehead and the hard surface of the external forehead pad interface 39 and thereby provides a means to eliminate discomforts presented by use of an external orthodontic protraction headgear appliance 37 to a wearer's facial skin at the site of the forehead and underlying tissues to enable prevention of the development of cracked skin, redness, breakouts, allergic reactions, lingering facial indentations, suction marks, pressure sores, decubitus sores, suction marks, minimize perspiration and sweat leaks, and to maximize compliance to wearing the orthodontic protraction headgear appliance 37 during treatment of Class III Malocclusion disorder. The protective forehead pad cover assembly 40 surrounds and conceals the external forehead pad interface 39, as illustrated in FIGS. 1, 2, 31(a), 35-37, thereby shielding the wearer's head from the hard surface of the forehead pad interface 38 and thereby protects the wearer's forehead from the discomforts presented by wearing an orthodontic protraction headgear appliance 37.

FIGS. 2, 31(a) and 36 illustrates a front perspective view of the protective forehead pad cover 40 installed and in the closed position upon an external forehead pad interface 39 illustrating the obverse soft side 61 of the protective forehead pad cover assembly 40, and showing two buttons 55 and 56 intraengaged throughin corresponding two button holes 55a and 56a. FIG. 37 illustrates the rear view of FIG. 36, from the perspective of the wearer, showing the unobstructed soft obverse soft side 61 of the forehead pad cover assembly, which will be congruent with the wearer's forehead.

FIGS. 9, 10, 13, and 14 further illustrates the novel configuration of the headgear forehead pad cover assembly 40, according to the preferred embodiment of the present invention. The protective forehead pad cover assembly 40 as described in FIGS. 9 and 13, illustrates a top plan view of a forehead pad cover assembly 40 with the obverse soft side 61 of the fleece material 83 facing up towards the viewer, therefore, directional words correspond to the viewer's right hand and the viewer's left hand, and the directional connotations assigned travel with the fleece material 83 throughout the illustrations presented herein.

The protective forehead pad cover assembly 40, as illustrated in FIGS. 9, 10, 13, and 14, comprises a single body unit of soft flexible fleece material 83, configured with predetermined dimensions to surround the surface area of the external forehead pad interface 39 of an external orthodontic protraction appliance. As illustrated in FIGS. 9 and 13, the soft flexible fleece material 83 includes a top obverse surface with soft pile 61; and as illustrated in FIGS. 10 and 14, the soft flexible fleece material 83 includes a reverse or underside surface which is dull 62 comprising a shorter length pile than its obverse side, such that the dull side 62 maintains the soft absorbent flexible characteristic inherent of the fleece material 83. The protective forehead pad cover assembly 40 is manufactured with preferably fleece material 83 comprising 100% polyester fleece, but can be polar fleece, baby fleece, and the like, that comprises a soft obverse pile and a dull underside surface. The soft fleece material 83 is stretchable in at least two directions having two-way stretch extending along the lateral axis, defined by phantom line 60, as illustrated in FIGS. 13 and 14. Also, if desired or needed, the fleece material 83 may be comprised with four-way stretch. The advantages of using fleece in manufacturing of the protective forehead pad cover assembly 40 are the same as the protective chin cup cover assembly 10, as described above.

The forehead pad cover assembly 40, as illustrated in FIGS. 9, 10, 13 and 14, is made from a single body unit of fleece material 83 generally rectangular double-arched in shape, indicated generally at 40. FIGS. 9 and 13 illustrates a flat top planar view of the protective forehead pad cover assembly 40, according to the preferred embodiment of the present invention, with the obverse soft side 61 up towards the viewer. FIGS. 10 and 14 illustrates a flat planar view of the reverse side of the protective forehead pad cover assembly 40, with the dull side 62 up towards the viewer. The protective forehead pad cover assembly 40, as illustrated in FIGS. 9, 13, 10, and 14 comprises a single body unit of soft flexible material 83 configured with predetermined dimensions, as described below, to surround the surface area of the external forehead pad interface 39. Illustrated in FIGS. 9 and 13, the soft flexible material 83 includes a top obverse surface with soft pile 61; and as illustrated in FIGS. 10 and 14, the soft flexible material 83 includes a reverse or underside surface which is dull 62 comprising a shorter length pile than its obverse side 61.

Furthermore, as illustrated in FIGS. 9, 10, 13, and 14, the forehead pad cover assembly 40, is made from a single body unit of fleece material 83 generally rectangular double-arched in shape, which further illustrates the novel configuration of the protective forehead pad cover 40 to be installed upon the orthodontic protraction headgear chin cup interface 39, according to the preferred embodiment of the present invention. The obverse soft side 61 of the fleece material 83 is the preferred side to be congruent with the wearer's forehead comprising sufficient pile, softness, cushion, and absorbency to enable the elimination of the discomforts imposed on the orthodontic wearer by the external plastic forehead pad interface 39 of the orthodontic protraction headgear appliance 37. It is recommended to mark this side as the obverse side with a removable tab or marking to guarantee consistency in manufacturing and configuration of the protective forehead pad cover assembly 10.

In addition, the generally rectangular double-arched shaped fleece material 83 of the protective forehead pad cover assembly 40 further when laid flat comprises two opposing lateral side edges, a right lateral side edge 45 and a left lateral side edge 44, and said two lateral opposing side edges 44 and 45 are joined to opposing longitudinal edges, a posterior longitudinal edge 46 and longitudinal anterior double bilaterally-symmetrical arched edges 53 and 54. The posterior longitudinal edge 46 is generally linear having two opposing arcuate edges which when joined to the two opposing lateral edges 44 and 45 form two posterior arcuate opposing corners 66 and 67. In addition, anterior double bilaterally-symmetrical arched edges 53 and 54 borders double anterior bilaterally symmetrical inverted U-shaped arched flanges 48 and 47, a right anterior flange 47 and a left anterior flange 48; and all together foaming a generally single body unit of material having a rectangular-double arched shape to form the protective forehead pad cover assembly 40, further having a longitudinal axis 59, defined by phantom line at 59, and a lateral axis 60, defined by phantom line at 60, as illustrated in FIGS. 13 and 14.

In addition, as seen in FIGS. 9, 10, 13, and 14, the forehead pad cover assembly 40 comprises a generally rectangular in shape posterior portion 42, and a generally rectangular-double-arched anterior portion 41, and a generally rectangular chassis core portion 43 continuously disposed between the posterior portion 42 and anterior portion 41, and together all three portions 41, 42, and 43 are of predetermined dimensions and configuration in size sufficient for covering an external orthodontic protraction forehead pad interface 37. As illustrated in FIGS. 9, 10, 13, and 14, the anterior portion 41 further comprises double bilaterally symmetrical inverted-U shaped anterior flanges 47 and 48 formed by a longitudinal cut defined at 57, wherein anterior flanges 47 and 48 are disposed on a generally rectangular portion; and further each inverted U-shaped anterior flange 47 and 48 is disposed on either side of the longitudinal axis 59, defined by phantom line 59, forming a right anterior flange 47 and a left anterior flange 48.

The right anterior flange 47 further comprises two generally parallel lateral sides, an exterior right lateral side 51 and an interior left lateral side 52, joined by an inverted-U shape anterior edge 54; and the left anterior flange 48 further comprises two generally parallel lateral sides, an exterior lateral left side 49 and an interior lateral right side 50, joined by an inverted U-shaped anterior edge 53.

As illustrated in FIGS. 1, 2, 28, 29, 30, 31(*a*), 33, 34 36, and 37, the posterior longitudinal edge 46 and the anterior arched flanges 47 and 48 of the forehead pad cover assembly 40 are of a sufficient width to allow the forehead pad cover assembly 40 to extend across the longitudinal width of the orthodontic protraction headgear forehead pad interface 38. As illustrated in FIGS. 1, 2, 31, 33, 36, and 37, the lateral sides 44 and 45 of the protective pad cover assembly 40 are of sufficient length to allow the forehead pad cover assembly 40 to fold entirely around the external forehead pad interface 38 with allotment for anterior portion 41 to overlap the posterior portion 42.

As illustrated in FIGS. 13 and 14 a longitudinal axis 59, as defined by phantom line 59, extends through the longitudinal cut 59 between the two anterior bilaterally-symmetrical inverted U-shaped flanges 47 and 48 to the posterior longitudinal edge 46; and a lateral axis 60, defined by phantom line 60, extends through the midpoints of the two lateral side edges 44 and 45. The protective forehead pad cover assembly 40, as noted above, comprises two arcuate posterior corner edges 66 and 67; and anterior inverted U-shaped arched flanges 47 and 48 with arched anterior edges 53 and 54. The arcuate corners 66 and 67 and arched anterior edges 53 and 54 are preferred because the arched configuration averts otherwise curling of the edges of the forehead pad cover assembly 40 during use.

Looking more particularly at FIGS. 9 and 13, a forehead pad cover assembly 40, is illustrated showing a top planar view of the preferred embodiment of the protective forehead pad cover assembly 40 comprising a single body unit of fleece material 83 with the obverse soft side up 61 generally rectangular double-arched in shape having a chassis core portion 43 continually seamlessly joined to a posterior portion 46 and an anterior portion 42, all cut from a flat piece of fleece material 83. FIGS. 10 and 14, illustrates a planar view of the reverse dull side 62 of the forehead pad cover assembly 10 facing up towards the viewer. The chassis core portion 43 is generally rectangle in shape and integrally seamlessly disposed between the posterior portion 42 and the anterior portion 41. The anterior portion 41 is the longest in length among the posterior 42 and chassis portion 43. The chassis core portion 43 is configured with sufficient length and width of material to form a membrane which is positioned between the wearer's forehead and the dorsal side 79 of the hard surface of the forehead pad interface 39, as illustrated in FIGS. 1, 2, 28, 31(*b*)-(*c*), 33, 34, 35, and 37. Further, the chassis core portion 43 is disposed between the posterior portion 42 and the anterior portion 41 such that the chassis core portion 43 defines the cover that extends over the dorsal side 79 of the external forehead pad interface 39, as illustrated in FIGS. 27-30, 31(*b*)-(*c*), 33, 34, and 37, and is maneuvered to enable the soft obverse soft side 61 of the chassis portion 43 to provide a soft, absorbent, cushions, unobstructed membrane between the wearer's facial skin of the forehead and the hard surface of the external forehead pad interface 39, as illustrated in FIG. 37.

The posterior portion 42 is generally rectangular in shape and further configured with predetermined dimensions smaller in size of the anterior portion 41 and chassis core portion 43 and sufficient length and width of material to comprise a fastening means therein, preferably at least two buttons 55 and 56, and sufficient in size to cover a bottom portion of the ventral side 80 of the external forehead pad interface 39. The anterior portion 41 is generally rectangular double-arched in shape and further configured with sufficient length and width to comprise therein two bilaterally-symmetrical inverted U-shaped flanges 48 and 47 wherein each flange 48 and 47 further comprises a fastening means therein, preferably vertical reinforced button holes 55*a* and 56*a*, which corresponds to fastening means affixed to the posterior portion 42, preferably at least two buttons 55 and 56. The anterior portion 41 is of sufficient size to cover a portion of the ventral side 80 of the external forehead pad interface 39 and further to overlap the posterior portion 12 of the protective forehead pad cover assembly 40 upon installation, as illustrated in FIGS. 1, 2, 31(*a*)-(*c*), and 36. The fastening means, preferably at least two buttons 55 and 56 with corresponding button holes 55*a* and 56*a* provides a means for securing and closing the protective forehead pad cover assembly 40 upon installation to an external forehead pad interface 39. In addition, the buttons 55 and 56 provides a decorative means to the forehead pad cover assembly 40 and can resemble the eyes of a face presenting an aesthetic and humorous improvement on the medicinal appearance of the orthodontic protraction headgear appliance 37, and therefore increase compliance in use by orthodontic patients.

In addition, the posterior portion 42 of the protective forehead pad cover assembly 40, according to the preferred embodiment of the present invention, comprises a vertical aperture 58 or opening through in the surface of the soft side 61 of the fleece material 83 of the forehead pad cover assembly 40 which extends through to the opposite dull surface 62 of the fleece material 83 of the forehead pad cover assembly 40. This aperture 58 is dimensionally constructed and pivotally positioned a short distance below the vertical longitudinal cut 57 and intersects with the longitudinal axis 59 of the forehead pad cover assembly 40, so as to permit the insertion of the top end 75 external vertical main frame 72 of the external orthodontic protraction headgear appliance 37 into the vertical aperture 58 which when the forehead pad cover assembly 40 is installed upon the external forehead pad interface 39, as illustrated in FIGS. 27, 28, 29, 30, 31, 32, 33, 34, 35, 36, and 37 will permit the forehead pad cover assembly 40 to be anchored thereon in the desired position and direction. The marginal edges of the vertical aperture 58 are secured with sewn stiches, as more clearly illustrated in FIG. 9. In addition, the vertical aperture 58 prohibits the forehead pad cover assembly 40 from sliding off the external forehead pad interface 39.

In the exemplary embodiment of the present invention, a fastening means, preferably buttons 55 and 56 removably affixes the protective forehead pad cover assembly 40 to the external forehead pad interface 39. Each inverted U-shaped anterior flange 47 and 48 further comprises a pivotally positioned member of a fastening means, preferably vertical slit shaped apertures vertically cut therein, preferably button holes. As illustrated in FIGS. 9, 10, 13 and 14, right anterior flange includes a vertical button hole 56*a*, and left anterior flange 48 includes a vertical button hole 55*a* configured a predetermined size such that they can receive a corresponding member of said fastening means, preferably buttons, 56 and 55, which are pivotally positioned and affixed therein to the posterior portion 42 of the forehead pad cover assembly 40. The vertical apertures, or button holes 56*a* and 55*a* are reinforced at the marginal edges with sewn stitches, as seen more clearly in FIGS. 9 and 30. The posterior portion 42 comprises a fastening means, preferably two buttons 55 and 56 laterally distanced from each other and affixed at a predetermined distance from the bottom posterior longitudinal edge 46 and pivotally aligned with the corresponding vertical button holes 55*a* and 56*a* and further affixed to the top obverse side 61 of the fleece material 83 of the protective forehead pad cover assembly 40. This configuration and alignment of the buttons 55 and 56 and the vertically aligned button holes 55*a* and 56*a*, enables the forehead pad cover assembly 40, when installed and in use, to properly align around the external entire external forehead pad interface 39 of the orthodontic protraction headgear appliance 37, and allows for the buttons 55 and 56 to be exposed forward to be seen by the viewer, as illustrated in FIGS. 1, 2, 31(a) and 36. Moreover, the buttons 55 and 56 and button holes 55a and 56a will not be facing the wearer's forehead when the patient is wearing the orthodontic protraction headgear appliance 37 during treatment.

The preferred fastening means are two buttons 55 and 56 because they are easy to manipulate, provide secure fastening means, economical, and easy to replace. In addition, the two buttons 55 and 56 can be used in a plurality of colors and designs and therefore add a decorative and fanciful design to the protective forehead pad cover assembly 40. As illustrated in FIGS. 9, 10, 13, and 14 each button hole 55a is cut within anterior flange 48 and button hole 56a is cut within anterior flange 47 pivotally positioned at a predetermined distance apart on the same lateral axis 60 and pivotally positioned at a site generally in the center of each anterior flange 48 and 47 pivotally aligned with the corresponding buttons 55 and 56 such that when the forehead pad cover assembly 40 is installed on the external forehead interface 39 the buttons 55 and 56 are juxtaposed on either side of the vertical mainframe 72 of the orthodontic protraction headgear appliance 37 when used and worn by the patient such that the buttons 55 and 56 mimic a face, as illustrated in FIGS. 1, 2, 31(a) and 36. In addition, this configuration and predetermined positioning of the two buttons 55 and 56 in relation to the corresponding button holes 55a and 56a enables the anterior flanges 47 and 48 to overlap the posterior portion 42, and for the posterior portion 42 to underlap the anterior flanges 47 and 48 upon installation of the forehead pad cover assembly 40 to an external forehead pad interface of an orthodontic protraction headgear appliance 37.

The anterior portion 41, as described above, includes a left anterior flange 48 and a right anterior flange 47 wherein each flange 48 and 49 includes a button hole 55a and 56a affixed thereto; and the posterior portion 42 includes corresponding buttons 55 and 56 affixed thereto for attaching the posterior portion 42 with each of the anterior flanges 48 and 49 to close the forehead pad cover assembly 40 around the external forehead interface 39. As illustrated in FIGS. 1, 2, 31 (a) and 36, generally together the two anterior flanges 47 and 48 of the protective forehead pad cover assembly 40 define the top front cover of the protective chin cup cover assembly 40; and generally the posterior portion 42 defines the bottom front cover of the protective forehead pad cover assembly 40 as illustrated in FIGS. 28-31 and 36; and as illustrated in FIGS. 28, 31(b)-(c), 33, 34, 35, 37 the chassis core portion 43 defines the absorbent membrane disposed between the wearer's forehead and the dorsal side 79 of the hard plastic of the external forehead pad interface 39.

Further as illustrated in FIGS. 30, 31, and 36 the posterior portion 42 folds over and up the bottom edge of the external forehead pad interface 39 and covers generally the bottom portion of the forehead pad interface 39 revealing the obverse soft side 61 of the forehead pad cover fleece material 83 and the two buttons 55 and 56 affixed therein. Further as illustrated in FIGS. 29, 30, 31 and 36 the left anterior flange 48 folds over the left shoulder member 71 of the external forehead pad interface 39 revealing the obverse soft side 61 of the fleece material 83 and a left button hole 55a; and the right flange 47 folds over the right shoulder member 70 of the external forehead pad interface 39 revealing the obverse soft side 61 of the fleece material 83 and the right button hole 56a; and thereby covers a portion of generally the top portion of the ventral side 80 of the external forehead pad interface 39, revealing the obverse soft side 61 of the forehead pad cover fleece material 83 and the fastening means, preferably at least two vertical button holes 55a and 56a. The protective forehead pad assembly 40 fastening means, preferably at least two buttons 55 and 56 provides a means to fully open and close the forehead pad cover assembly 40 around the external chin cup interface shoulder members 70 and 71, and provide for easy installing of the chin cup cover assembly 40 on and off the external forehead pad interface 39, and also, the two buttons 55 and 56 provide a fanciful embellishment which resemble the features of a face, and a secure fastening means to mount the forehead pad cover assembly 40 thereon the external forehead pad cover interface 39.

The right side lateral openings 92 and left lateral side opening 93 formed on each side of the forehead pad cover when the forehead pad cover assembly 40 remain open and unsealed to provide for proper aeration of the forehead pad cover assembly 40 when the orthodontic protraction headgear appliance 37 is worn by the patient during treatment. Right lateral side opening 92 is open as illustrated in FIGS. 1 and 31(b), and left lateral side is open and illustrated in FIG. 31(c).

As mentioned, and illustrated each anterior flange 48 and 47 comprises a pivotally positioned member of a fastening means, preferably slit shaped apertures or button holes 55a and 55b vertically cut therein, configured a predetermined size such that they can receive a corresponding member of said fastening means, preferably buttons 55 and 56, which are pivotally positioned and affixed therein to the posterior portion 42 of the forehead pad cover assembly 40. The button holes 55a and 56a are reinforced at the marginal edges with sewn stitches, as more clearly illustrated in FIG. 9. The posterior portion 42 comprises a fastening means, preferably two buttons 55 and 56 laterally distanced from each other and affixed on the obverse soft side 61 of the fleece material 83 at a predetermined short distance above the bottom posterior edge 46 and pivotally positioned aligned with the corresponding button holes 55a and 56a located within each anterior flange 48 and 47 affixed to the top obverse soft side 61 of the material 83.

In addition, as illustrated in FIGS. 9, 10, 13, 14, 27-34, the forehead pad cover assembly 40, according to the preferred embodiment of the present invention comprises a vertically aligned oval aperture 58 or opening throughin the surface of the soft fleece material 83 of the protective forehead pad cover assembly 40 which extends through to the opposite dull surface 62 of the fleece material 83 of the forehead pad cover assembly 40. The marginal edges of the vertically aligned oval aperture 58 are secured with sewn stitches, as more clearly shown in FIG. 9. This vertically aligned aperture 58 is dimensionally constructed of sufficient size, and pivotally positioned a short distance below the longitudinal cut line 57, such that the insertion of an external vertical main frame 72 of the external orthodontic headgear appliance 37 is permitted throughin the vertical aperture 58 when the forehead pad cover assembly 40 is installed onto the orthodontic protraction headgear appliance 37, and thereby the forehead pad cover assembly 40 is anchored thereon in the desired position and direction having the top end 75 of the vertical main frame 72 centered therebetween the left anterior flange 48 and the right anterior flange 47 of the forehead pad cover assembly 40, as illustrated in FIGS. 27, 29, 30, 31a, 32, 33, and 36. In addition, the vertical aperture 58 is a means for anchoring the forehead pad cover 40 in the desired position and direction on the external vertical main frame 72 and to move accordingly as the external vertical main frame 72 is moved in an up and down direction. Moreover, the vertical oval aperture 58 prohibits the forehead pad cover 40 from sliding off the external forehead pad interface 40.

As illustrated in FIGS. 9, 10, 13, 14, 27, 28, 29, 30, 32, 33, 34, and 35 the forehead pad cover assembly 40 further comprises a V-shaped marginal dart cut-out 65 throughin the posterior marginal edge 46 comprising a predetermined size to allow an external screw 74 of the orthodontic protraction headgear appliance 37 to pass therein, as more particularly illustrated in FIG. 30 upon installation of the forehead pad cover 40 to the external forehead pad interface member 39. The V-shaped marginal dart 65 is pivotally positioned along the posterior marginal edge 46 along the longitudinal axis 59 as indicated by phantom line 59.

Generally, as illustrated in FIGS. 9, 10, 13 and 14, the chassis core portion 43 includes lateral side edges 44 and 45 continuous with the posterior portion 42 and the anterior portion 41 and remain unreamed or unhemmed such that the chassis core portion 43 defines a pair of lateral aeration openings 92 and 93 for an external forehead pad interface 39 when the protective forehead pad cover assembly 40 is in use, as illustrated in FIGS. 1, 2, 31(a)-(c), 36 and 37. In addition, the chassis core portion 43 is disposed between the posterior portion 42 and the anterior portion 41 such that the obverse soft surface 61 of the chassis core portion 43 defines the soft material membrane between the wearer's facial skin of the forehead and the hard surface of the forehead pad interface 39, and the chassis core portion 43 covers the dorsal side of the external forehead pad interface 39 as illustrated in FIGS. 27-30, 31(b)-(c), 33, and 37.

Further as illustrated in FIG. 30 the posterior portion 42 folds over the bottom edge of the external forehead pad interface 39 and upwardly towards the ventral side 80 of the external forehead pad interface 39 and covers generally a bottom portion of the forehead pad interface 39 while revealing the obverse soft side 61 of the forehead pad cover fleece material 83 and the two buttons 55 and 56 affixed thereon. In addition, the forehead pad cover assembly 40 is maneuvered such that the V-shaped dart cut-out 65 is aligned to receive the durable screw 74 of the external forehead interface 39 to allow for a symmetrical snugly fit forehead pad cover assembly 40. Further, as illustrated in FIGS. 29, 30, and 31 the left anterior flange 48 folds over the left shoulder member 71 of the external forehead pad interface 39 and downwardly towards the posterior portion 42 of the forehead cover assembly 40, thereby revealing the obverse soft side 61 of the fleece material 83 and the button hole 55a therein; and the right flange 47 folds over the right shoulder member 70 of the external forehead pad interface 39 and downwardly towards the posterior portion of the forehead pad cover assembly 39, thereby revealing the obverse soft side 61 of the fleece material 83 and the button hole 56a therein; and thereby covers substantially the top portion of the ventral side 80 of the forehead pad interface 39. The posterior portion 42 of the forehead pad cover assembly 40 is secured to each of the anterior flanges 47 and 48 by inserting the affixed left button 55 through its corresponding left button hole 55a affixed within the left anterior flange 48; and similarly inserting the affixed right button 56 into the corresponding right button hole 56a affixed within the right anterior flange 47. As illustrated in FIGS. 1, 2, 31(a) and 36 the forehead pad cover assembly 40 is now installed and closed around the external forehead pad interface 39 of the external orthodontic protraction headgear appliance 37.

The forehead pad cover assembly 40 fastening means, preferably at least two buttons 55 and 56 provides a means to fully open and close the front thereof, and provide for easy installing of the forehead pad cover assembly 40 on and off the orthodontic protraction headgear forehead pad interface 39; and the buttons 55 and 56 provides a fanciful embellishment which resemble the features of a face; and the buttons 55 and 56 provides a secure fastening means to mount the protective forehead pad cover assembly 40 thereon the external forehead pad interface.

In another embodiment of the protective forehead pad cover assembly 40, a two layered pleat can be configured at the chassis core portion 43, similar to the pleat 84 configured within the protective chin cup cover assembly 10.

Pattern for Forehead Pad Cover 40

FIGS. 9, 10, 13, and 14 illustrates the pattern or template of the single body unit of material of fleece 83 which foil is the protective forehead pad cover assembly 40. FIG. 9 illustrates a single body unit of fleece material 83 used in the manufacture of the protective forehead pad cover assembly 40 with the obverse side 61 facing up towards the viewer. FIG. 10 illustrates a single body unit of fleece material 83 used in manufacture of the protective forehead pad cover assembly as seen in FIG. 9 with the reverse dull side 62 facing up towards the viewer. More particularly, FIG. 13 illustrates the pattern or blank of the single body unit of fleece material 83 with the soft obverse side 61 facing up towards the viewer, which forms the protective forehead pad cover assembly 10 further showing the predetermined dimensions of the protective forehead pad assembly 40, according to the preferred embodiment of the present invention. FIG. 12 illustrates the reverse dull side 62 of FIG. 11 of the preferred embodiment of the protective forehead pad cover assembly 40 showing the predetermined dimensions of the forehead pad cover 40 and illustrating back side of affixed right button 64, and showing back of affixed left button 63.

The protective forehead pad cover assembly 40 is of predetermined measurements such that when the forehead pad cover 40 is installation on an orthodontic protraction headgear appliance 37 the posterior portion 42 folds over the posterior edge 46 of an external forehead pad interface 39, and the anterior flanges 48 and 47 fold over the anterior edges of an external forehead pad interface 39, and the chassis core portion 43 of the protective forehead pad assembly 40 completely covers the dorsal 79 side of an external forehead pad interface, and the anterior flanges 48 and 47 covers substantially the ventral side 80 of the external forehead pad interface 39 such that the anterior flanges 48 and 47 overlaps the posterior portion 42, and the posterior portion 42 underlays the anterior flames 47 and 48 of the forehead pad cover assembly 40, and thereby the external forehead pad interface 39 is completely covered.

Upon construction of the protective forehead pad cover assembly 40, according to the preferred embodiment of the present invention, as illustrated in FIGS. 9 and 13 a single piece of fleece material 83 is disposed supine on a flat surface with the obverse soft side 61 facing up and the dull side 62 facing down congruent with the flat surface. The obverse soft side 61 of the fabric is the preferred side comprising sufficient pile, softness, cushion, and absorbency to enable the assuaging of the discomforts of the plastic forehead pad interface 39 of the orthodontic protraction appliance 37. It is recommended to mark this side as the obverse side 61 of the fleece material 83 with a removable tab or marking to guarantee consistency in manufacturing and configuration of the headgear forehead pad cover 40. The protective forehead pad cover assembly 40 further comprising a generally rectangular double-arched shape with a length and width and thickness, and further comprising two fold lines therein; the first fold line FL-1 is defined at phantom line FL-1 a predetermined distance from the longitudinal posterior edge 46, and a second fold line FL-2 is defined at a predetermined distance from longitudinal posterior edge 46; and thereby a single body unit is formed having an anterior portion 41 and posterior portion 42 joined by a chassis core portion 43 disposed therebetween. Within the anterior portion 41 is a longitudinal cut 57 forming two anterior inverted U-shaped flanges, right anterior flange 47 and left anterior flange 48; a vertical aperture 58; and two vertical button holes 55a and 56a. Within the posterior portion are two buttons 55 and 56; and a V-shaped dart cut out 65.

FIGS. 10 and 14 illustrate the reverse dull side 62 of FIGS. 9 and 13 illustrating the rectangular double-arched shape of the protective forehead pad cover assembly 40 and substantially identical dimensions to FIGS. 7 and 11 and the reverse dull side 62 reveals the affixing threaded stitches at 63 and 64 at the back side of the two buttons 55 and 56.

The generally rectangular double-arched piece of fleece material 83 is further configured with predetermined measurements which are preferred because they correspond to conventional orthodontic protraction headgear forehead pad interface 39 used in treatment of orthodontic patients with Class III Malocclusion disorders. When cut upon construction of the protective forehead pad cover assembly 40 it is preferred to cut the fleece material 83 with the direction of stretch extending in two opposing directions along the lateral axis 60 as defined by phantom line 60 as illustrated in FIGS. 13 and 14. This lateral direction of stretch is preferred because the stretch is therefore antagonist to the pull of the anterior flanges 48 and 47 when urged toward the posterior portion 42 upon installation of the forehead pad cover 40 to the external forehead pad interface 39 and thereby extending the life of the protective forehead pad cover assembly 40. The material 83 is preferably fleece, as explained above, because it does not ravel upon cutting, thereby there is no need to seam or hem the edges of the protective forehead pad cover assembly 40 and comes in a plurality of colors and designs which the wearer can select to express their individual style. In addition, the fleece is soft, flexible, breathable, absorbent, has wicking properties, and maintains its shape when wet.

As illustrated more particularly in FIGS. 13 and 14 the fleece material 83 which eventually forms the forehead pad cover assembly 40 further comprises a predetermined width along the posterior longitudinal edge 46 measuring substantially 3.5 inches in width and comprises a predetermined width along the total anterior longitudinal double arched-edges 53 and 54 extending from left lateral side 44 to right lateral side edge a width of substantially 3.5 inches; and substantially 4.25 inches in length extending therebetween from the posterior longitudinal edge 46 to the anterior double-arched edges at 53 and 54; and substantially 1/16-2/16 in thickness.

As further illustrated in FIGS. 13 and 14 the anterior portion 41 within the forehead pad cover assembly 40 is configured with a predetermined measurement of substantially 3.5 inches in width and configured a predetermined distance measuring substantially 2.0 inches in length from the anterior double-arched edges to fold line FL1, as defined by phantom line at FL1; and the posterior portion 42 is configured with a predetermined width of substantially 3.5 inches and with a predetermined measurement of substantially 0.75 inches in length from the posterior longitudinal edge 46 to fold line FL2, as defined by phantom line at FL2. The chassis core portion 43, upon construction is configured with a predetermined measurement of substantially 1.5 inches in length extending longitudinally from fold line FL1 to fold line FL2. The fold lines FL1 and FL2 are parallel and longitudinally spaced apart from each other a predetermined distance of substantially 1.5 inches such that generally an anterior portion 41 is formed that is longer in length than the posterior portion 42 and chassis core portion 43; and forms a chassis core portion 43 that is longer in length than the posterior portion 42. Further, when the protective forehead pad cover assembly 40 is installed upon the external forehead pad interface 39, the dull side 62 of the chassis core portion 43 covers and is congruent with the dorsal side 79 of the external forehead pad interface 39, as illustrated in FIGS. 28, 30, 31(b)-(c), 34, 35, and 37 concurrently the soft unobstructed obverse side 61 is congruent with the wearer's skin providing a membrane between wearer's forehead and the external forehead pad interface 39 and thereby providing additional cushioning, buffering, absorbency, at the site of the wearer's forehead and thereby providing maximum protection to the skin of the wearer at the forehead that would otherwise come into contact with the hard surface of the external orthodontic protraction forehead pad interface 39. In addition, the anterior flanges 47 and 47 are of said predetermined dimensions such that the anterior flanges 47 and 48 forms the front element of the protective forehead pad cover assembly 40 which covers substantially the ventral side 80 of the external forehead pad interface 39 and overlaps the posterior portion 42 of the forehead pad cover assembly 40 when in the closed position installed around the external forehead pad interface 39, as illustrated in FIGS. 1, 2, 31, and 36.

Further illustrated in FIGS. 9, 10, 13, and 14, cutting across the anterior longitudinal-double arched edge 66 and 67 of the forehead pad cover is a substantially 1.0-1.5 inch(es) longitudinal vertical cut 57 extending therein the anterior portion 41 forming two anterior symmetrical bilateral-inverted U-shaped flanges, as illustrated in FIGS. 9, 10, 13 and 14, forming a right anterior flange 47 and a left anterior flange 48. The right anterior flange 47 comprises two lateral sides, an exterior right lateral side 51 and an interior left lateral side 52 joined by a right arched anterior edge 54; and the left anterior flange 48 comprises two lateral sides, and exterior left lateral side 49 and an interior right lateral side 50 joined by a left arched anterior edge 53.

Further, as illustrated in FIGS. 9, 10, 13, and 14, cutting throughin the top soft surface side 61 of the fleece material 83 through the reverse dull 62 side of the fleece material 83 forms a vertically aligned oval aperture 58, according to the preferred embodiment of the present invention, pivotally positioned a short distance below the longitudinal vertical cut 57 forming a vertically aligned oval aperture 58 sufficient in size to allow the top end 75 of a vertical main frame 72 of an orthodontic protraction headgear appliance 37 to pass throughin, upon installation of the forehead pad cover assembly 40 to an orthodontic protraction headgear appliance 37. The marginal edges of the vertical oval aperture 58 are reinforced with sewn stitches, as more clearly illustrated in FIG. 9

The protective forehead pad cover assembly 40 upon construction, as illustrated in FIGS. 9, 10, 13, and 14 further comprises two laterally spaced apart vertically aligned apertures 55a and 56a, or fastening mean elements, preferably at least two button holes 55a and 56a. Each button hole 55a and 56a is further configured in size to correspond to the complimentary fastening means, preferably at least two buttons 55 and 56 affixed to the obverse soft side 61 of the posterior portion 42 of the forehead pad cover assembly 40. A right button hole 56a is cut and vertically aligned centrally throughin the right anterior flange 47 and further aligned to correspond to the corresponding button 56 pivotally positioned on the posterior portion 42 of the protective forehead pad cover assembly 40 and pivotally positioned a predetermined short distance below the right flange 47 anterior arched edge 53. A left button hole 55a is cut and vertically aligned centrally throughin the left anterior flange 48 and pivotally positioned a short distance from the left flange anterior arched edge 54 and further aligned to correspond to the corresponding button 55 pivotally positioned on the obverse soft side 61 of posterior portion 42. The button holes 55a and 56a are formed within the left anterior flange 48 and the right anterior flange 47 by cutting through the top obverse soft 61 surface of the fleece material 83 throughin to the dull reverse side 62 of the fleece material 83 to form the open apertures. The apertures of the button holes 55a and 56a are reinforced by sewing stiches around the marginal edges of the apertures thereby forming two secure apertures or button holes 55a or 56a to removably affix to two corresponding buttons 55 and 56 positioned within the posterior portion 42 of the forehead pad cover assembly 40.

With the obverse soft side 61 of the fleece material 83 facing up towards the viewer, a fastening means element, preferably at least two buttons 55 and 56, as illustrated in FIGS. 9 and 13, and shown in FIGS. 27 and 30, is pivotally positioned and affixed with the obverse soft side 61 of the fleece material 83 facing up towards the viewer. It is important to affix the two buttons 55 and 56 to the obverse soft side 61 of the fleece material 83 because upon installation of the forehead pad cover assembly 40 onto the external forehead pad interface 39, the buttons 55 and 56 are facing out from the ventral side 80 of the external forehead pad interface 40 and more particularly not pressing against the skin of the wearer. The buttons 55 and 56 are laterally spaced a predetermined distance apart from each other to correspond to the corresponding button holes 55a and 56a, and the two buttons are pivotally positioned a short distance up from the longitudinal posterior edge 46.

As described, the protective forehead pad cover assembly 40 ensures a snug fit over the external forehead pad interface 39. Each anterior flange 48 and 47 of the forehead pad cover assembly 40 is removably intraengaged to the posterior portion 42 of the forehead pad cover assembly 40 by a fastening means, preferably two buttons 55 and 56. The posterior portion 42 of the forehead pad cover assembly 40 is secured to each of the anterior flanges 48 and 47 by inserting the affixed left button 55 through its corresponding left button hole 55a affixed within the left anterior flange 48; and similarly inserting the affixed right button 56 into the corresponding right button hole 56a affixed within the right anterior flange 47, as shown in FIGS. 1, 2, 31(a) and 36.

In addition, buttons 55 and 56 are preferred fastening means because upon installation of the protective forehead pad cover assembly 40 to the external forehead pad interface 39, the buttons 55 and 56 resemble eye features on a face where the vertical main frame 72 resembles a neck. This configuration of the protective forehead pad cover 40 is humorous for the orthodontic patient and disguises the medicinal, harsh appearance of an orthodontic protraction headgear appliance 37; provides a friendlier looking orthodontic protraction headgear apparatus 39 and thereby the forehead pad cover assembly 40 promotes increased compliance to use the external orthodontic protraction headgear appliance 37 during treatment of Class III Malocclusion disorder, especially among growing children and adolescent patients.

A V-shaped marginal dart cut-out 65, as illustrated in FIGS. 9, 10, 13 and 14, and shown in FIGS. 27, 28, 29, 30, 32, 33, 34, 35 is cut substantially ¼ inch across the marginal posterior longitudinal edge 46 of the fleece material 83 of the forehead pad cover assembly 40. The V-shaped dart cut-out 65 is dimensionally constructed and centrally positioned along the marginal posterior longitudinal edge 46 along the longitudinal axis 59 to receive an external screw 74 located on an external forehead pad interface 39 intraengaged with a vertical main frame 72 of the external orthodontic protraction headgear appliance 37. The V-shaped dart cut-out 65 is pivotally positioned and sufficiently sized to correspond with the external screw 74, which is affixed to the vertical main frame 72 and external forehead pad interface 39. As illustrated in FIG. 30, upon installation of protective forehead pad cover assembly 40 to the top end 75 of the vertical main frame 72 the V-shaped dart cut-out 65 is so shaped that when the marginal posterior edge 46 covers the ventral side 80 of the external forehead pad interface 39 the V-shaped dart cut-out 65 thus formed receives the forehead pad interface's screw 74, as illustrated in FIG. 30.

FIGS. 9 and 10 illustrate a completed uninstalled forehead pad cover 40 with the obverse side up. As will be observed the obverse soft surface 61 of the chassis core portion 43 of the forehead pad cover 40 is soft, smooth, seamless, and unobstructed, to afford optimum comfort to the wearer, as illustrated in FIG. 37 As a result of this construction, the obverse soft side 61 of the chassis core portion 43 of the protective forehead pad cover assembly 40 will provide a soft, absorbent membrane congruent to the wearer's facial skin on the forehead, as illustrated in FIGS. 1, 2, 31(b)-(c), 35 and 37, and contemporaneously the dull side 62 of the chassis core portion 43 will be congruent with the hard surface of the dorsal side 79 of the external forehead pad interface 39, as illustrated in FIGS. 28, 29, 30, 34, and 35 such that the chassis core portion 13 is positioned between the wearer's forehead and the dorsal side 79 of the external forehead pad interface 39, providing a membrane therebetween, as illustrated in FIGS. 1, 31(b)-(c), and 35.

The forehead pad cover assembly 40, as shown in FIG. 37 has a smooth contour, conformably fitting the external forehead pad interface 39 which conformably fit the contours of the wearer's head, and as shown being used by an orthodontic patient in FIGS. 1 and 2 and thereby effective to mitigate friction and chaffing to the wearer's forehead and consequentially preventing the development of cracked skin, redness, breakouts, lingering linear indentations, allergic reactions, pressure sores, decubitus sores, microbial infection, and other skin disorders. Further, as illustrated in FIG. 37 there are no overlapping stitches and thus no bulky multiple stitched points or areas within the chassis core portion 43 of the forehead pad cover assembly 40. Consequently, the wearer will not be exposed to the irritation and chaffing that can be caused by ridged or ribbed stitching. In addition, the forehead pad cover assembly 40 will provide the wearer with additional cushioning, absorbing, buffering, means wherein the chassis core portion 43 provides an absorbing fleece membrane marshaled between the wearer's forehead and the hard surface of the external forehead pad interface 39.

The fleece material 83 of the forehead pad cover assembly 40 is sufficient to provide additional cushioning to the forehead and helps distributes the forces acting on the skin localized at contact points upon the forehead, thereby reducing the amount of friction in between the skin and the hard surface of the forehead pad interface 39; and thereby reduces chaffing, but does not interfere with the proper fit of the external forehead pad interface 39 and the forces imposed by same. More particularly, it can be seen that the obverse soft 61 surface of the forehead pad cover assembly 40 cushions the skin on the forehead, including any pre-existing pressure sore that may be present on the forehead.

The forehead pad cover assembly 40 comprises open non-seemed or unhemmed edges, as illustrated in FIGS. 1, 31(b)-

(c) to provide for improved air circulation between the wearer's forehead and the hard surface of the forehead interface appliance 39.

The forehead pad cover assembly 40 is of predetermined measurements such that when the forehead pad cover assembly 40 is installed upon the external orthodontic protraction forehead pad interface 39, the dull side 62 of the chassis core portion 43 is positioned congruent with the dorsal side 77 of the forehead pad interface 39, and each anterior flange 48 and 47 folds over the anterior longitudinal edges of each shoulder member 70 and 71 of the external forehead pad interface 39 and the posterior portion 42 of the forehead pad cover assembly 40 folds over and around the posterior longitudinal edges of the external forehead pad interface 39 and such that the anterior portion 41 of the forehead pad cover 40 overlaps the posterior portion 42 of the forehead pad cover 40, and the posterior portion 42 underlaps the anterior flanges 47 and 48, and thereby completely covering the dorsal 79 and ventral 80 sides of the external forehead pad interface 39, as illustrated in FIGS. 1, 2, 31, 36, and 37. The forehead pad cover assembly 40 is installed thereon the external forehead pad interface 39 and the forehead pad cover 40 is removably intraengaged with fastening means, preferably buttons 55 and 56 and corresponding button holes 55*a* and 56*a*.

The buttons 55 and 56 are affixed to the obverse soft 61 side of the fleece material 83, as mentioned above, within the posterior portion 42 such that when the posterior portion 42 of the forehead pad cover 40 is folded around the posterior edge of the forehead pad interface 39 the buttons 55 and 56 are facing out and can be easily secured by the corresponding fastening means, button holes 55*a* and 56*a* affixed to each anterior flange 48 and 47. With this method of construction and installation, the anterior flanges 47 and 48 overlap the posterior portion 42, and the buttons 55 and 56 are displayed towards the viewer and the configuration of the buttons mimic a face, as illustrated in FIGS. 2 and 36. More importantly, the buttons are not pressed against the wearer's forehead.

As described, construction and manufacture of the orthodontic protraction headgear forehead pad cover assembly 40 is economical, straightforward, and uses a minimal amount of material and fastening means.

Method and Installation of Use of Orthodontic Protraction Headgear Appliance Protective Cover Assembly A method for using a protective chin cup cover assembly 10 and a protective forehead pad cover assembly 40, according to the preferred embodiment of the present invention is also disclosed and claimed. The method of installation of a protective chin cup cover assembly 10 is illustrated in FIGS. 22-26. The method of installation of a protective forehead pad cover is illustrated in FIGS. 27-31. In addition, FIGS. 1, 2, 32, 33, 34, 35, 36, 37, illustrates the method of installation and use of the protective chin cup cover assembly 10 and the protective forehead pad cover assembly 40 together as typically installed and used with an external orthodontic protraction headgear appliance 37 during treatment to a patient with Class III Malocclusion disorder.

For descriptive purposes only, and not claimed in the instant invention, the external orthodontic protraction headgear appliance 37, as described above, and illustrated in FIGS. 3, 4, 5, and 6, includes a vertical main frame 72 with two opposing ends, a top end 75 and a bottom end 76, and a chin cup interface 38 and a forehead pad interface 39. The external chin cup interface 38 is described with having a right shoulder member 68 and a left shoulder member 69; and similarly the external forehead pad interface 39 is described with having a right shoulder member 70 and a left shoulder member 71 to assist in the description of installation of the present invention. In addition, the external orthodontic protraction appliance includes a horizontal crossbar 73, and elastic bands 81 and screw 74 interconnecting vertical main frame 72 and forehead pad interface 39. FIG. 6 illustrates a patient wearing the orthodontic protraction headgear appliance 37 without the protective chin cup cover assembly 10 and without the forehead pad cover assembly 40 of the present invention installed thereon. FIGS. 1 and 2 illustrates a patient wearing the orthodontic protraction headgear appliance 37 with the protective chin cup cover installed 10 and with the protective forehead pad cover assembly 40 installed.

Installation of Protective Chin Cup Cover Assembly 10

The method of installation and use of the chin cup cover assembly 10 includes temporarily installing the protective chin cup cover assembly 10 to the external chin cup interface 38 of the orthodontic protraction headgear appliance 37 to provide a soft absorbent cushioning membrane between a patients chin and the hard plastic of an external chin cup interface 38, to a patient wearing the orthodontic protraction headgear appliance 37 during treatment of Class III Malocclusion disorder.

To install and use the protective chin cup cover assembly 10, initially, the wearer holds the external headgear with the vertical main frame's 72 convex side closest to the wearer thereby the ventral side 78 of the external chin cup interface 38, and the ventral side 80 of the external forehead interface 39 are facing towards the user exposing the set screw 74 hardware of the forehead pad interface 39 and vertical main frame 72 in the line of sight of the user.

Thereafter, upon installation, as illustrated in FIGS. 22, 34 and 35 the user will maneuver the protective chin cup cover assembly 10, according to the preferred embodiment of the present invention, such that the chin cup cover assembly 10 is held behind the vertical main frame 72 with the dull 32 surface of the pleated 84 chassis portion 13 congruent with the dorsal side 77 of the external chin cup interface 38 forming a three layered membrane between the hard surface of the external chin cup interface 38 and the wearer's chin. The dull 32 side of the chin cup cover assembly is seen by the viewer and the obverse soft 31 unobstructed side of the chin cup cover assembly 10 with buttons 25 and 26 is facing away from the user at this time.

Thereafter, as illustrated in FIG. 23 the bottom end of the vertical main frame 72 of the orthodontic protraction appliance is inserted throughin the horizontally aligned oval aperture 28 pivotally positioned within the posterior portion 12 of the chin cup cover assembly 10 while the pleated 84 chassis core portion 13 is disposed behind the external chin cup interface 38, such that the pleated 84 side of the chin cup cover chassis portion 13 is congruent with the dorsal side 77 of the chin cup interface 38. The dull 32 side of the protective chin cup cover assembly 10 is facing the viewer and the reverse side of the buttons 25 and 26 showing the affixing stitches 34 and 35 is seen and the soft 31 unobstructed side of the chassis portion 13 is away from the wearer at this time. FIGS. 32 and 33 is a perspective view of the protective chin cup cover assembly 10 as viewed by the wearer, with the bottom end of the vertical main frame 76 inserted throughin the horizontal aperture 28 and showing the obverse soft side 31 of the chin cup cover assembly 10 and buttons 25 and 26.

Thereafter, as illustrated in FIG. 24 the posterior portion 12 of the chin cup cover assembly 10 is extended around and over the bottom edge of the external headgear chin cup interface 38 and upwardly inward towards the ventral side 78 of the external chin cup interface 38, thereby revealing the obverse soft 31 side of the chin cup cover 10 showing at the two buttons 25 and 26 affixed therein, which are now facing out towards the user.

The anterior portion 11 of the chin cup cover assembly 10, as described above, includes a left anterior flange 18 and a right anterior flange 17. As illustrated in FIGS. 24 and 25, the left anterior flange 18 is maneuvered and is extended around and over the left shoulder member 69 of the external chin cup interface 38 revealing the obverse soft side 31 of the chin cup cover 10 wherein a corresponding fastening means is affixed, a vertically aligned button hole 25a. Further, as illustrated in FIG. 26, the left button 25 affixed to the posterior portion 12 of the chin cup cover 10 is inserted throughin the corresponding left button hole 25a configured within the left anterior flange 18 and therewith intraengages the left anterior flange 18 to the posterior portion 12 of the chin cup cover 10 to secure the chin cup cover assembly 10 to the external chin cup interface 38 of the orthodontic protraction headgear appliance 37, and such that the left anterior flange 18 overlaps and conceals a substantial portion of the posterior portion 12 of the chin cup cover assembly 10, and the posterior portion 12 underlaps the left anterior flange 18, according to the preferred embodiment of the present invention. Similarly, the right anterior flange 17 of the chin cup cover assembly 10 is maneuvered and is extended around and over the right shoulder 68 of the external chin cup interface 38 revealing the soft side 31 of the chin cup cover 10 wherein a corresponding fastening means is affixed, preferably a vertically aligned button hole 26a. Further, as illustrated in FIG. 26, the right button 26 affixed to the posterior portion 12 of the chin cup cover 10 is inserted throughin the corresponding right button hole 26a configured within the right anterior flange 17 and therewith intraengages the right anterior flange 17 to the posterior portion 12 of the chin cup cover 10 to secure the chin cup cover assembly 10 to the external chin cup interface 38 of the orthodontic protraction headgear appliance 37, and such that the right anterior flange 17 overlaps and conceals a substantial portion of the posterior portion 12 of the chin cup cover assembly 10, and the posterior portion 12 underlaps the left anterior flange 17, according to the preferred embodiment of the present invention.

As illustrated in FIGS. 24 and 25 each of the anterior inverted U-shaped flanges 17 and 18 folds forward over each of the corresponding shoulder members 68 and 69 of the external chin cup interface 10 to form the front top part of the protective chin cup cover assembly 10, as illustrated in FIGS. 1, 2, 26(a), and 36 and thereby covers and conceals the generally the top part of the ventral side 78 of the chin cup interface 38; and as illustrated in FIGS. 24 and 25 the posterior portion 12 folds up and over the bottom edge of the chin cup interface 38 and upward urged towards each of the anterior flanges 17 and 18 to form generally the bottom part of the chin cup cover 10 and thereby conceal and cover the bottom part of the external chin cup interface 38. Consequentially, the fastening means, preferably buttons 25 and 26 affixed within the soft obverse side 31 of the posterior portion 12 are revealed to the viewer.

The right button 26 affixed to the posterior portion 12 of the chin cup cover 10 is inserted throughin the corresponding button hole 26a configured within the right anterior flange 17 and therewith intraengages the right anterior flange 17 to the posterior portion 12 of the protective chin cup cover 10 such that the right anterior flange 17 overlaps and conceals a substantial portion of the posterior portion 12 of the chin cup cover assembly 10 and the ventral side 78 of the exterior chin cup interface 38 to secure the chin cup cover assembly 10 to the external chin cup interface 38 of the orthodontic protraction headgear appliance 37, according to the preferred embodiment of the present invention. Accordingly, the left button 25 affixed to the posterior portion 12 of the chin cup cover 10 is inserted throughin the corresponding button hole 25a configured within the left anterior flange 18 and therewith intraengages the left anterior flange 18 to the posterior portion 12 of the chin cup cover 10 such that the left anterior flange 18 overlaps and conceals a substantial portion of the posterior portion 12 of the chin cup cover assembly 10 and the ventral side of the exterior chin cup interface 38 to secure the chin cup cover assembly 10 to the external chin cup interface 38 of the orthodontic protraction headgear appliance 37, according to the preferred embodiment of the present invention. As illustrated in FIGS. 26(a) and 26(b) the chin cup cover assembly 10 snugly surrounds and covers the headgear chin cup interface 38 on the dorsal side 77 and the ventral side 78, with the chin cup cover 10 having open lateral sides 85 and 86. In such a configuration, almost zero relative movement can occur between the fleece protective chin cup cover assembly 10 and the headgear chin cup interface 38.

The protective chin cup cover assembly 10, according to the preferred embodiment of the present invention, as illustrated in FIGS. 1, 2, 26(a), 36 and 37 is now temporarily installed onto the external orthodontic protraction apparatus 37 ready for use by the wearer. When the wearer attaches the orthodontic protraction headgear appliance 37 to the patient's teeth and face, the chin cup cover assembly 10 is correctly positioned with the soft 31 unobstructed side of the chassis core portion 13, as illustrated in FIG. 37, of the chin cup cover assembly 10 congruent with the wearer's chin and the dull 32 pleated 84 side of the chassis core portion 13 of the chin cup cover 10 is congruent with the hard surface of the dorsal side 77 external chin cup interface 38. According to this method of installation, the protective chin cup cover 10 assembly provides a soft, absorbent, cushioning membrane marshaled between the wearer's chin and the hard surface of the external chin cup interface 38, enabling protection against cracked skin, redness, breakouts, mouth leakage buildup, and development of facial indentations, pressure sores and decubitus sores, and other skin disorders.

As illustrated in FIGS. 3, 26, and 36, the vertical main frame 72 extends in both directions longitudinally between the right anterior flange 17 and the left anterior flange 18 and throughin the horizontally aligned aperture 28 where the chin cup cover assembly 10 is now in the closed position around the external chin cup interface 10 with the two buttons 25 and 26 fastened and facing the viewer and therefore the buttons do not press against the patient's chin.

The protective chin cup cover assembly 10 comprises a soft stretchable fleece material 82 which is stretchable in two opposing directions along the lateral axis 30 of the chin cup cover such that the two-way stretch is antagonist to the pull of the posterior 12 and anterior portion 11 of the chin cup cover assembly 10 when extended in opposing directions and urged towards each other around and over the edges of the external chin cup interface 38. In this way, the form of the protective chin cup cover 10 is maintained upon installation of the chin cup cover 10 during use and provides for a longer life of the chin cup cover assembly 10 for use by the orthodontic patient. As described, the protective chin cup cover assembly 10 fleece material 82 is stretchable to ensure a snug fit over the interface shoulder members 68 and 69 of the external chin cup interface 38.

As illustrated in FIGS. 1, 2 and 26(a)-(c) when the chin cup cover 10 is in the closed position and installed upon the external chin cup interface 38 during use lateral openings at 85 and 86 are formed in addition to the lateral side openings 87 and 88 formed by the pleat at 87 and 88 which are unhemmed or unseamed and thereby allowing air to circulate throughin the chin cup cover assembly 10 and the wearer's chin. The lateral side openings 85 and 86 of the chin cup cover 10 remain open to enable proper aeration and circulation of air throughout the chin cup cover 10 while in use. More particularly, choosing not to affix the chin cup covering assembly 10 lateral side openings 85 and 86, and pleat 84 lateral side openings 87 and 88 and keeping them in an open configuration allows for proper washing and drying of both the outside and inside of the absorbent, cushioned, double layered pleat 84 and the protective chin cup cover assembly 10 as configured in the preferred embodiment of the present invention.

The two buttons 25 and 26 provide a secure fastening means to temporarily install and close the chin cup cover assembly 10 around the external chin cup interface 38 and to easily remove the chin cup cover assembly 10 from the external chin cup interface by simply unbuttoning the two buttons 25 and 26 fastened between the anterior flanges 17 and 18 and the posterior portion 12; and the two buttons provide a decorative means to the chin cup cover assembly 10.

Furthermore, it can be seen, as illustrated in FIGS. 26(b)-(c) and 34 the folded double layered pleat 84 chassis portion 12 of the chin cup cover 10 is congruent with the dorsal side 77 of the hard surface of the external headgear chin cup interface 38 and therefore the movement of the chin cup cover assembly 10 between the skin of the chin and the hard surface of the dorsal side 77 of the chin cup interface 38 remains relatively static. Similarly, the soft obverse side 31 of the chin cup cover assembly 10 is congruent with the skin of the wearer's chin and the fleece material 82 between the wearer's skin and the movement of the chin cup cover assembly 10 remains relatively static. Therefore, the frictional forces imposed upon the chin by the hard surface of the external orthodontic chin cup interface 38 is reduced. Furthermore, the presence of the chin cup cover assembly 10 abutting against the wearer's chin buffers the chin and distributes may of the forces that are imposed by the orthodontic protraction headgear appliance 37 and external chin cup interface 38 so that those forces are not experienced at a concentrated point on the wearer's chin and assuages the discomfort of wearing the orthodontic protraction headgear appliance 37.

The predetermined configured bilaterally-symmetrical anterior inverted U-shaped flanges 18 and 17; the pivotally positioned vertically aligned button holes 25a and 26a; together with the two pivotally positioned buttons 25 and 26 on the posterior portion 13 of the protective chin cup cover assembly10; and the pivotally positioned horizontal aperture 28 within the posterior portion 12 of the chin cup cover assembly 10; together allows for an installation of the chin cup cover assembly 10 upon and around the external chin cup interface 38 amenable to the preferred embodiment of the present invention and its primary objective, which is to provide a three layered membrane between the wearer's chin and the hard surface of the exterior chin cup interface 38 and thereby a wearer's chin and facial skin and its underlying tissue, is never touching the external chin cup interface 38; and provides a three layered membrane which provides for increased absorption of mouth leaks and the like; increased cushioning between the wearer's chin and the hard surface of the chin cup interface 38, and increased buffering of forces applied against the wearer's chin bone, facial skin at the site of the chin, and underlying tissues to enable prevention against redness, cracked skin, breakouts, pressure sores, and other skin disorders, and general discomfort imposed upon the orthodontic patient as a result of wearing the orthodontic protraction headgear appliance 37 during treatment of Class III Malocclusion disorder.

As described and illustrated, the chin cup cover assembly 10 can be installed onto the external chin cup interface 38 ready for use by the wearer. In addition, this preferred configuration and method of use provides for easy installation of the chin cup cover assembly 10 and easy removal of the chin cup cover assembly 10 from the external chin cup interface 37 and therefore provides easy access to wash and maintain the protective chin cup cover assembly 10.

Fastening means, as described above, according to the preferred embodiment of the present invention, are preferably two buttons 25 and 26, but can include fastening means such as, plurality of buttons, hook and loop fasteners, hook and eyes, snaps, ties, ribbons, VELCRO®. The number and placement of the fastening means can vary so as to provide various designs. In addition, in another embodiment of the present invention, a plurality of fastening means can be arranged in apportioned distances from each other to allow for an adjustment of the protective chin cup cover assembly 10 for varying sizes of chin cup interfaces.

The protective chin cup cover assembly 10 can be configured in various dimensions corresponding to the manufactured orthodontic protraction headgear appliance. For instance, smaller sizes would be used in pediatric orthodontic patients and larger sizes would be used for adolescent orthodontic patients.

Aesthetically, with this method of installation of the chin cup cover assembly 10 on the external chin cup interface 38, the two buttons 25 and 26 are displayed towards the viewer and the configuration of the buttons resemble the features of eyes on a face and thereby provide humor for the orthodontic patient and minimizes the hard medicinal appearance of the external orthodontic appliance and consequentially promotes an increase in compliance of use of the external orthodontic protraction headgear appliance by growing children and adolescents.

Installation of Protective Forehead Pad Cover Assembly 40

The method of installation and use of the protective forehead pad cover assembly 40 includes installing the forehead pad cover assembly 40 to the external orthodontic headgear forehead pad interface 39 of the orthodontic protraction headgear appliance 37 to provide a soft absorbent cushioning buffering membrane between a patients forehead and the hard plastic of an external headgear pad interface 39 to a patient wearing the orthodontic protraction headgear appliance 37 during treatment of Class III Malocclusion disorder.

To install and use the protective forehead pad cover assembly 40, initially the wearer holds the external headgear with the vertical main frame's 72 convex side closest to the wearer thereby the ventral side 80 of the external forehead pad interface 39 is facing the user exposing the screw 74 hardware of the external forehead pad interface 39 intraengaged to the vertical main frame 72 in the line of sight of the user.

Thereafter, as illustrated in FIG. 28, the protective forehead pad cover assembly 40 is held behind the external vertical mainframe 72 and behind the external forehead pad interface 39 to which it will be installed upon, such that the dull side 62 of the protective forehead pad cover assembly 40 is facing the viewer and the threaded stitches at 63 and 64 affixing the two buttons 55 and 56 to the posterior portion 42 of the forehead pad cover assembly 40 are in view. As illustrated in FIGS. 28-30, and 33, the dull side 62 chassis core portion 43 of the forehead pad cover assembly 40 is congruent to the dorsal side 79 of an external forehead pad interface 39. The soft obverse side 61 of the protective forehead pad cover assembly 40 with affixed buttons 55 and 56, as illustrated in FIG. 27, is facing away from the viewer at this time. As illustrated in FIG. 27 as and viewed from the obverse soft side 61, which will be close to the wearer of the forehead pad cover assembly 40, the top end 75 of the vertical main frame 72 is inserted up throughin the vertical aperture 58 such that the right anterior flange 47 and the left anterior flange 48 are positioned on either side of the top end 75 of the vertical main frame 72 of the orthodontic protraction headgear appliance 37.

Thereafter, as illustrated in FIG. 28 and further illustrated in FIG. 29 the top end 75 of the vertical main frame 72 is inserted throughin the vertical aperture 58 and pulled up therethrough so that the top end 75 of the vertical mainframe 72 is between the right inverted U-shaped anterior flange 47 and the left inverted U-shaped anterior flange 48.

In addition, as illustrated in FIG. 30, upon further installation of the protective forehead pad cover assembly 40, with the dull side 62 chassis core portion 43 pivotally maneuvered congruent with the dorsal side 79 of the forehead pad interface 39, the posterior portion 42 of the forehead pad cover 40 folds up and over the posterior edge of the external forehead pad interface 39 and inward towards the ventral side 80 of the external forehead pad interface 39 member whereupon the V-shaped dart cut-out 65 located along the posterior edge 46 of the forehead pad cover assembly 40 receives the external metal screw 74 located on the orthodontic protraction headgear appliance 37 to pass therein. Further, as illustrated in FIGS. 30 and 31, upon folding the posterior portion 42 up and over the posterior edge 42 of the external forehead pad interface 39 the fastening means, two buttons, a right button 56 and a left button 55, affixed to the soft side 61 of the forehead pad cover assembly 40 are revealed.

Thereafter, as illustrated in FIG. 30, the anterior left flange 48 of the forehead pad cover assembly 40 is extended around and over the left shoulder member 71 of the external forehead pad interface 39 inward towards the ventral side 80 of the same, as such, the soft obverse side 61 of the left anterior flange 48 is facing out and the corresponding left button hole 55a is revealed. As illustrated in FIG. 31, the left button 55 affixed to the posterior portion 42 of the forehead pad cover assembly 40 is inserted throughin the corresponding left button hole 55a configured therein the left anterior flange 48, and therewith intraengages the left anterior flange 48 to the posterior portion 42 of the forehead pad cover assembly 40 such that the left anterior flange 48 overlaps and conceals a portion of the posterior portion 46 of the forehead pad cover assembly thereby enabling the forehead pad cover assembly 40 secure installation to the external forehead pad interface 39 of the external orthodontic protraction headgear appliance 37. Similarly, as illustrated in FIG. 30 the anterior right flange 47 of the forehead pad cover assembly 40 is extended around and over the right shoulder member 70 of the external forehead pad interface 39 inwardly towards the ventral side 80 of same, as such, the soft obverse side 61 of the right anterior flange 47 is facing out and the right button hole 56a is revealed. Further, as illustrated in FIG. 31, the right button 56 affixed to the posterior portion 46 of the forehead pad cover assembly 40 is inserted throughin the corresponding right button hole 56a configured therein the right anterior flange 47, and the forehead pad cover assembly 40 is in its closed position.

Now, the protective forehead pad cover assembly 40, according to the preferred embodiment of the present invention snugly surrounds the headgear forehead pad interface 39, as illustrated in FIGS. 1, 2, 31(a)-(c), 35, 36, and 37. In such a configuration, almost zero relative movement can occur between the fleece forehead pad cover assembly 40 and the external forehead pad interface 39. The forehead pad cover assembly 40 is now temporarily installed onto forehead pad interface 39 of the external orthodontic protraction apparatus 37 ready for use by the wearer.

When the wearer attaches the orthodontic protraction headgear appliance 37 to the wearer's teeth and face, as illustrated in FIGS. 1, and 2, the forehead pad cover assembly 40 is correctly positioned with the obverse soft side 61 of the fleece material 83 of the forehead pad cover assembly 40 congruent with the wearer's skin at the site of the forehead; and as illustrated in FIGS. 31(b)-(c), 34 and 35 the dull side 62 of the fleece material 62 of the forehead pad cover assembly 40 is congruent with the hard surface of the dorsal side 79 of the orthodontic headgear chin cup interface 39.

The method of installation of the headgear forehead pad cover assembly 40 as illustrated in FIGS. 27-31, and 35, the headgear forehead pad cover assembly 40 is positioned such that the obverse soft pile side 61 of the fleece material 83 of the chassis portion 43 of the forehead pad cover assembly 40 is congruent with the skin of the wearer's forehead and the duller side 62 of the fleece fabric 83 of the forehead pad cover assembly 40 is congruent with the hard material of the external forehead pad interface 39, according to the preferred embodiment of the present invention. Therefore, the chassis core portion 43 of the forehead pad cover assembly 40 provides a soft, absorbent, buffering membrane the wearer's forehead and the hard surfaces of the external forehead interface 39 of the orthodontic protraction headgear appliance 37. According to this method of installation, the protective chin cup cover assembly 40 provides a soft, absorbent, cushioning membrane marshaled between the wearer's forehead and the hard surface of the external forehead pad interface 39, enabling protection against cracked skin, redness, breakouts, mouth leakage buildup, and development of facial indentations, pressure sores, and other skin disorders which can develop while an orthodontic patient is wearing an external orthodontic headgear appliance 37.

The chassis core portion 43 is configured in predetermined measurements to correspond in size to the length and width of an external headgear forehead pad interface 39 and further configured to correspond to the surface area of the dorsal side 79 of the forehead pad interface 39 such that, as illustrated in FIGS. 28, 33, 34, 35, and 37, when the chassis portion 43 of the forehead pad cover assembly 40 is placed congruent to the dorsal side 79 of the external forehead pad interface 39 the total top surface area of the dorsal side 79 of the external forehead pad interface 39 is covered by the chassis portion 43. As illustrated in FIGS. 27-31 and 36, the predetermined pivotally configured flanges 48 and 47 of the forehead pad cover assembly 40; the pivotally positioned vertical button holes 55a and 56a within each of the anterior flanges 48 and 47; together with pivotally positioned buttons 55 and 56 on the posterior portion 42 of the headgear forehead pad cover assembly 40; pivotally positions and secures the anterior flanges 48 and 47 intraengaged with the posterior portion 42 in proper alignment to cover and conceal the ventral side 80 of the external forehead pad interface 39 of the external forehead pad interface 39, and the chassis portion 43 in proper alignment to cover and conceal the dorsal side 79 of the forehead pad interface 39.

As illustrated in FIGS. 27, 30 and 31, preferably two buttons 55 and 56 are affixed to the obverse soft side 61 of the fleece material 83 forehead pad cover assembly 40 positioned at a predetermined distance apart on the same lateral axis and pivotally positioned at a site generally within the posterior portion 42 aligned with the corresponding button holes 55a and 56a, such that when the forehead pad cover assembly 40 is installed upon an external forehead pad interface 39 the buttons 55 and 56 are juxtaposed on either side of the vertical main frame 72 of the orthodontic protraction headgear appliance 37, where the buttons mimic the eyes of a face. FIGS. 31(*a*) and 36, and also in FIGS. 1 and 2, illustrates the installed forehead pad cover and the preferred location of the fastening means, preferably two buttons, 55 and 56. The buttons 55 and 56 are facing outward away from the protective forehead pad cover assembly 40 and towards the viewer to allow for easy access to the buttons 55 and 56 for easy installation and removal of the forehead pad cover assembly 40.

This configuration and method of use provides for easy installation of the forehead pad cover assembly 40 and easy removal of the forehead pad cover assembly 40, which enable easy access to wash the forehead pad cover assembly 40 or to change the forehead pad cover assembly 40.

More particularly, the two fastening buttons 55 and 56 are located away from the skin of the wearer such that the buttons are not pressed against the wearer's forehead there is no discomfort to the wearer's forehead and skin. In addition, the buttons 55 and 56 provide an embellishment to the forehead pad cover assembly 40 which is decorative and can be personalized by the wearer by wearer selected buttons of their favorite colors, styles, indicia, gem stones, or their favorite team colors, and the like.

Further, as illustrated in FIGS. 28, 29, 30, 31(*a*) and 36, with the dull side 62 chassis core portion 43 of the forehead pad cover 40 congruent with the dorsal side 79 of the forehead pad interface 39, each of the anterior flanges 47 and 48 of the forehead pad cover assembly 40 fold forward over each of the shoulder members 70 and 71 of the external forehead pad interface 39 to form generally the front top part of the forehead pad cover assembly 40 and thereby covers and conceals generally the ventral side 80 of the external forehead pad interface 39; and the posterior portion 16 folds over the bottom edge of the external forehead pad interface 39 and upward and urged towards the anterior flanges 70 and 71 to form generally the bottom part of the forehead pad cover assembly 40 and thereby conceals and covers the bottom part of the external forehead pad interface 39. The anterior flanges 47 and 48 are urged toward the posterior portion 42 and the anterior flanges 47 and 48 overlap and cover a portion of the posterior portion 42 of the forehead pad cover assembly 40 and thereby the ventral portion 80 of the forehead pad interface 39 is substantially covered and concealed; and the chassis core portion 43 covers and conceals the dorsal side 79 of the forehead pad interface 39.

The lateral sides 44 and 45 of the forehead pad cover assembly 40 are open, as illustrated in FIGS. 30 and 31(*b*)-(*c*), and not hemmed or sewed, thereby allowing air to circulate throughin the forehead pad cover and the wearer's forehead. Further, the vertical main frame 72, as illustrated in FIGS. 1, 2, 30, 31(*a*), and 36 extends in both directions longitudinally between the right anterior flange 47 and the left anterior flange 48. As illustrated in FIGS. 1, 2, 31(*a*) and 36, the forehead pad cover assembly 40 is now in the closed position around the external forehead pad interface 39 and ready for use by the orthodontic patient. The forehead pad cover assembly 40 can be easily removed by unbuttoning the two buttons 55 and 56 and therefore can be washed or replaced conveniently.

The predetermined configured bilaterally-symmetrical anterior inverted U-shaped flanges 48 and 47; the pivotally positioned vertically aligned button holes 55*a* and 56*a*; together with the two pivotally positioned buttons 55 and 56 on the posterior portion 13 of the protective forehead pad cover assembly 40; and the pivotally positioned vertical aperture 58; together allows for an installation of the forehead pad cover assembly 40 upon and around the external forehead pad interface 39 amenable to the preferred embodiment of the present invention and its primary objective, which is to provide a membrane between the wearer's forehead and the hard surface of the exterior forehead pad interface 39 and thereby a wearer's forehead and facial skin and its underlying tissue, is never touching the external forehead pad interface 39; and provides a membrane which provides for increased absorption of perspiration and sweat and the like; increased cushioning between the wearer's forehead and the hard surface of a forehead pad interface 39, and increased buffering of forces applied against the wearer's forehead bone, facial skin at the site of the forehead, and underlying tissues to enable prevention against redness, cracked skin, breakouts, pressure sores, and other skin disorders, and general discomfort imposed upon the orthodontic patient as a result of wearing the orthodontic protraction headgear appliance 37 during treatment of Class III Malocclusion disorder.

Fastening means, as previously described in the protective forehead pad cover assembly 40, are preferably buttons, but can include fastening means such as, hook and loop fasteners, snaps, ties, ribbons, VELCRO®. The number and placement of the fastening means can vary so as to provide varying extending lengths around the external members of the forehead interface 39 and to provide various designs. A plurality of fastening means can be arranged in apportioned distances from each other to allow for an adjustment of the covers for varying sizes forehead pad interfaces of orthodontic appliances. The fastening means may be provided from a plurality of fastening means materials, including plastic, metals, metal alloy, or non-metal, and may have a plurality of shapes, designs, so as to maximize its effectiveness as a securing means and as an embellishment to express the personal style and design of the wearer.

The forehead pad cover assembly 40 can be configured in various dimensions corresponding to the manufactured orthodontic protraction headgear appliance 37. For instance, smaller sizes would be used in pediatric orthodontic patients and larger sizes would be used for adolescent orthodontic patients.

Aesthetically, with the method of construction and installation, as described above, and illustrated in FIGS. 1, 2, 31(*a*) and 36, the two buttons 55 and 56 are displayed towards the viewer and the configuration of the buttons resemble eyes of a face and the vertical main frame resembles a neck disguising the harsh medicinal appearance of the orthodontic protraction headgear appliance 37.

The protective forehead pad cover assembly 40 comprises a soft stretchable fleece material 83 which is stretchable in two directions along the lateral axis 60 of the forehead pad cover assembly 40 such that the two-way stretch is antagonist to the pull of the anterior flanges 47 and 48 urged towards the posterior portion 42 upon installation of the forehead pad cover assembly 40 on an external forehead pad interface 39. In this way, the foim of the protective forehead pad cover 40 is maintained upon installation and during use and therefore provides for a longer life of the forehead pad cover assembly 40. As described, the protective forehead pad cover assembly 40 fleece material 83 is stretchable to ensure a snug fit over the external forehead pad interface 39.

FIGS. 1, 2, 31(*b*)-(*c*), further illustrates the soft side 61 of the forehead pad cover assembly 40 positioned between the wearer's forehead and the hard material of the external forehead interface 39 such that the soft fleece creates a soft, absorbing, buffering, membrane between the skin and underlying tissues of the wearer's forehead and the external forehead pad interface 39; and thereby eliminates formation of cracked skin, redness, breakouts, lingering facial indentations, suction marks, pressure sores, decubitus sores, and the like, on the patient's forehead as a result of wearing an orthodontic protraction headgear appliance during treatment.

The design of the protective forehead pad cover assembly 40 improves the comfort and appearance of using the orthodontic protraction headgear appliance 37 and the attitude of the wearer thereby facilitating adjustment to a challenging change in lifestyle and thus improves compliance of therapy for orthodontic condition Class III Malocclusion.

In addition, the configuration and method of use of the protective forehead pad cover assembly 40 provides that the fastening means, preferably buttons 55 and 56, are displayed out towards the viewer, as illustrated in FIGS. 1, 2 and 36. The buttons 55 and 56 mimic a face and therefore add humor and a less medicinal appearance to the orthodontic appliance 37 and consequentially promotes an increase in compliance of use of the external orthodontic protraction headgear appliance 37 by growing children and adolescents.

As described and illustrated, the present invention comprises two aspects, a protective chin cup cover assembly 10, and a protective forehead pad cover assembly 40, according to the preferred embodiment of the present invention. The protective chin cup cover assembly 10, according to the preferred embodiment of the present invention, provides an upgraded chin cup cover assembly 10 comprising a three layered absorbent, cushioning, membrane which is of a predetermined thickness which enables for a more secure aerated attachment between the patient's chin and the external chin cup interface 38. In addition, the protective forehead pad cover assembly 40 provides an upgraded forehead pad cover assembly 40 comprising an absorbent, cushioning membrane, which is of a predetermined thickness which enables for a more secure aerated attachment between the patient's forehead and the external forehead pad interface 39. The use of the chin cup cover assembly 10 and the forehead pad cover assembly 40, as disclosed and described according to the preferred embodiment of the present invention, provides an absorbing, cushioning, buffering, membrane against the prescribed pressure required of the external chin cup interface against the wearer's chin; and provides an absorbing, cushioning, buffering, membrane against the prescribed pressure required of the external forehead pad interface against the wearer's forehead, while concurrently sustaining an improved seal with the chin and the forehead, thereby allowing the orthodontic protraction headgear appliance 37 to deliver treatment more effectively.

The preferred fastening means for the present invention are at least two buttons, 25 and 26; and 55 and 56, because they are easy to manipulate, provide secure fastening means, economical, and easy to replace. In addition, the buttons, 25 and 26; and 55 and 56, add a decorative and fanciful design to the chin cup cover assembly and the forehead pad cover assembly, respectively.

Different geometrical shapes can be configured to form the anterior flanges 17 and 18; and 47 and 48, of the present invention, as desired by the wearer, which may resemble animals, mascots, letters, or other indicia. Those skilled in the art upon reading the disclosure herein will readily recognize that flanges having various shapes may be employed in the chin cup cover assembly 10 and the forehead pad cover 40 without departing from the spirit and scope of the claims as set forth herein. In addition, apertures and their size and spacing may be used as needed to accommodate various orthodontic protraction headgear appliance styles. Relatedly, notches and their size and spacing may be used as needed to accommodate various orthodontic protraction headgear appliance styles. In addition, indicia can be inscribed on the cover as an identifying mark of ownership, or as a promotional mark.

The fleece material 82 of the protective chin cup cover assembly 10, provided in the present invention, provides a soft absorbent breathable membrane with wicking properties between the hard surface of the chin cup interface 38 and the wearer's chin and; the fleece material 83 of the protective forehead pad cover assembly 40 provides a soft textured barrier between the external forehead pad interface 39 and wearer's forehead, thereby enabling protection against the formation of red lines, lasting indentation, or suction marks, or red marks, from forming on the wearer's chin and the wearer's forehead when the patient is wearing orthodontic protraction headgear appliance during the day or when the patient is wearing the device while the patient sleeps at night. The soft protective chin cup cover assembly 10 and the soft protective forehead pad cover assembly 40 of the present invention increase the willingness to wear the orthodontic protraction headgear appliance and the ease of falling asleep and staying asleep with the orthodontic protraction headgear appliance on during treatment.

Use of the present invention, can dispel any conspiracy between Class III Malocclusion disorder and an orthodontic protraction headgear appliance to deprive young patients of the halcyon childhood they deserve. In addition, use of the present invention fosters compliance which is the key to successful treatment of Class III Malocclusion therapy. The soft fleece assuages the formation of lingering suction marks, and indentations on the patient's chin and forehead and thereby preventing further discomfort caused by embarrassment to the patient. The patient no longer has to explain to others or cover up the demarcations left on the wearer's face. Therefore, the present invention enables the patient to carry a more positive attitude to wearing the device and more particularly, a more positive self-esteem and self-image after taking the headgear off. The present invention provides an enabling means to reach a successful totality of the orthodontic protraction headgear appliance treatment for the patient to correct the Class III Malocclusion disorder. When the underbite is corrected the self-esteem and self-image of the patient is dramatically increased and better yet, wearing the headgear is terminated . . . . Doctor's orders!

While the present invention has been illustrated by the description of embodiments preferred, and while the embodiments have been described in considerable detail, it is not intended to restrict or in any way limit the scope of the appended claims to such detail. Additional advantages and modifications will be readily apparent to those skilled in the art. Accordingly, departures may be made from such details without departing from the scope or spirit of the invention.

What is claimed is:

1. A protective chin cup cover assembly adapted for installation on an external orthodontic protraction headgear appliance chin cup interface, the protective chin cup cover comprising:
    a single body unit of flexible absorbent soft material having two opposing lateral substantially parallel side edges extending between a longitudinal posterior edge and two longitudinal arched edges forming a posterior portion, an anterior portion, and a chassis core portion disposed therebetween;
    the protective chin cup cover assembly including a lateral axis and a longitudinal axis;

the flexible absorbent soft material further defined by the material having two sides, the two sides defined by an obverse soft side and a reverse dull side;

the posterior portion of the protective chin cup cover assembly, is defined by being substantially in the shape of a rectangle and including two opposing arcuate corners joined by a posterior edge;

a horizontally disposed aperture disposed along the longitudinal axis within the posterior portion a short distance from the posterior edge;

the chassis core portion is generally in the shape of a rectangle and includes a pleat;

the pleat includes a fold at a fold line F1 and is attached to the chassis core portion at a meeting of a first seam line S1 and a second seam line S2, the fold lines F1 and the seam lines S1 and S2 are cooperatively adapted to be capable of forming a three layered chassis core portion;

the anterior portion includes a right anterior flange and a left anterior flange, each anterior flange being generally arch-shaped, the right and left anterior flanges separated by a longitudinal cut, the right anterior flange comprises two generally parallel lateral sides, an exterior right lateral side and an interior left lateral side, joined by a right arched anterior edge;

the left anterior flange comprises two generally parallel lateral sides, an exterior left lateral side and an interior right lateral side, joined by a left arched anterior edge; and a fastening means on the right anterior flange and a fastening means on the left anterior flange removably engage anterior flanges to the posterior portion having a right corresponding fastening means and a left corresponding fastening means affixed thereon.

2. The protective chin cup cover assembly of claim 1, wherein the fastening means is one of the following group of fastening means: buttons, button receiving holes, snap or snaps, hook-and-loop fastener and hook and eyes.

3. The protective chin cup cover assembly as claimed in claim 2, wherein the buttons resemble eyes of a face.

4. The protective chin cup cover assembly of claim 1, wherein the flexible absorbent soft material comprises 100% polyester fleece.

5. The protective chin cup cover assembly (10) as in any one of claims 1 or 4 wherein material (82) comprises a pile having a depth in the range of approximately 1/16-2/16 inches in thickness.

6. The protective chin cup cover assembly of either claim 1 or claim 4, wherein the flexible absorbent soft material is affixed with a variety of embellishments selected from the group comprising one, of more of the following group of letters identifying wearer's initials, days of the week, night or day, favorite team letters and cartoon images.

7. The protective chin cup cover assembly of claim 1, wherein the pleat has unseamed or unhemmed lateral edges to enable improved washing and drying of exterior surfaces of the pleat and protective chin cup cover assembly.

8. The protective chin cup cover assembly of claim 1, wherein said flexible absorbent soft material comprises non-hemmed lateral edges.

9. The protective chin cup cover assembly of claim 1, wherein material comprises one of two way stretch or four-way stretch.

10. The protective chin cup cover assembly of claim 1, wherein soft absorbent flexible material is selected from a plurality of colors and designs which are identifiable to a sports team.

11. A protective chin cup cover assembly for installation on an external orthodontic protraction headgear appliance chin cup interface, the protective chin cup cover comprising:

a single body unit of flexible absorbent soft material having a generally rectangular shape, the single body unit having a longitudinal axis and a lateral axis;

the single body unit defined by an anterior portion on one end of the single body unit, a posterior portion on an opposite end of the single body unit and a chassis core portion located between the anterior and posterior portions;

the anterior portion includes a right anterior flange and a left anterior flange, each anterior flange being generally arch-shaped, the left and right anterior flanges separated by a longitudinal cut; and the posterior portion includes two separate fastening means, wherein each separate fastening means is located on an opposite side of the longitudinal axis;

a horizontal aperture is located in the posterior portion, the horizontal aperture having a generally elliptical shape with a major axis of the horizontal aperture generally parallel to the lateral axis;

the right anterior flange and the left anterior flange each contain a fastening means receiving hole;

the two separate fastening means on the posterior portion each removably engage each of the two fastening means receiving holes on the right anterior flange and the left anterior flange;

a fold line is located within the chassis portion, the fold line being substantially parallel to the lateral axis; and a first seam line, a second seam line and the fold line are cooperatively adapted to be capable of forming a three layered chassis core portion protective chin cup cover assembly.

12. The protective chin cup cover assembly of claim 11, wherein the fastening means is one of the following group of buttons, snaps, hook-and-loop fasteners and hook and eyes.

13. The protective chin cup cover assembly of claim 11, wherein soft absorbent flexible material is selected from a plurality of colors and designs which are identifiable to a sports team.

\* \* \* \* \*